United States Patent
Condie et al.

(10) Patent No.: US 7,445,931 B2
(45) Date of Patent: Nov. 4, 2008

(54) COMPOSITIONS AND METHODS FOR ENRICHMENT OF NEURAL STEM CELLS USING CERAMIDE ANALOGS

(75) Inventors: Brian G. Condie, Athens, GA (US); Erhard Bieberich, Augusta, GA (US)

(73) Assignees: Bresagen, Inc., Athens, GA (US); Medical College of Georgia Research Institute, Augusta, GA (US)

( * ) Notice: Subject to any disclaimer, the term of this patent is extended or adjusted under 35 U.S.C. 154(b) by 329 days.

(21) Appl. No.: 10/529,115

(22) PCT Filed: Sep. 25, 2003

(86) PCT No.: PCT/US03/30112

§ 371 (c)(1), (2), (4) Date: Aug. 15, 2005

(87) PCT Pub. No.: WO2004/029203

PCT Pub. Date: Apr. 8, 2004

(65) Prior Publication Data

US 2006/0014280 A1 Jan. 19, 2006

Related U.S. Application Data

(60) Provisional application No. 60/485,351, filed on Jul. 7, 2003, provisional application No. 60/413,510, filed on Sep. 25, 2002.

(51) Int. Cl.
*A61K 31/164* (2006.01)
*A61K 31/16* (2006.01)
*C12N 5/00* (2006.01)
*C12N 5/08* (2006.01)

(52) U.S. Cl. ............... 435/377; 435/325; 435/368; 514/513; 514/627; 514/727

(58) Field of Classification Search ............. None
See application file for complete search history.

(56) References Cited

U.S. PATENT DOCUMENTS

| | | | |
|---|---|---|---|
| 5,453,357 A | 9/1995 | Hogan | |
| 5,589,376 A | 12/1996 | Anderson et al. | |
| 5,753,506 A | 5/1998 | Johe | |
| 5,766,948 A | 6/1998 | Gage et al. | |
| 5,843,780 A | 12/1998 | Thomson | |
| 5,851,832 A | 12/1998 | Weiss et al. | |
| 5,958,767 A | 9/1999 | Snyder et al. | |
| 5,968,829 A | 10/1999 | Carpenter | |
| 6,200,806 B1 | 3/2001 | Thomson | |
| 6,245,566 B1 | 6/2001 | Gearhart et al. | |
| 6,410,597 B1 | 6/2002 | Bieberich et al. | |
| 6,562,619 B1 | 5/2003 | Gearhart et al. | |
| 6,833,269 B2 * | 12/2004 | Carpenter | 435/377 |

FOREIGN PATENT DOCUMENTS

WO WO 98/43679 10/1998
WO WO 99/53021 10/1999

OTHER PUBLICATIONS

Lindvall et al., Nature Medicine 10, S42-S50 (2004).*
Smith, Annu Rev Cell Dev Biol. 2001;17:435-462.*
Herget et al., J. Biol. Chem., vol. 275, Issue 39, 30344-30354, Sep. 29, 2000.*
Bieberich, 2004 "Integration of Glycosphingolipid Metabolism and Cell-Fate Decisions in Cancer and Stem Cells: Review and Hypothesis," *Glycoconjugate Journal* 21(6)315-327.
Buccoliero, et al., 2003 "The Roles of Ceramide and Complex Sphingolipids in Neuronal Cell Function," *Pharmacol. Re.* 47(5)409-419.
Toman, et al., 2000 "Role of Ceramide in Neuronal Cell Death and Differentiation," *J. Neurotrauma* 17(10)891-898.
Bain, et al., 1995, "Embryonic Stem Cells Express Neuronal Properties in vitro," *Dev. Biology*, 168:342-357.
Bieberich, et al., 2001, "Regulation of Apoptosis During Neuronal Differentiation by Ceramide and b-Series Complex Gangliosides," *The Journal of Biological Chemistry*, 276:44396-44404.
Bieberich, et al., 1999, "Differential Effects of Glycolipid Biosynthesis Inhibitors on Ceramide-Induced Cell Death in Neuroblastoma Cells," *Journal of Neurochemistry*, 72:1040-1049.
Blaschke, et al., 1998, "Programmed Cell Death is a Universal Feature of Embryonic and Postnatal Neuroproliferative Regions throughout the Central Nervous System," *The Journal of Comparative Neurology*, 396:39-50.
Blaschke, et al., 1996, "Widespread Programmed Cell Death in Proliferative and Postmitotic Regions of the Fetal Cerebral Cortex," *Development*, 122:1165-1174.
Brugg, et al., 1996, "Ceramide Induces Apoptosis in Cultured Mesencephalic Neurons," *Journal of Neurochemistry*, 66:733-739.
Brustle, et al., 1997, "In Vitro-Generated Neural Precursors Participate in Mammalian Brain Development", *Proc. Natl. Acad. Sci. USA*, 94:14809-14814.
Carpenter, et al., 2001, "Enrichment of Neurons and Neural Precursors from Human Embryonic Stem Cells", *Exper. Neuro.*, 172:383-397.

(Continued)

*Primary Examiner*—David S Romeo
*Assistant Examiner*—Daniel C Gamett
(74) *Attorney, Agent, or Firm*—Sutherland Asbill & Brennan LLP

(57) ABSTRACT

The present invention provides compositions and methods for human neural cell production. More particularly, the present invention provides cellular differentiation methods employing amphiphilic lipid compounds, preferably ceramide analogs of the β-hydroxyalkylamine type and optionally employing an essentially serum free MEDII conditioned medium for the generation of human neural cells from pluripotent human cells. The methods alternatively comprise modulating apoptosis by modifying the levels of PAR-4, with or without the presence of amphiphilic lipid compounds and optionally employing MEDII conditioned medium. The methods alternatively encompass modulating apoptosis by modulating the intracellular concentration of endogenous lipid second messengers, such as ceramide.

20 Claims, 16 Drawing Sheets

OTHER PUBLICATIONS

Casaccia-Bonnefil, et al., 1996, "Death of Oligodendrocytes Mediated by the Interaction of Nerve Growth Factor with its Receptor p75," *Nature*, 383:716-719.

Chun, Jerold, 2000, "Cell Death, DNA Breaks and Possible Rearrangements: An Alternative View," *Trends in Neuroscience*, 23:407-408.

Decraene, et al., 2002, "Identification of Genes Involved in Ceramide-Dependent Neuronal Apoptosis using cDNA Arrays," *Genome Biol.*, 3(8)research 0042.1-0042.22.

Esdar, et al., 2002, "Differentiation-Associated Apoptosis of Neural Stem Cells is Effected by Bcl-2 Overexpression: Impact on Cell Lineage Determination", Eur. J. Cell Biol., 80:539-553.

Fraichard, et al., 1995, "In Vitro Differentiation of Embryonic Stem Cells into Glial Cells and Functional Neurons", *J. Cell Sci.*, 108:3181-3188.

Furuya, et al., 1998, "Ceramide and Its Interconvertible Metabolite Sphingosine Function as Indispensable Lipid Factors Involved in Survival and Dendritic Differentiation of Cerebellar Purkinje Cells," *Journal of Neurochemistry*, 71:366-377.

Hartfield, et al., 1997, "Ceramide Induces Apoptosis in PC12 cells," *FEBS Letters*, 401:148-152.

Herget, et al., 2000, Production of Ceramides Causes Apoptosis During Early Neural Differentiation in Vitro, *The Journal of Biological Chemistry*, 275:30344-30354.

Irie, et al., 1998, "Application of Exogenous Ceramide to Cultured Rat Spinal Motoneurons Promotes Survival or Death by Regulation of Apoptosis Depending on its Concentrations," *Journal of Neuroscience Research*, 54:475-485.

Ito, et al., 1995, "Ceramide Prevents Neuronal Programmed Cell Death Induced by Nerve Growth Factor Deprivation," *Journal of Neurochemistry*, 65:463-466.

Jaffrezou, et al., 1998, "Positive Feedback Control of Neural Sphingomyelinase Activity by Ceramide," *FASEB*, 12:999-1006.

Kawasaki, et al., 2002, "Generation of Dopaminergic Neurons and Pigmented Epithelia from Primate ES Cells by Stromal Cell-Derived Inducing Activity", *Proc. Natl. Acad. Sci. USA*, 99(3):1580-1585.

Kawasaki, et al., 2000, "Induction of Midbrain Dopaminergic Neurons from ES Cells by Stromal Cell-Derived Inducing Activity", *Neuron*, 28:31-40.

Kim, et al., 2002, "Dopamine Neurons Derived from Embryonic Stem Cells Function in an Animal Model of Parkinson's Disease", *Nature* 418:50-56.

Li, et al., 1998, "Generation of Purified Neural Precursors from Embryonic Stem Cells by Lineage Selection", *Current Biol.* 8:971-974.

Liu, et al., 2000, "Hypoxic Preconditioning Protects Cultured Neurons against Hypoxic stress via TNF-α and Ceramide," *Am. J. Physiol. Cell Physiol.*, 278:C144-C153.

Obeid, et al., 1993, "Programmed Cell Death Induced by Ceramide," *Science*, 259:1769-1771.

Okabe, et al., 1996, "Development of Neuronal Precursor Cells and Functional Postmitotic Neurons from Embryonic Stem Cells in Vitro", *Mech. Dev.* 59:89-102.

O'Shea, 2002, "Neuronal Differentiation of Embryonic Stem Cells", *Meth. In Mol. Biol.* 198:3-14.

Renoncourt, et al., 1998, "Neurons Derived in Vitro from ES Cells Express Homeoproteins Characteristic of Motoneurons and Interneurons", *Mech. Dev.* 79:185-197.

Reubinoff, et al., 2001, "Neural Progenitors from Human Embryonic Stem Cells", *Nature Biotech* 19(12):1134-1140.

Schuldiner, et al., 2001, "Induced Neuronal Differentiation of Human Embryonic Stem Cells", *Brian Res.* 913-201-205.

Strubing, et al., 1995, "Differentiation of Pluripotent Embryonic Stem Cells into the Neuronal Lineage in Vitro Gives Rise to Mature Inhibitory and Excitatory Neurons", *Mech. Dev.* 53:275-287.

Toman, et al., 2002, "Ceramide-Induced Cell Death in Primary Neuronal Cultures: Upregulation of Ceramide Levels During Neuronal Apoptosis," *Journal of Neuroscience Research*, 68:323-330.

Tropepe, et al., 2001, "Direct Neural Fate Specification from Embryonic Stem Cells: A Primitive Mammalian Neural Stem Cell Stage Acquired through a Default Mechanism", *Neuron*, 30:65-78.

Zhang, et al., 2001, "In Vitro Differentiation of Transplantable Neural Precursors from Human Embryonic Stem Cells", *Nature Biotech.* 19(12):1129-1133.

* cited by examiner

| | TUNEL | PAR-4 | Ceramide | Nestin | PCNA |
|---|---|---|---|---|---|
| TUNEL | - | 59 | 60 | 5 | 48 |
| PAR-4 | 59 | - | 62 | 11 | n.d. |
| Ceramide | 60 | 62 | - | n.d. | n.d. |
| Nestin | 5 | 11 | n.d. | - | 51 |
| PCNA | 48 | n.d. | n.d. | 51 | - |

Total cell count: 200

A  B

Untreated stem cells  S18-treated stem cells

Injection of untreated EB8-derived embryonic stem cells

A     B     C     D

Injection site     Migration site

Phase contrast    Vybrant dil    Phase contrast    Vybrant dil

Injection of S18-treated EB8-derived embryonic stem cells

E     F     G     H

Injection site     Migration site

Phase contrast    Vybrant dil    Phase contrast    Vybrant dil

A

B

EB8  NP2  D1  D4

Oct4

Vimentin

Nestin

GFAP

MAP-2

Synaptophysin 1    2    3    4

|         | TUNEL+   | % of TUNEL+ | TUNEL-   | % of TUNEL- | Total    | % of total |
|---------|----------|-------------|----------|-------------|----------|------------|
|         | 63+/-4   |             | 137+/-11 |             | 200      |            |
| PAR-4   | 59+/-6   | 94%         | 31+/-3   | 27%         | 90+/-9   | 45%        |
| Nestin  | 5+/-2    | 8%          | 107+/-6  | 78%         | 112+/-10 | 56%        |
| PCNA    | 47+/-5   | 75%         | 61+/-5   | 45%         | 108+/-9  | 54%        |
| Ceramide| 61+/-6   | 98%         | 46+/-4   | 34%         | 107+/-9  | 54%        |

| Marker | | Counts | % of total counts (n=200) | % expected if independent |
|--------|--|--------|---------------------------|---------------------------|
| A | B |        | A + B                     | f(A+B) = f(A)xf(B)        |
| PAR-4 + Nestin | | 12+/-4 | 6 | 25 |
| PAR-4 + Ceramide | | 62+/-7 | 31 | 24 |
| PCNA + Nestin | | 50+/-7 | 25 | 30 |

```
                               SEQUENCE LISTING

<160> NUMBER OF SEQ ID NOS: 16

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Gly Pro Arg Pro
  1

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Gly Pro Gly Gly
  1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Val Ala Pro Gly
  1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
```

-continued

```
<400> SEQUENCE: 4

Arg Pro Lys Pro
  1

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Pro Lys Pro Gln Gln Phe Phe Gly Leu Met
  1               5                  10

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 6
ccagcgccag gaaaggcaaa g                                           21

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7
ctaccttgtc agctgcccaa caac                                        24

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
agccacgccg tttggaaagg                                             20

<210> SEQ ID NO 9
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 9
acactttatt cctcagggca ttacacg                                     27

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
gctaacatgg agaatgcact c                                           21
```

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 11
cttcctccgt ctgctccac                                              19

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 12
gaaggtgaag gtcggagtca acg                                         23

<210> SEQ ID NO 13
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 13
ggtgatggga tttccattga tgacaagc                                    28

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 14
atggcgaccg gcggctatcg                                             20

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 15
ctaccttgtc agctgcccaa caac                                        24

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      antisense oligonucleotide

<400> SEQUENCE: 16
cgatagccgc cggtcgccat gttcc                                       25

US 7,445,931 B2

COMPOSITIONS AND METHODS FOR ENRICHMENT OF NEURAL STEM CELLS USING CERAMIDE ANALOGS

CROSS REFERENCE TO RELATED APPLICATIONS

This application is a national phase application of PCT/US03/30112, filed Sep. 25, 2003, which claims priority to U.S. Provisional Patent Application No. 60/413,510 filed on 25 Sep. 2002, and to U.S. Provisional Patent Application No. 60/485,351 filed on Jul. 7, 2003.

ACKNOWLEDGMENT OF FEDERAL RESEARCH SUPPORT

This invention was made, at least in part, with funding from the National Institutes of Health (Award Number MH064794 to BGC, MH61934-04 and 1R01 NS046835-01 to EB). Accordingly, the United States Government has certain rights in this invention.

BACKGROUND OF THE INVENTION

1. Field of the Invention

This invention relates generally to mammalian stem cells and to differentiated or partially differentiated cells derived therefrom using amphiphilic lipid compounds, and preferably, using novel ceramide analogs of the β-hydroxyalkylamine type. The present invention also relates to methods of producing, differentiating and culturing the cells of the invention, and to uses thereof. The methods alternatively comprise modulating the levels of apoptotic regulating factors, such as PAR-4, and/or modulating the intracellular concentration of endogenous lipid second messengers, such as ceramide. These further methods can optionally be performed in the presence of amphiphilic lipid compounds, and optionally employ MEDII conditioned medium. The invention further relates to compositions comprising the amphiphilic lipid analogs and MEDII conditioned medium.

2. Background Art

Embryonic stem (ES) cells represent a powerful model system for the investigation of mechanisms underlying pluripotent cell biology and differentiation within the early embryo, as well as providing opportunities for genetic manipulation of mammals and resultant commercial, medical and agricultural applications. Furthermore, appropriate proliferation and differentiation of ES cells can be used to generate an unlimited source of cells suited to transplantation for treatment of diseases that result from cell damage or dysfunction. Other pluripotent cells and cell lines including early primitive ectoderm-like (EPL) cells as described in International Patent Application WO 99/53021, in vivo or in vitro derived ICM/epiblast, in vivo or in vitro derived primitive ectoderm, primordial germ cells (EG cells), teratocarcinoma cells (EC cells), and pluripotent cells derived by dedifferentiation, reprogramming or by nuclear transfer will share some or all of these properties and applications.

Human ES cells have been described in International Patent Application WO 96/23362, and in U.S. Pat. Nos. 5,843,780, and 6,200,806; and human EG cells have been described in International Patent Application WO 98/43679, and U.S. Pat. No. 6,245,566.

The ability to tightly control differentiation or form homogeneous populations of partially differentiated or terminally differentiated cells by differentiation in vitro of pluripotent cells has proved problematic. Most current approaches involve the formation of embryoid bodies from pluripotent cells in a manner that is not controlled and does not result in homogeneous populations. Mixed cell populations such as those in embryoid bodies of this type are generally unlikely to be suitable for therapeutic or commercial use.

Uncontrolled differentiation produces mixtures of pluripotent stem cells and partially differentiated stem/progenitor cells corresponding to various cell lineages. When these ES-derived cell mixtures are grafted into a recipient tissue the contaminating pluripotent stem cells proliferate and differentiate to form tumors, while the partially differentiated stem and progenitor cells can further differentiate to form a mixture of inappropriate and undesired cell types. It is well known from studies in animal models that tumors originating from contaminating pluripotent cells can cause catastrophic tissue damage and death. In addition, pluripotent cells contaminating a cell transplant can generate various inappropriate stem cell, progenitor cell and differentiated cell types in the donor without forming a tumor. These contaminating cell types can lead to the formation of inappropriate tissues within a cell transplant. These outcomes cannot be tolerated for clinical applications in humans. Therefore, uncontrolled ES cell differentiation makes the clinical use of ES-derived cells in human cell therapies impossible.

Selection procedures have been used to obtain cell populations enriched in neural cells from embryoid bodies. These include genetic modification of ES cells to allow selection of neural cells by antibiotic resistance (Li et al., 1998 Current Biol., 8:971-974), and manipulation of culture conditions to select for neural cells (Okabe et al., 1996 Mech., Dev. 59:89-102; and Tropepe et al., 2001 Neuron, 30:65-78; O'Shea, 2002 Meth in Mol., Biol. 198:3-14). Previously, one research group has demonstrated efficient differentiation of mouse and primate ES cells to TH+ neurons following co-culture with the PA6 stromal cell line, but this technique is not likely to be useful for cell therapy applications as it introduces xenograft issues associated with exposure to non-human cell lines and removal of potential PA6 cell contamination in subsequent cultures (Kawasaki et al., 2000 Neuron, 28:31-40; Kawasaki et al., 2002 Proc. Natl. Acad. Sci. USA, 99(3):1580-1585). Furthermore, the PA6 differentiation procedure generated non-neural terminally differentiated cell types, such as retinal epithelial cells, reducing the usefulness of the cell cultures for cell therapy. In addition, McKay has demonstrated efficient differentiation of mouse ES cells to TH+ neurons, but this differentiation required over-expression of the Nurr-1 transcription factor in combination with exposure to Sonic Hedgehog and FGF8 (Kim et al., 2002 Nature 418(6893):50-6). Furthermore, the McKay protocol involves a complex, five stage differentiation method for differentiation of mouse ES cells to neurons.

In all of these procedures, the differentiation of pluripotent cells in vitro does not involve biological molecules that direct differentiation in a controlled manner. Similarly, in experiments examining neural differentiation from human ES cells, there is no way to control the neural differentiation, and the methods merely allow for the passive development of neural cell types (see Zhang et al., 2001 Nature Biotech, 19(12): 1129-1133, and Reubinoff et al., 2001 Nature Biotech, 19(12):1134-40). Hence homogeneous, synchronous populations of neural cells with unrestricted neural differentiation capability are not produced, restricting the ability to derive essentially homogeneous populations of partially differentiated or differentiated neural cells. Another research group differentiated human ES cell derived embryoid bodies in 20% serum containing medium for 4 days followed by plating and selection/expansion of neural cell types in medium containing B27 and N2 supplements (serum free), EGF, FGF-2, PDGF-AA, and IGF-1 (Carpenter et al., 2001 Exper. Neuro., 172:383-397). Carpenter et al. showed that neural progenitors could be enriched from this culture system by cell sorting or immunopanning using antibodies directed against polysialated NCAM or the cell surface molecule recognized by the A2B5 monoclonal antibody.

Chemical inducers such as retinoic acid have also been used to form neural lineages from a variety of pluripotent cells including ES cells (Bain et al., 1995 Dev. Biol., 168: 342-357, Strubing et al., 1995 Mech. Dev., 53:275-287, Fraichard et al., 1995 J. Cell Sci., 108:3181-3188, Schuldhrer et al., 2001 Brain Res., 913:201-205; Esdar et al., 2001 Eur. J. Cell Biol., 80:539-553). However, the route of retinoic acid-induced neural differentiation has not been well characterized, and the repertoire of neural cell types produced appears to be generally restricted to ventral somatic motor, branchiomotor or visceromotor neurons (Renoncourt et al., 1998 Mech. Dev., 79:185-197).

Previous publications report the transplantation of ES-derived neural cells into the ventricles of the fetal or newborn rat or mouse brain without the formation of tumors (Brustle et al., 1997 PNAS, 94:14809-14814, Zhang et al., 2001 Nature Biotech, 19:1129-1133). Although some of the cells in these studies do integrate into the host brain, many of the cells in the transplants form neural tube like structures within the lumen of the brain ventricle. Therefore, these previous studies do not lead to methods that can be readily applied to human cell therapy. Note that Reubinoff et al. (2001 Nature Biotech, 19:1134) also injected ES-derived neural cells into the ventricles of newborn mice but did not report intraventricular masses of neural cells, omitting any mention of the presence or absence of such masses.

Neural stem cells and precursor cells have been derived from fetal brain and adult primary central nervous system tissue in a number of species, including rodent and human (e.g., see U.S. Pat. No. 5,753,506 (Johe), U.S. Pat. No. 5,766,948 (Gage), U.S. Pat. No. 5,589,376 (Anderson and Stemple), U.S. Pat. No. 5,851,832 (Weiss et al.), U.S. Pat. No. 5,958,767 (Snyder et al.) and U.S. Pat. No. 5,968,829 (Carpenter). However, each of these disclosures fails to describe a predominantly homogeneous population of neural stem cells able to differentiate into all neural cell types of the central and peripheral nervous systems, and/or essentially homogeneous populations of partially differentiated or terminally differentiated neural cells derived from neural stem cells by controlled differentiation. Furthermore, it is not clear whether cells derived from primary fetal or adult tissue can be expanded sufficiently to meet potential cell and gene therapy demands. Neural stem cells derived from fetal or adult brain are established and expanded after the cells have committed to the neural lineage and in some cases after the cells have committed to neural sublineages. Therefore, these cells do not provide the opportunity to manipulate the early differentiation processes that occur prior to neural commitment. Pluripotent stem cells provide access to these earliest stages of mammalian cellular differentiation opening additional options for cell expansion and directed development of the cells into desired lineages.

It has been suggested that sphingosine, ceramide and ceramide analogs can be used to induce apoptosis in certain cells; however, the results to date have been inconsistent. Ceramide has been reported to induce apoptosis in some cells or cell-lines of neural origin, while in other reports ceramide application has protected the cells from apoptosis. For example, compare Marcora et al., 1996 Found. Clin. Immunol., 4:11-13; Hartfield et al., 1997 FEBS Lett, 401:148-152; Casaccia-Bonnefil et al., 1996 Nature, 383:716-719; Brugg et al., 1996 J. Neurochem., 66:733-739 to Furuya et al., 1998 J. Neurochem., 71:366-377; Irie and Hirabayashi, 1998 J. Neurosci. Res., 54:475-485; Ito & Horigome, 1995 J. Neruochem., 65:463-466; and Liu et al., 2000 Am. J. Cell Physiol., 278: C144-153. The results achieved have been dependent on cell type, cell density, and the concentration of ceramide or the ceramide analog used (For review, see Toman et al., 2002 J. Neurosci. Res., 68:323-330). These experiments have been performed on tumor cells, immortalized cell lines, and primary cultures of differentiated cells, and the results have not been extrapolated to a culture of undifferentiated stem cells. See, Obeid et al., 1993 Science, 259:1769-1771; Marcora et al., 1996 Found. Clin. Immunol., 4:11-13; Hartfield et al., 1997 FEBS Lett, 401:148-152; Casaccia-Bonnefil et al., 1996 Nature, 383:716-719; Herget et al., 2000 J. Biol. Chem., 275:30344-30354; and U.S. Pat. No. 6,410,597 (Bieberich). It has been postulated that the effects of ceramide application may be mediated by a ceramide-activated pathway or feedback mechanism (Jaffrezou et al., 1998 FASEB J., 12:999-1006.)

The complexity of ceramide-dependent neuronal apoptosis, and the resulting lack of predictability in the prior art is demonstrated by a study showing the expression profile of 239 genes that respond to C2-ceramide treatment (Decraene et al., 2002 Genome Biol., 3(8):research 0042.1-0042.22). This study showed that C2-ceramide treatment both upregulated and downregulated pro-apoptotic genes in neuronally differentiated PC12 cells, indicating a complex and unpredictable genetic response to C2-ceramide treatment. Further, certain ceramide experiments have even shown that ceramide induces apoptosis in some differentiated neural cells (See Toman et al., 2002 J. Neurosci. Res., 68:323-330; Brugg et al., 1996 J. Neurochem., 66:733-739), suggesting that the use of ceramide may not be a suitable way to select for differentiated or partially differentiated neural cells that can differentiate into all neural cell types of the central and peripheral nervous systems.

Extensive programmed cell death/apoptosis occurs during neural differentiation in the developing mammalian central nervous system (Chun, J., 2000 Trends in Neuroscience, 23:407-408; Blaschke et al., 1996 Development, 122:1165-1174; Blaschke et al., 1998 J. Comparative Neurology, 396: 39-50). This early cell death appears to be largely confined to the neural stem cell and neural progenitor cell pools. In embryonic day 14 mouse cerebral cortex, 70% of the cells undergo apoptosis/programmed cell death (Blaschke et al., 1996 Development, 122:1165-1174). The finding that a large proportion of neural progenitor cells undergo programmed cell death suggests that neural stem/progenitor cells may be extremely responsive to inducers of apoptosis/programmed cell death such as ceramide and ceraride analogs In this context, the resistance of embryonic stem cell-derived neural progenitor/stem cells to ceramide induced or enhanced cell death would be surprising and unexpected.

In summary, it has not been possible to control the differentiation of pluripotent cells in vitro, to provide homogeneous, synchronous populations of neural cells with unrestricted neural differentiation capacity. Similarly, methods have not been developed for the derivation of neural cells from pluripotent cells in a manner that parallels their formation during embryogenesis. In addition, current methods have relied upon the expression of foreign genes to drive neural differentiation of pluripotent stem cells (Kim et al., 2002 Nature, 418:50-56). These limitations have restricted the ability to form essentially homogeneous, synchronous populations of partially differentiated and terminally differentiated neural cells in vitro, and have restricted their further development for therapeutic and commercial applications.

There is a need, therefore, to identify methods and compositions for the production of a population of cells enriched in neural stem cells and the products of their further differentiation, and in particular, human neural cells and their products.

SUMMARY OF THE INVENTION

It is an object of the present invention to overcome, or at least alleviate, one or more of the difficulties or deficiencies associated with the prior art. In that regard, the present invention provides a method of producing a human neural cell including the steps of: a) providing a pluripotent human cell; b) culturing the pluripotent human cell to form an embryoid body; and c) culturing cells from the embryoid body with a composition comprising an amphiphilic lipid compound to produce the human neural cell. The present invention also provides a method of enriching a human cell culture for neural cells including the following steps: a) providing a pluripotent human cell culture; b) culturing the pluripotent human cell culture to form an embryoid body; and c) culturing cells from the embryoid body with a composition comprising an amphiphilic lipid compound to produce a human cell culture enriched in neural cells. The invention further contemplates that the amphiphilic lipid compound is selected from the group consisting of a ceramide compound, a sphingosine compound, and a hydroxyalkyl ester compound. In a preferred embodiment, the pluripotent human cell or pluripotent human cell culture is a differentiating cell or cell culture. In certain preferred embodiments, the pluripotent human cell or cell culture is cultured with an essentially serum free medium to form an embryoid body. In a preferred embodiment, the essentially serum free medium is a MEDII conditioned medium, and/or contains proline, or a proline containing peptide.

The invention further encompasses methods for modulating apoptosis in human pluripotent cell populations comprising modifying expression of an apoptotic regulating factor, and/or modulating the intracellular concentration of endogenous lipid second messengers, such as ceramide. Preferably, the apoptotic regulating factor is PAR-4. Preferably, modulating expression of PAR-4 comprises increasing or decreasing the mRNA levels and/or the protein levels of PAR-4. Increasing expression of PAR-4 mRNA and/or protein is correlated with apoptosis, while decreasing expression of PAR-4 mRNA and/or protein is correlated with a decrease in apoptosis. PAR-4 expression can be modulated in pluripotent cell populations, or can be modulated in differentiated or partially-differentiated cell populations. Modulation of the expression of PAR-4 is optionally performed in the presence of an amphiphilic lipid compound or ceramide, and optionally can employ MEDII conditioned medium.

The amphiphilic lipid compound described herein can be preferably a ceramide analog of the hydroxyalkylamine type. In preferred embodiments, the ceramide compound is selected from the group comprising N-(2-hydroxy-1-(hydroxymethyl)ethyl)-palmitoylamide ("S16"); N-(2-hydroxy-1-(hydroxymethyl)ethyl)-oleoylamide ("S18"); and functional homologues, isomers, and pharmaceutically acceptable salts thereof. In a preferred embodiment the ceramide compound is S18. In another preferred embodiment the ceramide compound is S16.

The MEDII conditioned medium described herein can be preferably a Hep G2 conditioned medium that contains a bioactive component selected from the group consisting of a low molecular weight component; a biologically active fragment of any of the aforementioned proteins or components; and an analog of any of the aforementioned proteins or components. In a preferred embodiment, the bioactive component of the MEDII conditioned medium is proline, or a proline containing peptide. The pluripotent human cell of the present invention can be selected from, but is not limited to, a human embryonic stem cell; a human ICM/epiblast cell; an EPL cell; a human primitive ectoderm cell; a human primordial germ cell; and a human EG cell.

In other embodiments of the present invention, the methods described above further include the steps of dispersing the embryoid body to an essentially single cell suspension, and culturing the essentially single cell suspension comprising the pluripotent human cell with a composition comprising a ceramide compound until the human neural cell is produced, or the human cell culture enriched in neural cells is produced.

The invention further provides a composition comprising a culture of neural cells derived in vitro from a pluripotent human cell cultured with a composition comprising a ceramide compound. In preferred embodiments, these neural cells are capable of expressing one or more of the detectable markers for tyrosine hydroxylase (TH), vesicular monamine transporter (VMAT) dopamine transporter (DAT), and aromatic amino acid decarboxylase (AADC).

The invention further provides a method of treating a patient with a neural disease, comprising a step of administering to the patient a therapeutically effective amount of the neural cell or cell culture enriched in neural cells produced using the methods of the present invention. The present invention further provides a method for enhancing the efficiency of the transplantation of a cultured human pluripotent cell. In a preferred embodiment, the method comprises culturing a human pluripotent cell with a growth medium comprising an amphiphilic lipid compound, and transplanting the cultured human pluripotent cell into a patient. The amphiphilic lipid compound preferably can be selected from the group consisting of a ceramide compound, a sphingosine compound, and a hydroxyalkyl ester compound. In one embodiment, the ceramide compound is a ceramide analog of the hydroxyalkylamine type. In a preferred embodiment, the ceramide compound is selected from the group comprising S16, S18 and functional homologues, isomers, and pharmaceutically acceptable salts thereof.

The invention further provides compositions for promoting the maintenance, proliferation, or differentiation of a human neural cell, the composition comprising a cell culture medium comprising MEDII conditioned medium or a bioactive component thereof, and a ceramide compound. In a preferred embodiment, the ceramide compound is selected from the group comprising S16, S18 and functional homologues, isomers, and pharmaceutically acceptable salts thereof. The invention also provides for compositions comprising a cell culture medium comprising MEDII conditioned medium and an amphiphilic lipid compound selected from the group consisting of a sphingosine compound, and a hydroxyalkyl ester compound. In one preferred embodiment, the hydroxyalkyl ester compound is laurylgallate. The invention further provides for the neural cells cultured in the compositions.

C shows the chemical structure of N-(2-hydroxy-1-(hydroxymethyl)ethyl)-oleoylamide ("S18"). D shows the chemical structure of N,N-bis(2-hydroxyethyl)palmitoylamide ("B16"). E shows the chemical structure of N,N-bis(2-hydroxyethyl)oleoylamide ("B18"). F shows the chemical structure of N-tris(hydroxymethyl)methyl-palmitoylamide ("T16"). G shows the chemical structure of N-tris(hydroxymethyl)methyl-oleoylamide ("T18").

Figure 1:
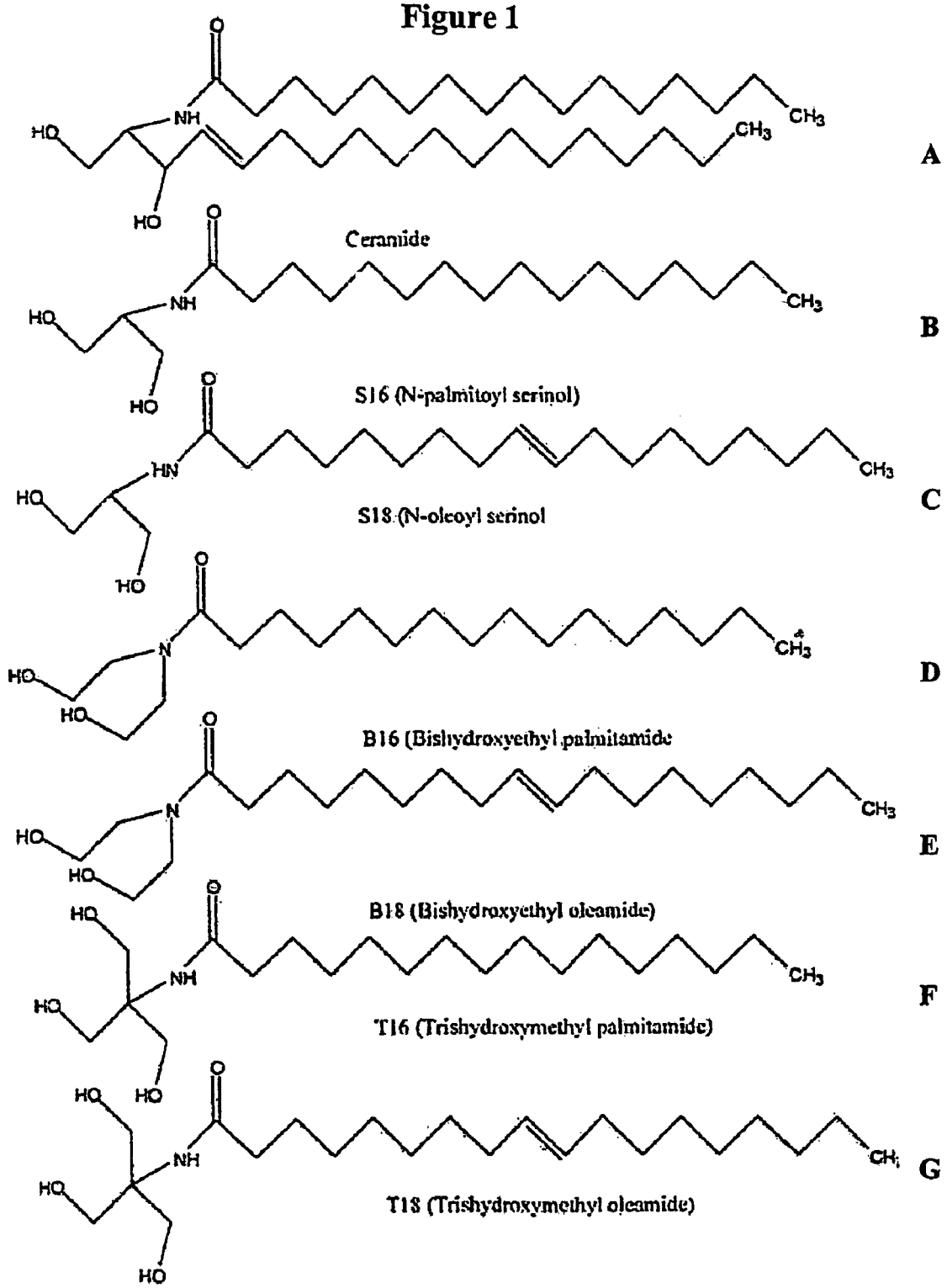
FIGS. 1A-G show the chemical structure of ceramide, and novel structural analogs of ceramide (novel ceramide analogs or NCAs) synthesized by N-acylation of β-hydroxyalkylamines. A shows the chemical structure of N-acyl sphingosine ("ceramide"). B shows the chemical structure of N-(2-hydroxy-1-hydroxymethyl)ethyl)-palmitoylamide ("S16").
Figure 2:
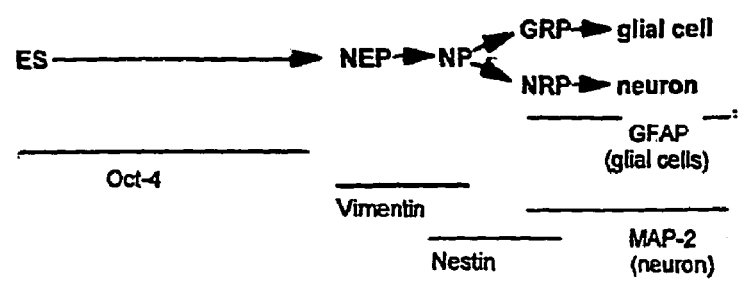

FIG. 2 is a schematic showing the in vitro neural differentiation of mouse embryonic stem cells. Abbreviations: ES (embryonic stem cell); EB (embryoid body); NP (neural progenitor cell); D (terminally differentiated cell); NEP (neuroepithelial precursor cell); GRP (glial restricted precursor cell); NRP (neuronal restricted precursor cell); LIF (leukemia inhibitory factor); DIV (days in vitro); FGF-2 (fibroblast growth factor 2); N2 (medium supplement N2); and Oct-4, GFAP, and MAP-2, are markers for differentiation proteins.

Figure 3:
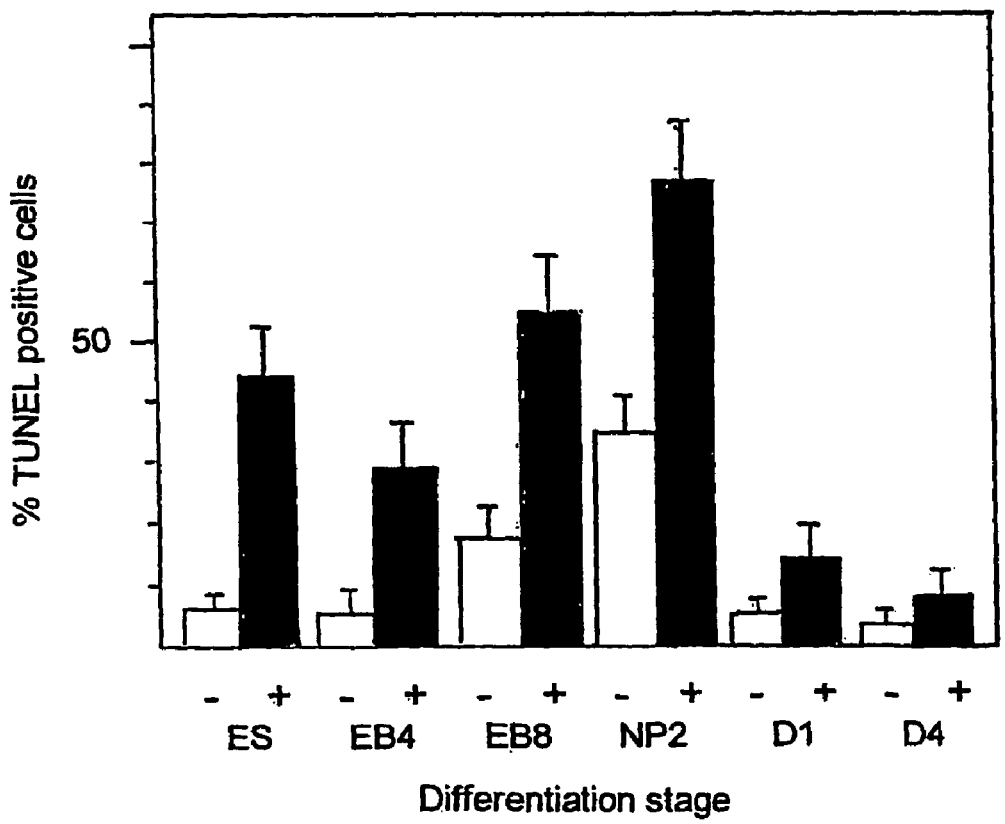

FIG. 3 shows the levels of spontaneous and induced apoptosis in differentiating ES-J1 cells. During particular stages of in vitro neural differentiation, apoptosis was induced in ES-J1 cells by incubation for 20 hours with 35 µM C2-ceramide, 75 µM S18, or 100 µM S16. Apoptosis was determined by TUNEL staining. The levels of apoptosis in ceramide treated samples was compared to the levels in control samples that were not incubated with ceramide analogs. Each experiment was performed five times. The bars show the standard mean and deviation of % TUNEL positive cells that were counted in five areas of 200 cells in each experiment. Open bars, no ceramide analog treatment; black bars, ceramide analog treatment.

FIGS. 4A-J show the cell death of ES-J1 cells treated with the novel ceramide analog S18 during in vitro neural differentiation. FIGS. 4A and B show cell death in ES cells without and with S18 incubation, respectively. FIGS. 4C and D show cell death at the EB4 stage without and with S18 incubation, respectively. FIGS. 4E and F show cell death at the EB8 stage without and with S18 incubation, respectively. FIGS. 4G and H show cell death at the NP2 stage without and with S18 incubation, respectively. FIGS. 4I and J show cell death in differentiated neurons without and with S18 incubation, respectively. ES-J1 cells were differentiated in vitro following the protocol as described herein, and were subsequently incubated for 20 hours with 75 µM of the novel ceramide analog S18. Note the high degree of cell death that was induced at the EB8 (E, and F) and NP2 stages (G, and H), whereas differentiated neurons were unaffected by ceramide treatment (compare I to J). Note also that at the EB8 stage, a rim of cells surrounding the central embryoid body survived treatment with ceramide analogs. See FIG. 2 for an explanation of the differentiation stages.

FIGS. 5A, and B show Hoechst staining and nestin antibody staining of mouse EB8 cells after incubation with S18. Differentiating embryonic stem cells at stage EB8 were incubated for 24 hours with 80 µM of S18, and were then immunostained for nestin. Apoptosis was detected by intensive staining with Hoechst dye. Note that the center of the embryoid body (left side of A) stained strongly with Hoechst 33258 and indicates apoptotic cells, whereas the rim of non-apoptotic cells in the embryoid body stained intensively for nestin (13).

Figures 5, 6:
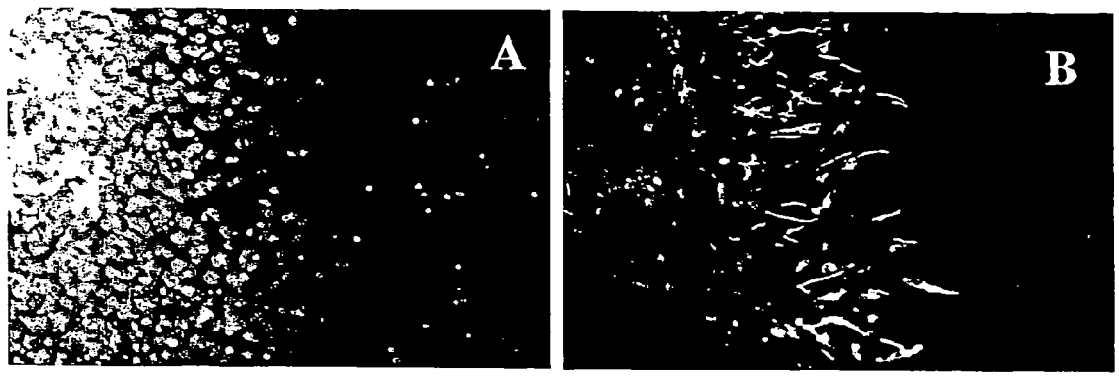

FIG. 6 shows a table summarizing double staining results for TUNEL and various marker proteins at the NP2 stage. TUNEL staining detects apoptotic cells, and the marker proteins indicate the stage of neural differentiation. The total number of cells staining for one specific antigen within a population of 200 cells was as follows: TUNEL, 65; PAR-4, 91; ceramide, 105; nestin, 113; and PCNA, 108. The table shows the number of cells that stained simultaneously for two antigens. Note that the TUNEL positive cells co-localized significantly less with nestin (8% of TUNEL positive cells were nestin positive cells while 57% of the total cell population was nestin positive cells) and that the TUNEL positive cells co-localized significantly more with PCNA (74% of TUNEL positive cells were PCNA positive cells while 54% of the total cell population was PCNA positive cells). A chi square analysis of these distributions showed that TUNEL positive cells were predominantly nestin negative and PCNA positive. The abbreviation "n.d." indicates that a particular combination was not determined.

Figure 7:
Figure 7:
Figure 8:
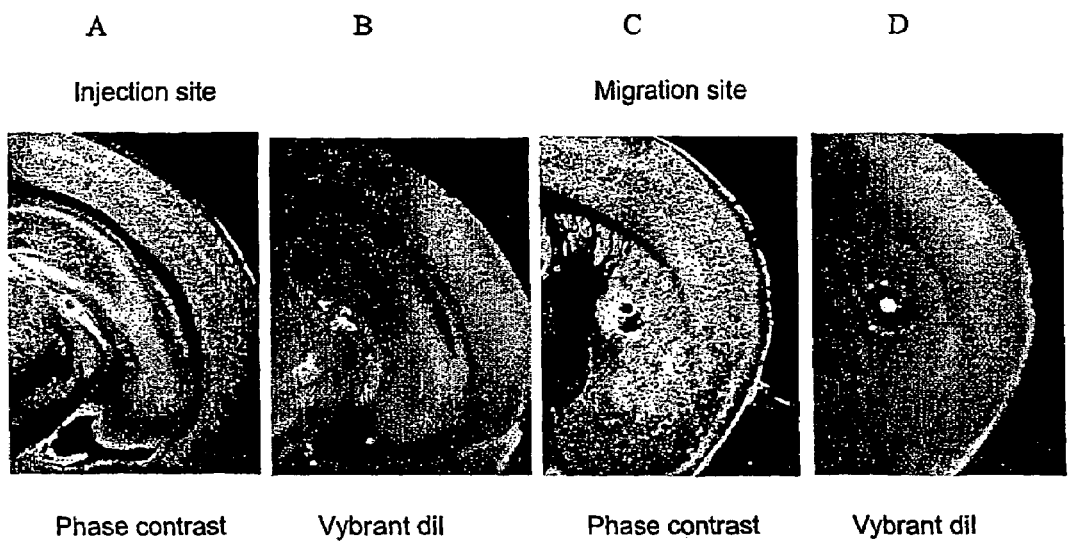
Figure 8:
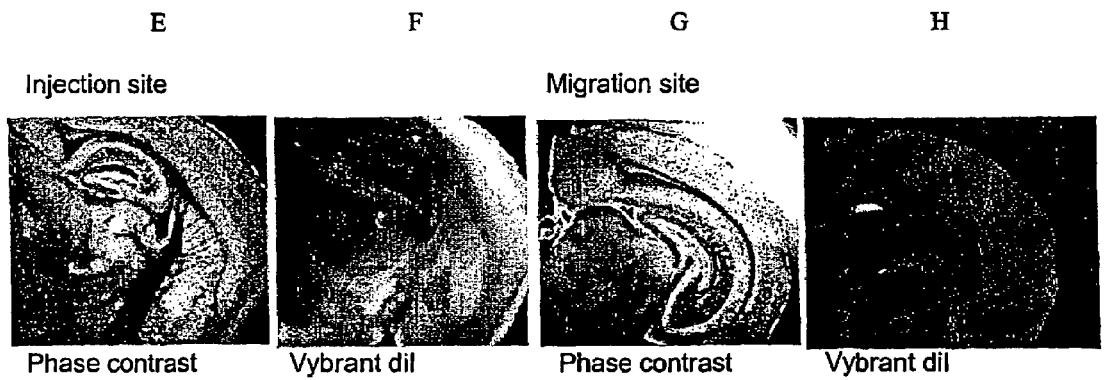

FIGS. 7A and B show that EB-derived stem cells treated with novel ceramide analogs of the serinol type do not form teratomas when injected into neonate mouse brains. Ten days after injection of the untreated ES cells (A) or treated ES cells (B), the brains were isolated for analysis. Massive teratoma formation was observed with untreated, control cells (A), while EB8-derived cells that have been treated with S18 did not show the formation of teratomas (3). The black India ink spot on the right side of the brain in panel B marks the injection channel.

FIGS. 8A-H show teratoma formation with untreated ES cells and tissue integration with S18-treated ES cells. EB8-derived stem cells were stained with a fluorescent marker dye (Vybrant diI) in order to track the migration and integration of the injected cells into the recipient's brain tissue. A and B show the injection site of untreated EB8-derived embryonic stem cells, while E and F show the injection site of S18 treated EB8-derived embryonic stem cells. C and D show the migration site of untreated EB8-derived embryonic stem cells, while G and H show the migration site of S18 treated EB8-derived embryonic stem cells. Brains injected with untreated cells show teratoma formation and displacement growth at the migration site (C and D). Only the center of the tumor is stained with Vybrant diI. In the periphery of the tumor, cells have undergone numerous cell divisions, resulting in dilution of the fluorescent dye and low levels of staining. Note the bright Vybrant diI staining of cells that have integrated into the recipient's brain tissue (G and H). This intensive staining indicates that the cells have undergone a limited number of cell divisions.

FIGS. 9A-D show expression of Oct-4 protein in HESCs and serum be embryoid bodies. A shows high levels of Oct-4 expression in a typical manually passaged HESC colony, with distinct nuclear expression in undifferentiated ES cells and no Oct-4 in the unstained feeder layer surrounding the HESC colony. B shows a typical manually passaged HESC crater colony, showing high levels of Oct-4 expression in the multilayered ring of undifferentiated cells surrounding the monolayer crater cells that express a low level of Oct-4. Differentiating cells at the edge of the colony also express a low level of Oct-4. C shows the expression of Oct-4 in a seeded essentially serum free embryoid body, representative of what is seen when sfEBMs are derived from domed HESCs or monolayer crater cells. Regions of high level Oct-4 expression persist and are indicative of residual nests of pluripotent cells maintained by local cell-cell signaling events. Neural rosettes in the same field are indicated as radially organized circles of nuclei by DAPI staining (D) and these neural precursor cells only express low levels of Oct-4.

FIGS. 10A-E show the effect of S18 treatment on seeded sfEBMs. A shows a seeded essentially serum free embryoid body exhibiting neural rosettes within the core of the explant and other cell types that have proliferated away from the rosettes. B shows that a high proportion of cells within these cultures have been killed after 36 hours exposure to 6 µM S18.

C shows that a high degree of cell death is apparent after 36 hours exposure to 8 µM S18. Neural rosettes appear to be unaffected and in many cases can be observed more clearly, as surrounding cell types have died. D is a 60× magnification of surviving neural rosette after 36 hours exposure to 8 µM S18. The rosette appears morphologically normal and the typical radial organization of cells and distinct boundary between healthy rosette cells and apoptotic surrounding cells can be observed. E shows that the dying cells are undergoing apoptosis. Apoptosis of dying cells is indicated by their fragmented nuclei when stained with DAPI. Morphologically normal nuclei of unaffected cells are present in the lower right corner.

Figure 11:
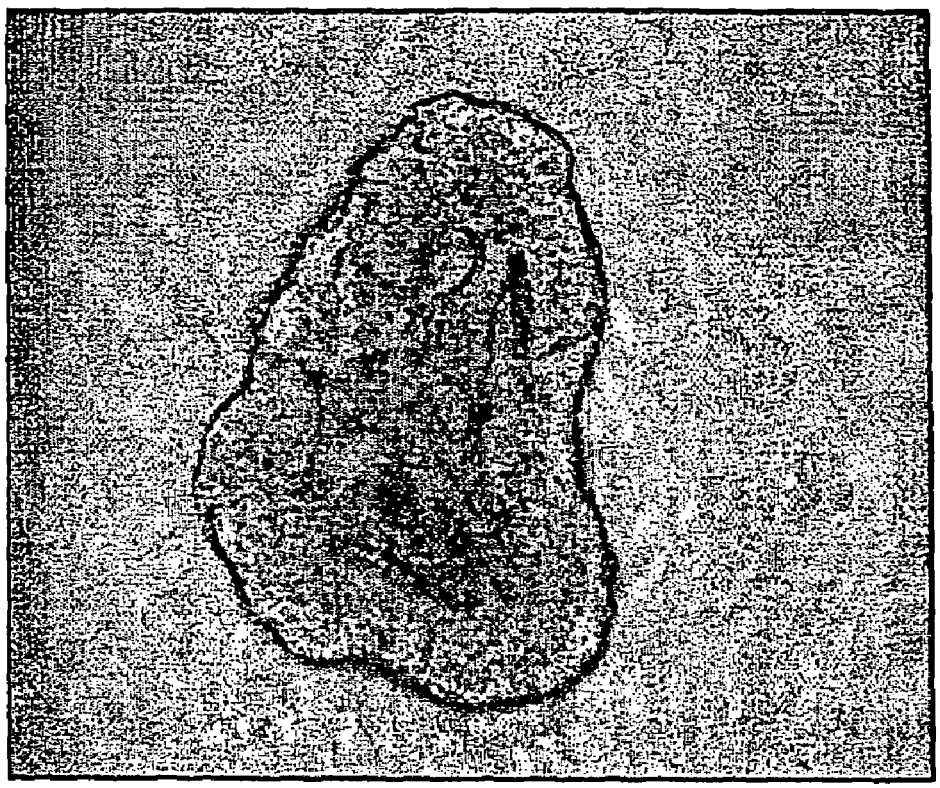
Figure 11:
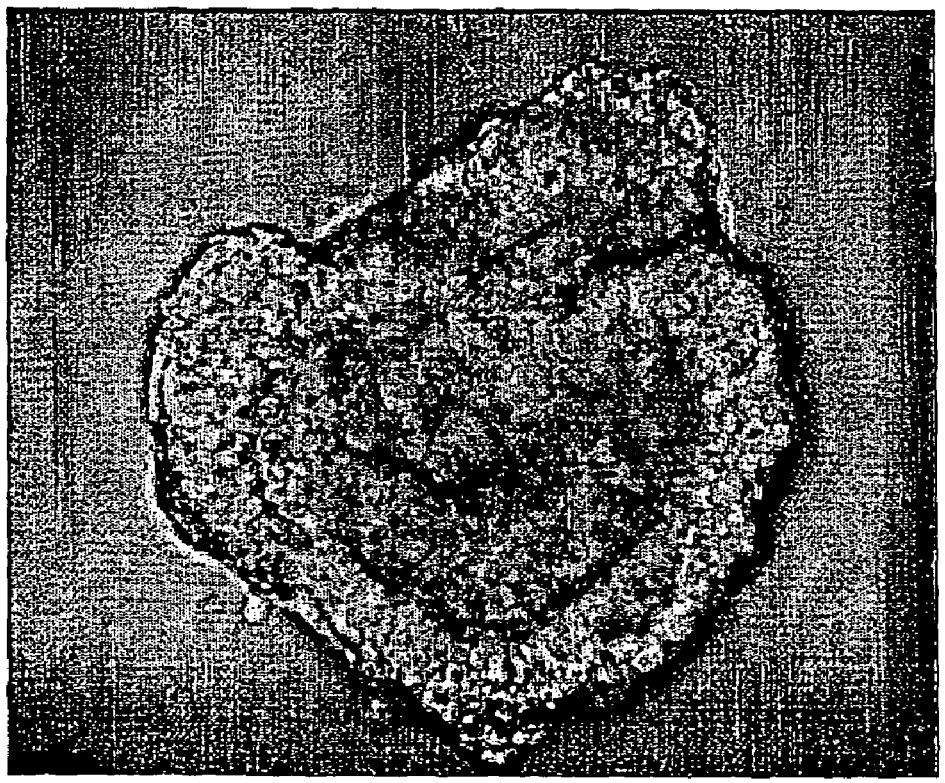

FIGS. 11A and B demonstrate the purification of neural rosette material by exposure of sfEBMs in suspension to S18. A shows S18 resistant neural rosette material isolated from generally degenerating sfEBMs grown in suspension at 20×. B shows a 40× magnification of a different piece of S18 resistant neural rosette material.

Figure 12:
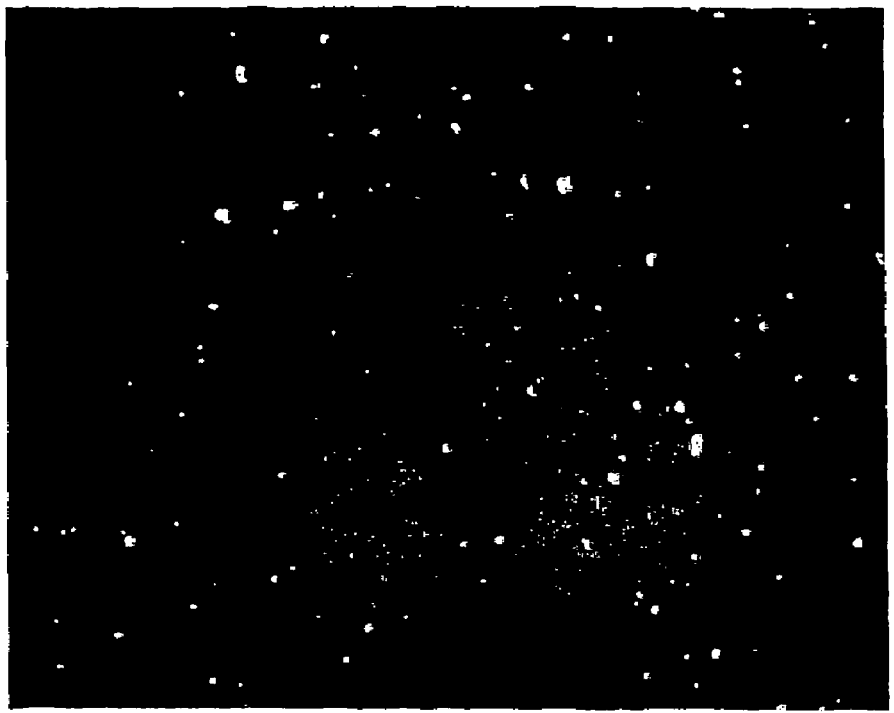
Figure 12:
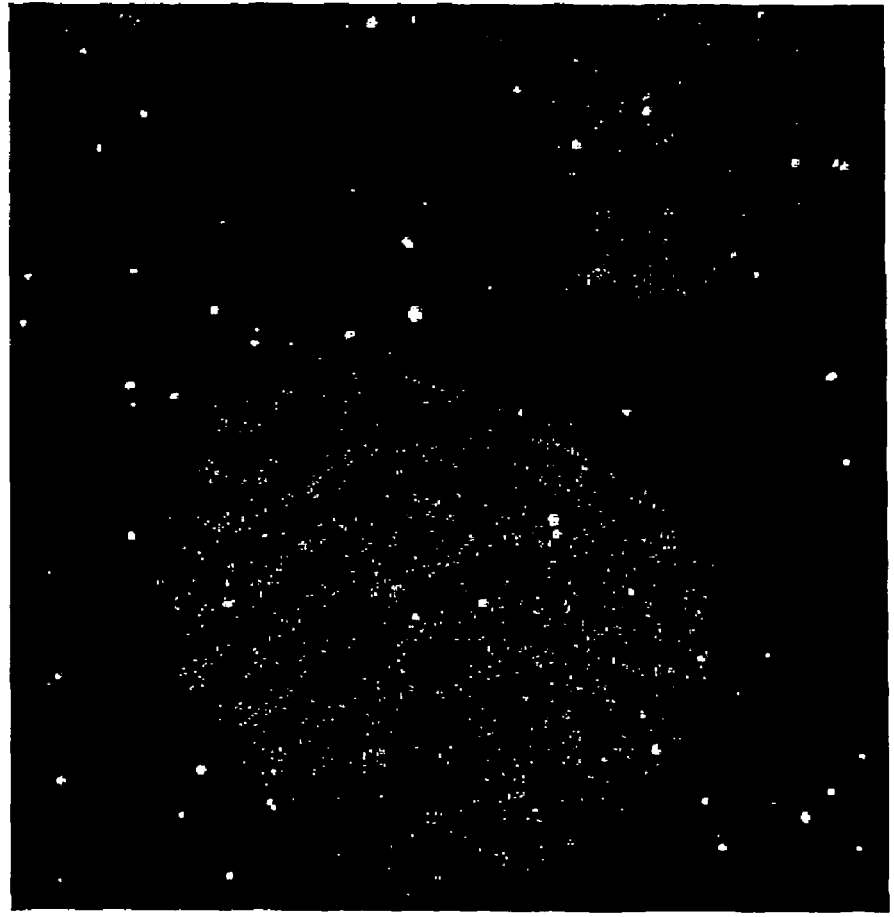

FIGS. 12A and B show the ablation of residual pluripotent cells in sfEBM cultures exposed to S18. sfEBM cultures exposed to S18 in suspension, followed by seeding and immunocytochemistry do not exhibit any cells expressing high levels of Oct-4. This demonstrated that residual nests of pluripotent cells did not survive S18 induced apoptosis.

Figure 13:
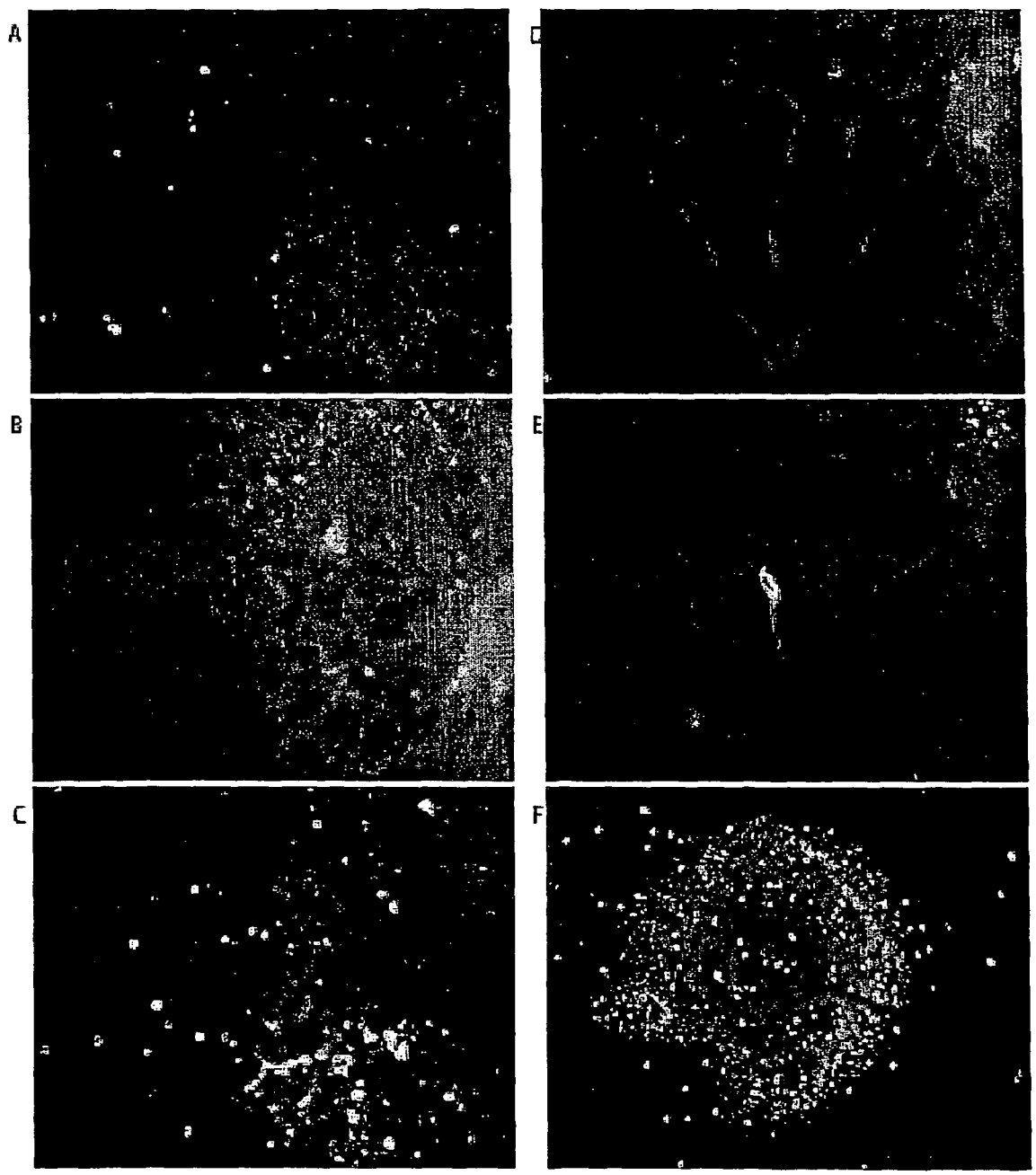

FIGS. 13A-F show that neural rosette cells are unaffected by exposure to S18. FIGS. 13A, B, and C show the same field of seeded sfEBMs stained with anti-Oct-4, anti-Map2 and anti-TH, respectively. Seeded rosette cells only express low levels of Oct-4 (A) and mature neurons (Map2+; B) are either also resistant to S18 or are regenerated effectively from the rosette precursor cells. A proportion of the Map2+ cells are presumptively dopaminergic neurons as they express Tyrosine Hydroxylase (C), indicating that they are also resistant to S18 and/or the rosette precursor cells maintain their capacity to differentiate to dopaminergic neurons. D and E show 40× magnification of Map2 and TH positive neurons in the same field, respectively. F shows that neural rosettes were still proliferative after exposure to S18, as demonstrated by phosphoHistone H3 staining for mitotic cells (indicated as the intense white spots) within DAPI stained rosettes, shown as the paler staining radially organized structures.

FIGS. 14A-D show sections of sfEBMs exposed to S18. The sfEBMs were derived from protease passaged HESCs exposed to 10 µM S18 from day 6 to 9 after derivation of the embryoid bodies. Sections were stained with DAPI to reveal rosette organization and nuclear morphology. A shows a section of an untreated sfEBM at day 9, while B-D show sections of sfEBMs at day 9 that were treated with S18 from days 6-9.

Figure 15:
Figure 15:
Figure 15:
Figure 15:
Figure 15:
Figure 15:
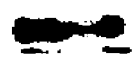

FIG. 15 shows in vitro neuronal differentiation of embryonic stem cells, overview and marker protein expression. Immunostaining for marker proteins was performed with protein extracts from stem cells at the differentiation stages shown in FIG. 2.

Figure 16:
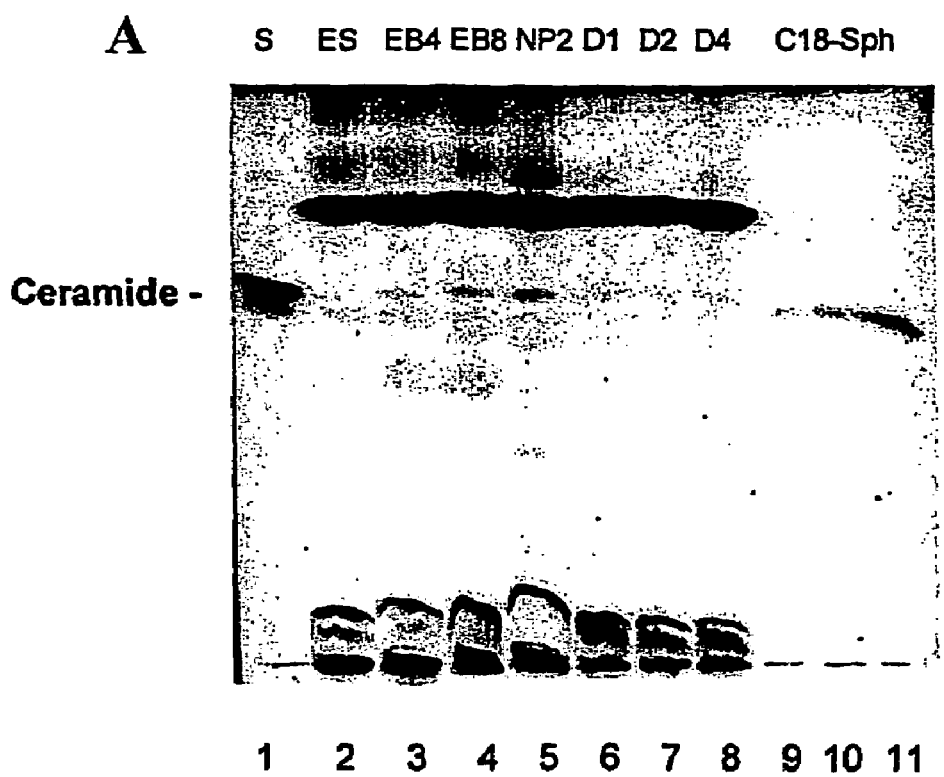
Figure 16:
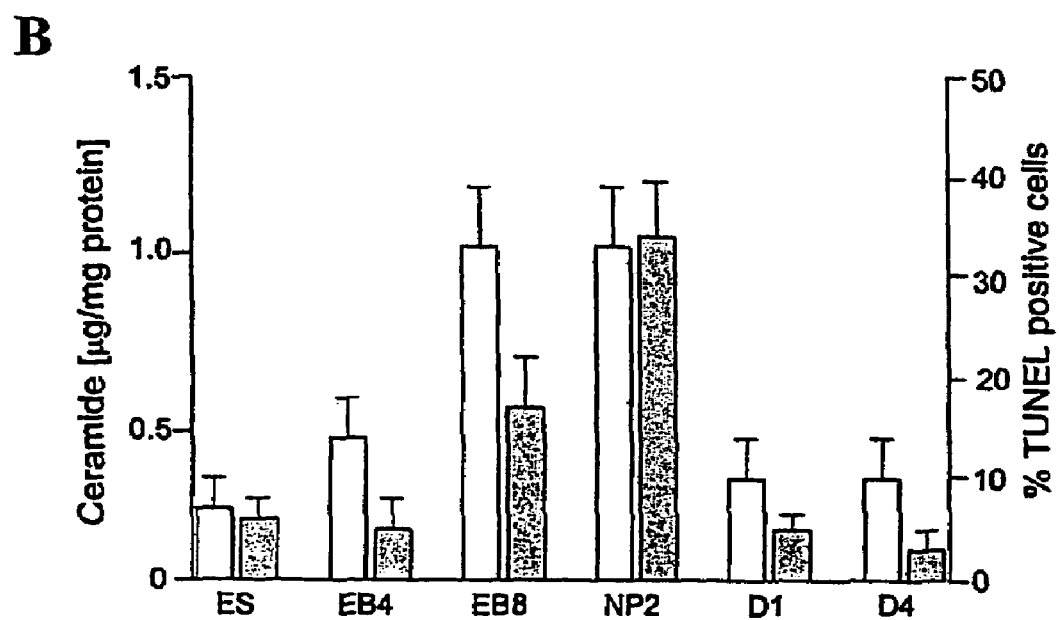

FIGS. 16A and 16B show ceramide content and apoptosis during in vitro neuronal differentiation of ES cells. In 16A, neutral lipids were purified from differentiating ES cells and a lipid amount corresponding to 750 µg of cellular protein/lane separated by HPTLC in the running solvent $CH_3Cl$/HOAc (9:1, by volume). Lipids were stained with the cupric acetate reagent. Ceramide (open bars) was quantified by densitometric analysis and comparison with known amounts of standard lipid (N-oleoyl sphingosine). Lane 1, ceramide standard from bovine brain; lane 2, fibroblast-freed ES-cells, after four days in culture; lane 3, embryoid bodies at the EB4 stage; lane 4, embryoid bodies at the EB8 stage; lane 5, neural progenitors at the NP2 stage; lanes 6-8, three terminal differentiation stages, 24 h (D1 stage), 48 h (D2 stage), and 96 h (D4 stage) upon cultivation of NPs in serum containing medium; lanes 9-11, N-oleoyl sphingosine, 250 ng, 500 ng, 1000 ng. In 16B, lipids were extracted from differentiated ES cells and the amount of ceramide quantified using the DAG kinase assay. Apoptosis (solid bars) was determined by TUNEL staining. For HPTLC, DAG kinase, and TUNEL analyses, experiments were performed with five independent ES cultures. The bars show the standard mean and deviation of % TUNEL positive cells that were counted in five areas of 200 cells in each experiment.

Figure 17:
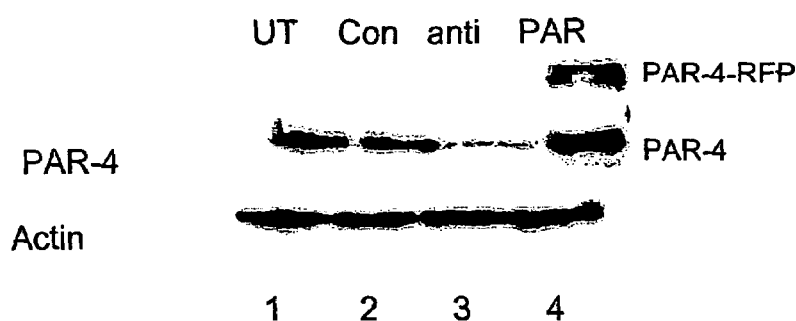

FIG. 17 shows alteration of neural stem cell apoptosis by antisense knockdown or overexpression of PAR-4. The figure shows staining of PAR-4 on immunoblots of protein from differentiating ES cells (NP3 stage) that were transfected with or without PAR-4 specific antisense oligonucleotide or PAR-4-RFP, respectively. Lane 1, untransfected NPs; lane 2, NPs transfected with standard control antisense oligonucleotide; lane 3, NPs transfected with PAR-4 specific antisense oligonucleotide; lane 4, NPs cells transfected with PAR-4-RFP.

Figure 18:
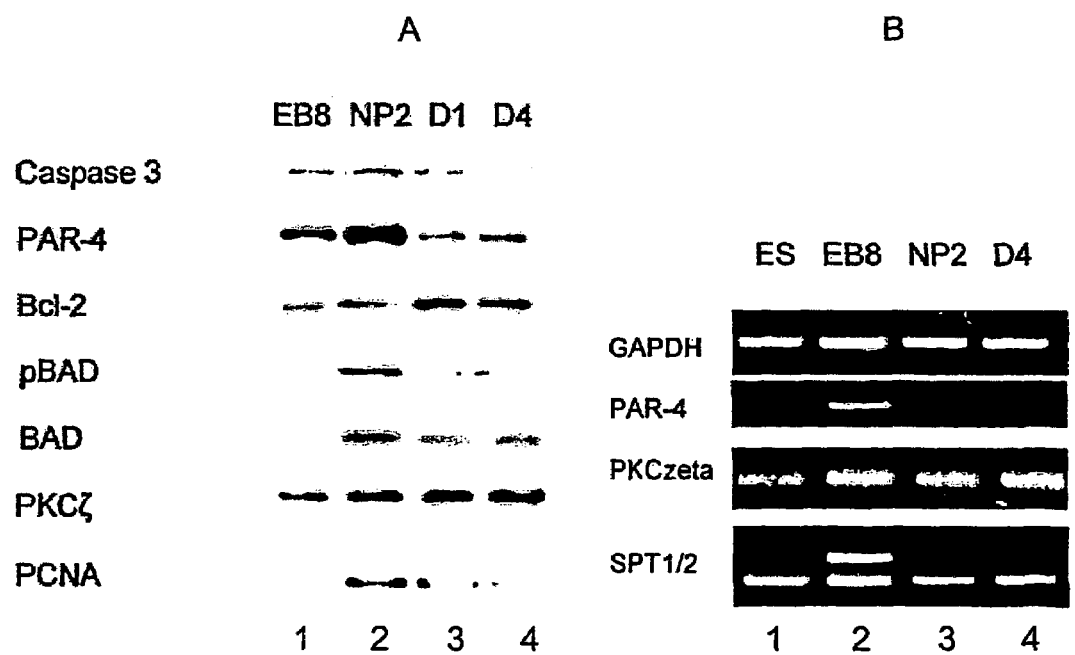

FIGS. 18A and 18B show expression of differentiation markers and pro- or anti-apoptotic proteins in differentiating embryonic stem cells. In FIG. 18 A, during in vitro neural differentiation of ES-J1 mouse embryonic stem cells, protein was extracted from the cells, separated by SDS-PAGE, and blotted onto nitrocellulose. Each lane shows the immunostaining corresponding to 35 µg of cell protein. See FIG. 2 for definition of differentiation stages. The protein analysis was performed with five independent differentiation experiments. In FIG. 18B, RNA was isolated from differentiating ES-J1 cells and subjected to RT-PCR. SPT1/2, serine palmitoyltransferase subunit 1 and 2. Each experiment was repeated four tines.

Figures 19, 20, 21:
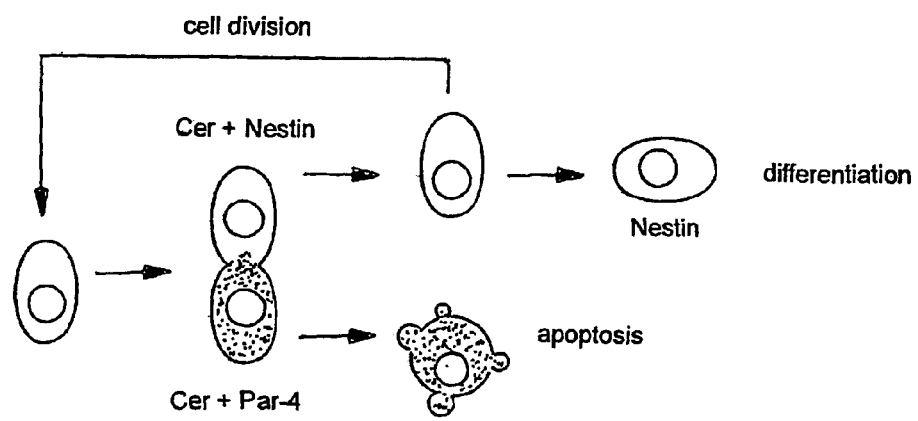

FIG. 19 shows correlation of TUNEL and expression of protein markers in individual cells at the NP2 stage. Cells at the NP2 stage were grown on coverslips and fixed. TUNEL staining (green fluorescence) was followed by indirect immunofluroescence staining using secondary antibodies that were linked to Cy3/Alexa 546 (red fluorescence) or Cy5 (far red). For species of primary antibodies see Materials and Methods. Hoechst staining was used for the identification of individual cells. FIG. 19 shows the number of cells (total cell count of 200 in five independent areas) that were TUNEL positive (average of 63+/−4) or negative (average of 137+/−11) and stained for another marker as indicated (percentage of TUNEL positive or negative is given in brackets). FIG. 19 shows standard means and variation for five areas with 200 cells from three independent experiments.

FIG. 20 shows double-staining experiments for two markers as indicated (A+B represents cells that are double-stained for A and B). The percentage of cells in the last column has been calculated from the frequency of each marker (A or B) in the total population of cells as described in the section Statistical Analysis. FIG. 20 shows standard means and variation for five areas with 200 cells from three independent experiments.

FIG. 21 shows a model for asymmetric apoptosis of neural progenitor daughter cells due to the asymmetric distribution of nestin and PAR-4 proteins. Prior to mitosis or during S-phase, neural progenitor cells up-regulate the expression of nestin, PAR-4, and ceramide. During cell division, ceramide is distributed equally to the daughter cells, whereas PAR-4 and nestin are restricted to different daughter cells. The daughter cell with simultaneous presence of PAR-4 and ceramide will die due to apoptosis, whereas the one containing ceramide and nestin will again divide or differentiate. Conversion of ceramide to sphingomyelin and/or glycoshingolipids due to upregulation of sphingomyelin or glucosyl- or galactosylceramide biosynthesis protects this cell from apoptosis upon further cell division or differentiation.

DETAILED DESCRIPTION OF THE INVENTION

Applicant has demonstrated that culturing human cell populations comprising pluripotent human cells with a composition comprising an amphiphilic lipid compound results in the formation of a human neural cell type with greater homogeneity than observed in a pluripotent human cell population that is not cultured with an amphiphilic lipid compound. The invention provides that, alternatively, the human cell population cultured with the amphiphilic lipid compound is enriched in human neural cells. In preferred embodiments, the human cell population cultured with the amphiphilic lipid compound is a differentiating human cell population. In preferred embodiments, the amphiphilic lipid compound is selected from the group comprising a ceramide compound, a sphingosine compound, and a hydroxyalkyl ester compound. In a preferred embodiment, the composition comprises a ceramide compound of the β-hydroxyalkylamine type. The invention further provides a partially differentiated cell by culturing pluripotent cells with the ceramide compound.

The invention further encompasses methods for modulating apoptosis in human pluripotent cell populations comprising modifying expression of an apoptotic regulating factor, and/or modulating the intracellular concentration of endogenous lipid second messengers, such as ceramide. Preferably, the apoptotic regulating factor is PAR-4. Preferably, modulating expression of PAR-4 comprises increasing or decreasing the mRNA levels and/or the protein levels of PAR-4. Increasing expression of PAR-4 mRNA and/or protein is correlated with apoptosis, while decreasing expression of PAR-4 mRNA and/or protein is correlated with a decrease in apoptosis. PAR-4 expression can be modulated in pluripotent cell populations, or can be modulated in differentiated or partially-differentiated cell populations. These methods can optionally be combined with the other methods and compositions described herein. Modulating the expression of PAR-4 is optionally in the presence of an amphiphilic lipid compound or ceramide, and optionally the method employs MEDII conditioned medium. Alternatively, apoptosis is modulated through increasing or decreasing the levels of endogenous lipid second messengers, such as ceramide. Levels of endogenous second messengers can be modulated using compounds and methods well known to those of skill in the art, including, but not limited to treatment with retinoic acid, the use of anti-cancer drugs such as daunomycin, and serum deprivation.

In one embodiment, the neural cell produced by culturing the pluripotent human cell with a ceramide compound is therapeutically transplanted into the brain of a subject. The cell culture of the present invention form teratomas at a greatly reduced frequency than if the culture was not treated with the ceramide compound. In a preferred embodiment, the cell culture of the present invention does not induce the formation of teratomas at a significant rate.

The present invention particularly provides a method of producing a human neural cell that includes the steps of: a) providing a pluripotent human cell; and b) culturing the pluripotent human cell with a composition comprising a ceramide compound to produce a human neural cell. The present invention additionally provides a method of enriching a human cell culture for neural cells comprising the steps of a) providing a pluripotent human cell culture; and b) culturing the pluripotent human cell culture with a composition comprising a ceramide compound to produce a human cell culture enriched in neural cells. In a preferred embodiment, the pluripotent human cell or cell culture is a differentiating pluripotent human cell or cell culture.

Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, 5th ed, Berlin: Springer-Verlag; in Current Protocols in Molecular Biology, F. M. Ausubel et al., eds., *Current Protocols*, a joint venture between Greene Publishing Associates, Inc. and John Wiley & Sons, Inc., (1998 Supplement); in Current Protocols in Cell Biology, J. S. Bonifacino et al., eds., *Current Protocols*, John Wiley & Sons, Inc. (1999 Supplement); and in Current Protocols in Neuroscience, J. Crawley et al., eds., *Current Protocols*, John Wiley & Sons, Inc. (1999 Supplement). It is to be understood that as used in the specification and in the claims, "a" or "an" can mean one or more, depending upon the context in which it is used. Thus, for example, reference to "a cell" can mean that at least one cell can be utilized.

The present invention contemplates the use of a composition comprising an amphiphilic lipid compound. In a preferred embodiment, the amphiphilic lipid compound is selected from the group consisting of a ceramide compound, a sphingosine compound, and a hydroxyalkyl ester compound.

In a preferred embodiment, the amphiphilic lipid compound is a ceramide compound, wherein the ceramide compound is a N-acyl derivative of β-hydroxyalkylamine. In a preferred embodiment, the ceramide compound has the general formula

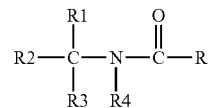

and, wherein R is a saturated or mono- or polyunsaturated (cis or trans) alkyl group having greater than 2 carbon atoms; R1, R2, R3, and R4 may be the same or different and are saturated or mono-or polyunsaturated hydroxylated alkyl groups, aryl groups, or hydrogen. In one embodiment, R4 is an alkyl chain having from 1 to 12 carbon atoms. In a preferred embodiment, R is a saturated or mono- or polyunsaturated (cis or trans) alkyl group having from 12-20 carbon atoms, the hydroxylated alkyl groups have from 1-6 carbon atoms, R1 and R2 are hydroxylated alkyl groups, and R3 is hydrogen.

In another embodiment, the present invention contemplates the use of a composition comprising a sphingosine compound, wherein the sphingosine compound has the general formula

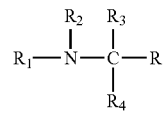

and, R is a saturated or mono- or polyunsaturated (cis or trans) alkyl group having greater than 2 carbon atoms; R1, R2, R3, and R4 may be the same or different and are saturated or mono- or polyunsaturated hydroxylated alkyl groups, aryl groups, or hydrogen. In preferred embodiments, the sphingosine compound is selected from the group comprising D-erythro-sphingosine, L-threo-sphingosine, dimethylsphingosine, and N-oleoyl ethanolamine.

In another embodiment, the present invention contemplates the use of a composition comprising a hydroxyalkyl ester compound, wherein the hydroxyalkyl ester compound has the general formula

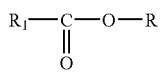

and, wherein R is a saturated or mono- or polyunsaturated (cis or trans) alkyl group having greater than 2 carbon atoms; and R1 is a saturated or mono-or polyunsaturated hydroxylated alkyl group, aryl group, or hydrogen. In a preferred embodiment, the hydroxyalkyl ester compound is an O-acyl derivative of gallic acid. In another preferred embodiment, the hydroxyalkyl ester compound is the n-dodecyl ester of 3,4,5-trihydroxybenzoic acid ("laurylgallate"), which has the formula

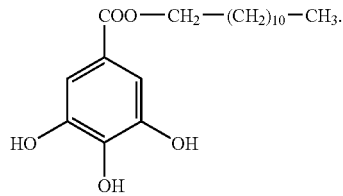

In preferred embodiments of the present invention, the composition comprises a ceramide compound selected from the group consisting of N2-hydroxy-1-(hydroxymethyl) ethyl)-palmitoylamide ("S16"); N-(2-hydroxy-1-(hydroxymethylethyl)-oleoylamide ("S18"); N,N-bis(2-hydroxyethyl)palmitoylamide ("B16"); N,N-bis(2-hydroxyethyl)oleoylamide ("B18"); N-tris(hydroxymethyl) methyl-palmitoylamide ("T16"); N-tris(hydroxymethyl) methyl-oleoylamide ("T18"); N-acetyl sphingosine ("C2-ceramide"); D-threo-1-phenyl-2-decanoylamino-3-morpholino-1-propanol ("D-threo-PDMP"); D-threo-1-phenyl-2-hexadecanoylamino-3-morpholino-1-propanol ("D-Threo-PPMP"); D-erythro-2-tetradecanoyl-1-phenyl-1-propanol ("D-MAPP"); D-erythro-2(N-myristoylamino)-1-phenyl-1-propanol ("MAPP"), and N-hexanoylsphingosine (C6-ceramide).

Those of skill in the art will recognize that many other variations of the general formulas above exist, and that the use of all such variations is encompassed by the methods of the present invention. In more preferred embodiments, the ceramide compound is selected from the group comprising S16, S18 and functional homologies, isomers, and pharmaceutically acceptable salts thereof. In a preferred embodiment the ceramide compound is S18. In another preferred embodiment the ceramide compound is S16. In another preferred embodiment, the amphiphilic lipid compound can include the metabolites and catabolites of the ceramide compound, the sphingosine compound, and the hydroxyalkyl ester compound. The composition comprising the amphiphilic lipid compound may further comprise pharmaceutically acceptable carriers, excipients, additives, preservatives, and buffers.

In the methods of the present invention, it is preferred that the concentration of the amphiphilic lipid compound is from approximately 0.1 µM to 1000 µM, more preferred that the concentration of the amphiphilic lipid compound is from approximately 1 µM to 100 µM, more preferred that the concentration of the amphiphilic lipid compound is from approximately 5 µM to 50 µM, and most preferred that the concentration of the amphiphilic lipid compound is approximately 10 µM.

In the methods of the present invention, it is preferred that the duration of culturing the differentiating human pluripotent cell with the amphiphilic lipid compound is from approximately 1 hour to 20 days, more preferably from approximately 6 hours to 10 days, and most preferably from approximately 12 hours to 6 days.

In a preferred embodiment, the pluripotent cell is a human cell. As used herein, the term "pluripotent human cell" encompasses pluripotent cells obtained from human embryos, fetuses or adult tissues. In a preferred embodiment, the pluripotent human cell is a differentiating cell. In one preferred embodiment, the pluripotent human cell is a human pluripotent embryonic stem cell. In preferred embodiments, the human pluripotent embryonic stem cell is obtained from a domed human embryonic stem cell colony, a crater human embryonic stem cell colony, and a protease passaged human embryonic stem cell colony. In another embodiment the pluripotent human cell is a human pluripotent fetal stem cell, such as a primordial germ cell. In another embodiment the pluripotent human cell is a human pluripotent adult stem cell. As used herein, the term "pluripotent" refers to a cell capable of at least developing into one of ectodermal, endodermal and mesodermal cells. In one preferred embodiment, the pluripotent human cell is a differentiating human cell. As used herein the term "pluripotent" refers to cells that are totipotent and multipotent. As used herein, the term "totipotent cell" refers to a cell capable of developing into all lineages of cells. As used herein, the term "multipotent" refers to a cell that is not terminally differentiated. In one preferred embodiment the multipotent cell is a neural precursor cell and the multipotent cell culture is a neural precursor cell culture. The pluripotent human cell can be selected from the group consisting of a human embryonic stem (ES) cell; a human inner cell mass (ICM)/epiblast cell; a human primitive ectoderm cell, such as an early primitive ectoderm cell (EPL); and a human primordial germ (EG) cell. The human pluripotent cells of the present invention can be derived using any method known to those of skill in the art at the present time or later discovered. For example, the human pluripotent cells can be produced using de-differentiation and nuclear transfer methods. Additionally, the human ICM/epiblast cell or the primitive ectoderm cell used in the present invention can be derived in vivo or in vitro. EPL cells may be generated in adherent culture or as cell aggregates in suspension culture, as described in WO 99/53021, herein incorporated by reference in its entirety.

In preferred embodiments of the above methods, the method the provides for an intermediate step of forming an embryoid body comprising the pluripotent human cell. In one embodiment, the embryoid body is formed by culturing the pluripotent human cell or cell culture with an essentially serum free medium. In a preferred embodiment, the essentially serum free medium is a MEDII conditioned medium as defined herein. In other preferred embodiments, the embryoid body is subsequently cultured with one or more cell differentiation environments to produce a human neural cell or human cell culture enriched in neural cells, wherein each environment is appropriate to the cell types as they appear from the preceding cell type. It is to be understood that the absence of the term "differentiation" when describing a MEDII conditioned medium does not indicate that the MEDII conditioned medium can not also be considered a "differentiation" environment. In certain embodiments, the essentially serum free medium preferably is also essentially LIF free. In a preferred embodiment, a subsequent cell differentiation environment comprises an amphiphilic lipid compound. In a preferred embodiment, the amphiphilic compound is selected from the group comprising a ceramide compound, a sphingosine compound, and an hydroxyalkyl ester. In more preferred embodiments, the ceramide compound is a ceramide analog of the serinol type selected from the group comprising S16, S18 and functional homologues, isomers, and pharmaceutically acceptable salts thereof. In a preferred embodiment the ceramide compound is S18. In another preferred embodiment the ceramide compound is S16. In a preferred embodiment, the composition comprising the amphiphilic lipid compound is essentially serum free.

As used herein, the term "MEDII conditioned medium" refers to a medium comprising one or more bioactive components as described herein. In a preferred embodiment, the bioactive component is derived from a hepatic or hepatoma cell or cell line culture supernatant. The hepatic or hepatoma cell or cell line can be from any species, however, preferred cell lines are mammalian or avian in origin. The hepatic or hepatoma cell line can be selected from, but is not limited to, the group consisting of: a human hepatocellular carcinoma cell line such as a Hep G2 cell line (ATCC HB-8065) or Hepa-1c1c-7 cells (ATCC CRL-2026); a primary embryonic mouse liver sell line; a primary adult mouse liver cell line; a primary chicken liver cell line; and an extraembryonic endodermal cell line such as END-2 and PYS-2. A particularly preferred cell line is the Hep G2 cell line (ATCC HB-8065). A description of the isolation of an essentially serum free MEDII conditioned medium from a Hep G2 cell line is provided in Example 2 below. In one embodiment of the present invention, the MEDII conditioned medium is derived from a Hep G2 cell line and contains supplements of FGF-2.

As used herein, "essentially serum free" refers to a medium that does not contain serum or serum replacement, or that contains essentially no serum or serum replacement. As used herein, "essentially" means that a de minimus or reduced amount of a component, such as serum, may be present that does not eliminate the improved bioactive neural cell culturing capacity of the medium or environment. For example, essentially serum free medium or environment can contain less than 10, 9, 8, 7, 6, 5, 4, 3, 2, or 1% serum wherein the presently improved bioactive neural cell culturing capacity of the medium or environment is still observed.

As used herein, "essentially LIF free" refers to a medium that does not contain leukemia inhibitory factor (LIF), or that contains essentially no LIF. As used herein, "essentially" means that a de mininius or reduced amount of a component, such as LIF, may be present that does not eliminate the improved bioactive neural cell culturing capacity of the medium or environment. For example, essentially LIF free medium or environment can contain less than 100, 75, 50, 40, 30, 10, 5, 4, 3, 2, or 1 ng/ml LIF, wherein the presently improved bioactive neural cell culturing capacity of the medium or environment is still observed.

As used herein, the terms "bioactive component" and "bioactive factor" refer to any compound or molecule that induces a pluripotent cell to follow a differentiation pathway toward an EPL cell or a neural cell. Alternatively, the bioactive component may act as a mitogen or as a stabilizing or survival factor for a cell differentiating towards an EPL cell or neural cell. A bioactive component from the conditioned medium may be used in place of the MEDII conditioned medium in any embodiment described herein. The isolation of a bioactive component of MEDII is shown below in Example 2. While the bioactive component may be as described below, the term is not limited thereto. The term "bioactive component" as used herein includes within its scope a natural or synthetic molecule or molecules which exhibit(s) similar biological activity, e.g. a molecule or molecules which compete with molecules within the conditioned medium that bind to a receptor on ES or EPL cells or their differentiation products in adherent culture, in embryoid bodies, or in nonadherent cultures, responsible for EPL or neural induction, and/or EPL or neural proliferation, and/or EPL or neural survival.

The MEDII conditioned medium described herein can comprise one or more bioactive components selected from the group consisting of a low molecular weight component comprising proline or a proline containing peptide; a biologically active fragment of any of the aforementioned proteins or components; and an analog of any of the aforementioned proteins or components. In addition, the MEDII conditioned medium may contain a neural inducing factor.

The low molecular weight component of the MEDII conditioned medium can comprise one or more proline residues or a polypeptide containing proline residues. As used herein, the term "polypeptide" refers to any of various amides that are derived from two or more amino acids by combination of the amino group of one acid with the carboxyl group of another and usually obtained by partial hydrolysis of proteins. In a preferred embodiment, the low molecular weight component is L-proline or a polypeptide including L-proline. The proline containing polypeptide preferably has a molecular weight of less than approximately 5 kD, more preferably less than approximately 3 kD. In a further preferred embodiment, the low molecular weight component is a polypeptide of between approximately 2-11 amino acids, more preferably of between approximately 2-7 amino acids and most preferably approximately 4 amino acids. The proline containing polypeptide can be selected from, but is not limited to, the following polypeptides: Pro-Ala, Ala-Pro, Ala-Pro-Gly, Pro-OH-Pro, Pro-Gly, Gly-Pro, Gly-Pro-Ala, Gly-Pro-Glu, Gly-Pro-OH-Pro, Gly-Pro-Arg-Pro (SEQ ID. NO:1), Gly-Pro-Gly-Gly (SEQ ID NO:2), Val-Ala-Pro-Gly (SEQ ID NO:3), Arg-Pro-Lys-Pro (SEQ ID NO:4), and Arg-Pro-Lys-Pro-Gln-Gln-Phe-Phe-Gly-Leu-MetOH (SEQ ID NO:5).

The invention further encompasses methods for modulating apoptosis in human pluripotent cell populations comprising modifying expression of an apoptotic regulating factor, and/or modulating the intracellular concentration of endogenous lipid second messengers, such as ceramide. Preferably, the apoptotic regulating factor is PAR-4.

In another embodiment of the above methods, an embryoid body is formed upon culturing the pluripotent human cell or cell culture with an essentially serum free medium, wherein the serum free medium is optionally a MEDII conditioned medium, the embryoid body is dispersed to an essentially single cell suspension, and the essentially single cell suspension is cultured with a composition comprising the amphiphilic lipid compound until the human neural cell is produced or the human cell culture enriched in neural cells is produced. In another embodiment, the embryoid body is formed upon culturing the pluripotent human cell or cell culture with a medium, the embryoid body is dispersed to an essentially single cell suspension, and the essentially single cell suspension is cultured with a composition comprising the amphiphilic lipid compound until the human neural cell is produced or the human cell culture enriched in neural cells is produced. In a preferred embodiment, the essentially single cell suspension is cultured with the amphiphllic lipid compound in an essentially serum free medium. In a further embodiment, the essentially serum free medium comprises a MEDII conditioned medium, proline, or a proline containing polypeptide. In other preferred embodiments, the embryoid body is subsequently cultured with one or more cell differentiation environments to produce a human neural cell or human cell culture enriched in neural cells, wherein each environment is appropriate to the cell types as they appear from the preceding cell type. The amphiphilic lipid compound is selected from the group consisting of a ceramide compound, a sphingosine compound, and a hydroxyalkyl ester compound. In a preferred embodiment, the amphiphilic lipid compound is a ceramide compound of the serinol type.

As used herein, the term "cell differentiation environment" refers to a cell culture condition wherein the pluripotent cells or embryoid bodies derived therefrom are induced to differentiate into neural cells, or are induced to become a human cell culture enriched in neural cells. Preferably the neural cell lineage induced by the growth factor will be homogeneous in nature. The term "homogeneous," refers to a population that contains more than 80%, 85%, 86%, 87%, 88%, 89%, 90%, 91%, 92%, 93%, 94%, 95%, 96%, 97%, 98%, or 99% of the desired neural cell lineage.

In one embodiment, the cell differentiation environment comprises an amphiphilic lipid compound. In a preferred embodiment, the amphiphilic lipid compound is a ceramide compound. In a further embodiment, the cell differentiation environment is a suspension culture. As used herein, the term "suspension culture" refers to a cell culture system whereby cells are not tightly attached to a solid surface when they are cultured. Non-limiting examples of suspension cultures include agarose suspension cultures, and hanging drop suspension cultures. In one embodiment, the cell differentiation environment comprises a suspension culture where the tissue culture medium is Dulbecco's Modified Eagle's Medium and Ham's F12 media (DMEM/F12), and it is supplemented with a fibroblast growth factor (FGF) such as FGF-2. In a preferred embodiment, the cell differentiation environment comprises an FGF. In a preferred embodiment, the cell differentiation environment comprises a suspension culture where the tissue culture medium is DMEM F12, FGF-2, and MEDII conditioned medium. In a preferred embodiment, the suspension culture is an agarose suspension culture. In preferred embodiments, the cell differentiation environment is also essentially free of human leukemia inhibitory factor (hLIF).

In other embodiments, the cell differentiation environment can also contain supplements such as L-Glutamine, NEAA (non-essential amino acids), P/S (penicillin/streptomycin), N2 supplement (5 µg/ml insulin, 100 µg/ml transferrin, 20 nM progesterone, 30 nM selenium, 100 µM putrescine (Bottenstein, and Sato, 1979 PNAS 76, 514-517) and β-mercaptoethanol (β-ME). It is contemplated that additional factors may be added to the cell differentiation environment, including, but not limited to fibronectin, laminin, heparin, heparin sulfate, retinoic acid, members of the epidermal growth factor family (EGFs), members of the fibroblast growth factor family (IGFs) including FGF2 and/or FGF8, members of the platelet derived growth factor family VDGFs), transforming growth factor (TGF)/bone morphogenetic protein (BMP)/growth and differentiation factor (GDF) factor family antagonists including but not limited to noggin, follistatin, chordin, gremlin, cerberus/DAN family proteins, ventropin, and amnionless. TGF, BMP, and GDF antagonists could also be added in the form of TGF, BUT, and GDF receptor-Fc chimeras. Other factors that may be added include molecules that can activate or inactivate signaling through Notch receptor family, including but not limited to proteins of the Delta-like and Jagged families. Other growth factors may include members of the insulin like growth factor family (IGF), the wingless related (WNT) factor family, and the hedgehog factor family. Additional factors may be added to promote neural stem/progenitor proliferation and survival as well as neuron survival and differentiation. These neurotrophic factors include but are not limited to nerve growth factor (NGF), brain derived neurotrophic factor DNF), neurotrophin-3 (NT-3), neurotrophin-4/5 (NT-4/5), interleukin-6 (IL-6), ciliary neurotrophic factor (CNTF), leukemia inhibitory factor (LIF), cardiotrophin, members of the transforming growth factor (TGF)/bone morphogenetic protein (BMP)/growth and differentiation factor (GDF) family, the glial derived neurotrophic factor (GDNF) family including but not limited to neurturin, neublastin/artemin, and persephin and factors related to and including hepatocyte growth factor. Neural cultures that are terminally differentiated to form post-mitotic neurons may also contain a mitotic inhibitor or mixture of mitotic inhibitors including but not limited to 5-fluoro 2'-deoxyuridine and cytosine β-D-arabino-furanoside (Ara-C). The cell differentiation environment can further comprise conditions that are known to lead to an increase in endogenous ceramide levels, including but not limited to ionizing radiation, UV light radiation, application of retinoic acid, heat shock, chemotherapeutic agents such as but not limited to daunorubicin, and oxidative stress. Endogenous ceramide levels can also be elevated by incubating the cells in medium containing a sphingomyelinase or a compound with similar activity, or by treating the cells with an inhibitor of ceramidase such as N-oleoylethanolamine.

In another embodiment, the cell differentiation environment can contain compounds that enhance the activity of the amphiphilic lipid compound. In an alternative embodiment, the cell differentiation environment can contain other inducers or enhancers of apoptosis that synergize with the activity of the amphiphilic lipid compounds. In a further embodiment, the cell differentiation environment can comprise compounds that make the neural cells more resistant to apoptosis. In this embodiment, the addition of compounds that increase the resistance of neural cells to amphiphilic lipid compound enhanced apoptosis allows for the use of higher levels of the amphiphilic lipid compounds. As used herein, the term "higher levels" refers to concentrations of the amphiphilic lipid compound that would inhibit the growth or differentiation of neural cells in the absence of the additional compound, but that do not inhibit the growth or differentiation in the presence of the additional compound.

In other embodiments, the cell differentiation environment comprises an adherent culture. As used herein, the term "adherent culture" refers to a cell culture system whereby cells are cultured on a solid surface, which may in turn be coated with a substrate. The cells may or may not tightly adhere to the solid surface or to the substrate. The substrate for the adherent culture may further comprise any one or combination of polyornithine, laminin, poly-lysine, purified collagen, gelatin, extracellular matrix, fibronectin, tenacin, vitronectin, poly glycolytic acid (PGA), poly lactic acid (PLA), poly lactic-glycolic acid (PLGA) and feeder cell layers such as, but not limited to, primary astrocytes, astrocyte cell lines, glial cell lines, bone marrow stromal cells, primary fibroblasts or fibroblast cells lines. In addition, primary astrocyte/glial cells or cell lines derived from particular regions of the developing or adult brain or spinal cord including but not limited to olfactory bulb, neocortex, hippocampus, basal telencephalon/striatum, midbrain/mesencephalon, substantia nigra, cerebellum or hindbrain may be used to enhance the development of specific neural cell sub-lineages and neural phenotypes.

In other embodiments of the present invention, it is not required that an embryoid body is formed upon culturing the pluripotent human cell or cell culture. In these embodiments, a pluripotent human cell or cell culture is cultured with a medium, and as an additional step, the resultant cells are cultured with a composition comprising an amphiphilic lipid compound to produce a human neural cell or human cell culture enriched in neural cells. In some embodiments, prior to culturing the cell with the composition comprising the amphiphilic lipid compound, the pluripotent human cell is first cultured with an essentially serum free medium. In other embodiments, the essentially serum free medium is a MEDII conditioned medium or the bioactive component of a MEDII conditioned medium. In still other embodiments, the cells cultured with the amphiphilic lipid compound are subsequently cultured with one or more cell differentiation environments to produce a human neural cell or human cell culture enriched in neural cells, wherein each medium is appropriate to the cell types as they appear from the preceding cell type. In a preferred embodiment, the amphiphilic lipid compound is selected from the group consisting of a ceramide compound, a sphingosine compound, and a hydroxyalkyl ester compound. In a preferred embodiment, the amphiphilic lipid compound is a ceramide compound of the β-hydroxyalkylamine type.

The present invention further contemplates methods of enhancing the efficiency of the transplantation of a cultured human pluripotent cell or cell culture, comprising the steps of (a) culturing a human pluripotent cell with a growth medium comprising a ceramide compound of the general formula described above, wherein R is a saturated or mono- or polyunsaturated (cis or trans) alkyl group having greater than 2 carbon atoms, and R1, R2, R3, and R4 may be the same or different and are saturated or mono-or polyunsaturated hydroxylated alkyl groups, aryl groups, or hydrogen; and (b) transplanting the cultured human pluripotent cell or cell culture into the patient. In one embodiment, R4 is an alkyl chain having from 1 to 12 carbon atoms. In a preferred embodiment, R is a saturated or mono- or polyunsaturated (cis or trans) alkyl group having from 12-20 carbon atoms, the hydroxylated alkyl groups have from 1-6 carbon atoms, and R1 and R2 are hydroxylated alkyl groups. In other preferred embodiments, the ceramide compound is selected from the group comprising S16, S18 and functional homologues, isomers, and pharmaceutically acceptable salts thereof. In a preferred embodiment the ceramide compound is S18. In another preferred embodiment the ceramide compound is S16. In a preferred embodiment of the above method, the cell population comprising the cultured human pluripotent cell contains at least 80% of a neural cell.

As used herein, the term "neural cell" includes, but is not limited to, a neurectoderm cell; an EPL derived cell; a glial cell; a neural cell of the central nervous system such as a dopaminergic cell, a differentiated or undifferentiated astrocyte or oligodendrocyte; a neural stem cell, a neural progenitor, a glial progenitor, an oligodendrocyte progenitor, and a neural cell of the peripheral nervous system. As used herein, the term "neurectoderm" refers to undifferentiated neural progenitor cells substantially equivalent to cell populations comprising the neural plate and/or neural tube; or a partially differentiated neural progenitor cell. Neurectoderm cells are multipotential. Therefore, "neural cell" as used in the context of the present invention, is meant that the cell is at least more differentiated towards a neural cell type than the pluripotent-cell from which it is derived. Also as used herein, producing a neural cell encompasses the production of a cell culture that is enriched for neural cells. In preferred embodiments, the term "enriched" refers to a cell culture that contains more than approximately 50%, 55%, 60%, 65%, 70%, 75%, 80%, 85%, 90%, or 95% of the desired cell lineage.

The present invention further contemplates a composition for promoting maintenance, proliferation, or differentiation of a human neural cell, the composition comprising a cell culture medium comprising MEDII conditioned medium or the bioactive component of a MEDII conditioned medium and an amphiphilic lipid compound of the general formulas described above. Preferably the amphiphilic lipid compound is selected from the group consisting of the ceramide compound, the sphingosine compound, and the hydroxyalkyl ester compound of the formulas described above. In a preferred embodiment, the amphiphilic lipid compound is a ceramide compound of the β-hydroxyalkylamine type, wherein R is a saturated or mono- or polyunsaturated (cis or trans) alkyl group having from 12-20 carbon atoms, the hydroxylated alkyl groups have from 1-6 carbon atoms, and R1 and R2 are hydroxylated alkyl groups. In one embodiment, the ceramide compound is selected from the group consisting of N-(2-hydroxy-1-(hydroxymethyl)ethyl)-palmitoylamide ("S16"); N-(2-hydroxy-1-(hydroxymethyl)ethyl)-oleoylamide ("S18"); N,N-bis(2-hydroxyethyl)palmitoylamide ("B16"); N,N-bis(2-hydroxyethyl)oleoylamide ("B18"); N-tris(hydroxymethyl)methyl-palmitoylamide ("T16"); N-tris(hydroxymethyl)methyl-oleoylamide ("T18"); N-acetyl sphingosine ("C2"); D-threo-1-phenyl-2-decanoylamino-3-morpholino-1-propanol ("D-threo-PDTP"); D-threo-1-phenyl-2-hexadecanoylamino-3-morpholino-1-propanol ("D-Threo-PPMP"); D-erythro-2-tetradecanoyl-1-phenyl-1-propanol ("D-MAPP"); D-erythro-2-(N-myristoylamino)-1-phenyl-1-propanol ("KAPP"); and N-hexanoylsphingosine (C6-ceramide). In more preferred embodiments, the ceramide compound is selected from the group comprising S16, S18 and functional homologues, isomers, and pharmaceutically acceptable salts thereof. In a preferred embodiment the ceramide compound is S18. In another preferred embodiment the ceramide compound is S16. In other embodiments, the amphiphilic lipid compound is a sphingosine compound, wherein the sphingosine compound is selected from the group consisting of D-erythro-sphingosine, L-threo-sphingonine, dimethylsphingosine, and N-oleoyl ethanolamine. In other embodiments, the amphiphilic lipid compound is a hydroxyalkyl ester compound, wherein the hydroxyalkyl ester is laurylgallate. The composition comprising the amphiphilic lipid compound may further comprise pharmaceutically acceptable carriers, excipients, additives, preservatives, and buffers. The invention also contemplates the neural cell or human cell culture enriched in neural cells that is cultured in the composition.

The MEDII conditioned medium described herein can comprise one or more bioactive components selected from the group consisting of a low molecular weight component; a biologically active fragment of any of the aforementioned proteins or components; and an analog of any of the aforementioned proteins or components. The bioactive component is a neural inducing factor, and in a preferred embodiment, is isolated from MEDII conditioned medium using purification techniques well known in the art. At each step of the purification procedure the samples or fractions are applied the pluripotent cell to test for the presence of the neural inducing factor. The bioactive component can be proline or a proline containing peptide The step of culturing the human pluripotent cells with the MEDII conditioned medium to produce embryoid bodies (EBs) or EPL cells can be conducted in any suitable manner. For example, EPL cells may be generated in adherent culture or as cell aggregates in suspension culture. EBs may be generated in suspension culture using the hanging drop technique or by culturing the cells on agarose coated plates. EBs can be generated in serum containing medium, or in essentially serum free medium. It is also to be understood that the step of culturing the embryoid body with an essentially serum free medium and/or an essentially serum free cell differentiation environment can also be conducted in any manner known to those of skill in the art. In one embodiment, the embryoid body is initially generated in serum containing medium and then transferred to an essentially serum free medium for further neural differentiation and ceramide treatment.

As stated above, the present invention provides a method of producing a neural cell or producing a human cell culture enriched in neural cells comprising the steps of: a) providing a pluripotent human cell; b) culturing the pluripotent human cell with an essentially serum free MEDII conditioned medium to form an embryoid body, and c) culturing cells from the embryoid body with a composition comprising a ceramide compound to produce the neural cell or the human cell culture enriched in neural cells. It is to be understood that the step of culturing the pluripotent cell with the essentially serum free MEDII conditioned medium can include the use of a "normal" or "other" essentially serum free medium supplemented with a RMDII conditioned medium The "normal" or "other" medium, such as a normal human ES medium, can be supplemented with an essentially serum free MEDII conditioned medium at any concentration, but it is preferred that the "normal" or "other" medium can be supplemented at between approximately 10-75%, more preferably between approximately 40-60% and most preferably approximately 50% essentially serum free MEDII conditioned medium. The "normal" or "other" medium that is supplemented with essentially serum free MEDII conditioned medium is also essentially serum free, containing no or essentially no serum. In one embodiment, the pluripotent human cell is cultured with the essentially serum free cell differentiation environment between approximately 1-60 days, more preferably between approximately 2-28 days, and most preferably 5-15 days.

The present invention encompasses the human neural cells and the human cell cultures enriched in neural cells produced by any of the above-described methods. In preferred embodiments, the neural cell is capable of expressing one or more of the detectable markers for tyrosine hydroxylase (T), vesicular monamine transporter (VMAT) dopamine transporter (DAT), and aromatic amino acid decarboxylase (AADC, also known as dopa decarboxylase). In preferred embodiments, the neural cell expresses less Oct-4 protein than an embryonic stem cell or a pluripotent human cell. The human neural cells or cell cultures enriched in neural cells generated using the compositions and methods of the present invention can be generated in adherent culture or as cell aggregates in suspension culture. Preferably, the human neural cells or cell cultures enriched in neural cells are produced in suspension culture.

The present invention further comprises the use of cell sorting techniques at any one or more stage of any of the above-described methods. In certain embodiments, the cell sorting techniques comprise labeling the cell population and subsequent selecting cells which have or have not been labeled. The term "label" refers to a molecule or composition of molecules that is detectable by optical, spectroscopic, photochemical, biochemical, immunological, chemical or magnetic means. Labels can be specifically targeted to selected cells, but need not be. Such markers or labels include, but are not limited to, colored, radioactive, fluorescent, ultraviolet, or magnetic molecules or particles conjugated to antibodies or other molecules or particles known to bind to cells or cellular components. Antibodies are often used as label components because of their ability to target specific cell types. Other reactive label components that can serve as alternatives to antibodies include, but are not limited to, genetic probes, dyes, fluorochromes, proteins, peptides, amino acids, sugars, polynucleotides, enzymes, coenzymes, cofactors, antibiotics, steroids, hormones or vitamins. The label often generates a measurable signal, which can be detected with or without some kind of stimulatory event and can be used to detect the presence of bound label and possibly quantitate the amount of bound label in a sample. Furthermore, the label may be a detectable intrinsic property of the cell, such as cell size or morphology, which is detectable, for example, by measuring light scattering characteristics. The label may be directly detectable or indirectly detectable or operate in conjunction with another label. For further examples of labels see those listed in Handbook of Fluorescent Probes and Research Chemicals, 9th Ed., Molecular Probes, Inc., Eugene, Oreg. In one embodiment, the protein is labeled with an antibody. In one embodiment, the cell sorting technique comprises the use of fluorescence activated cell sorting, or FACS to separate the labeled cells from the non-labeled cells. Other cell sorting techniques are well-known to those of ordinary skill in the art, and may be employed in the methods of the current invention.

The human neural cells produced using the methods of the present invention have a variety of uses. In particular, the neural cells can be used as a source of nuclear material for nuclear transfer techniques, and used to produce cells, tissues or components of organs for transplant. The invention contemplates that the neural cells of the present invention are used in human cell therapy or human gene therapy to treat a patient having a neural disease or disorder, including but not limited to Parkinson's disease, Huntington's disease, lysosomal storage diseases, multiple sclerosis, memory and behavioral disorders, Alzheimer's disease, epilepsy, seizures, macular degeneration, and other retinopathies. The cells can also be used in treatment of nervous system injuries that arise from spinal cord injuries, stroke, or other neural trauma or can be used to treat neural disease and damage induced by surgery, chemotherapy, drug or alcohol abuse, environmental toxins and poisoning. The cells are also useful in treatment of peripheral neuropathy such as those neuropathies associated with injury, diabetes, autoimmune disorders or circulatory system disorders. The cells may also be used to treat diseases or disorders of the neuroendocrine system, and autonomic nervous system including the sympathetic and parasympathetic nervous system. In a preferred embodiment, a therapeutically effective amount of the neural cell or cell culture enriched in neural cells is administered to a patient with a neural disease. As used herein, the term "therapeutically effective amount" refers to that number of cells which is sufficient to at least alleviate one of the symptoms of the neural disease, disorder, nervous system injury, damage or neuropathy. In a preferred embodiment, the neural disease is Parkinson's disease.

The neural cells of the invention can also be used in testing the effect of molecules on neural differentiation or survival, in toxicity testing or in testing molecules for their effects on neural or neuronal functions. This could include screens to identify factors with specific properties affecting neural or neuronal differentiation, development, survival, plasticity or function. In this application the cell cultures could have great utility in the discovery, development and testing of new drugs and compounds that interact with and affect the biology of neural stem cells, neural progenitors or differentiated neural or neuronal cell types. The neural cells can also have great utility in studies designed to identify the cellular and molecular basis of neural development and dysfunction including but not limited to axon guidance, neurodegenerative diseases, neuronal plasticity and learning and memory. Such basic neurobiology studies may identify novel molecular components of these processes and provide novel uses for existing drugs and compounds, as well as identify new drug targets or drug candidates.

The neural cell or the human cell culture enriched in neural cells may disperse and differentiate in vivo following brain implantation. In particular, following intraventricular implantation, the cell can be capable of dispersing widely along the ventricle walls and moving to the sub-ependymal layer. The cell can be further able to move into deeper regions of the brain, including into the untreated (e.g., by injection) side of the brain into sites that include but are not limited to the thalamus, frontal cortex, caudate putamen and colliculus. In addition the neural cell or human cell culture enriched in neural cells can be injected directly into neural tissue with subsequent dispersal of the cells from the site of injection. This could include any region, nucleus, plexus, ganglion or structure of the central or peripheral nervous systems. In a preferred embodiment, following brain implantation, the neural cell or the human cell culture enriched in neural cells previously cultured with the ceramide compound induces the formation of fewer teratomas than cells or cell cultures not cultured with the compound.

The method of enriching populations of stem or progenitor cells via ceramide induced cell death has potential applications in other areas as well. For example, autologous transplants of hematopoietic stem or progenitor cells may be useful in the treatment of cancers including but not limited to cancers of the hematopoietic system such as leukemias and lymphomas as well as solid tumors. To date, this approach has had limited success due to the infusion of cancerous cells along with normal hematopoietic cells in the autologous graft (Rill et al., 1994 Blood, 84:380-383). Efforts directed at removing-cancer cells from autologous grafts of hematopoietic cells by cell sorting protocols have not yet been uniformly successful in completely removing cancerous cells from the autografts resulting in the potential or actual recurrence of disease in recipients of the autologous hematopoietic graft (Dreger et al., 2000 Experimental Hematology, 28:1187-1196; Rasmussen et al., 2002 Experimental Hematology, 30:82-88). Incubation of hematopoietic cells with ceramide analogs or the activation of ceramide signaling pathways in these cell populations may remove cancerous or tumor forming cells within these populations.

Throughout this application, various publications are referenced. The disclosures of all of these publications and those references cited within those publications in their entireties are hereby incorporated by reference into this application in order to more fully describe the state of the art to which this invention pertains. The following examples are not intended to limit the scope of the claims to the invention, but are rather intended to be exemplary of certain embodiments.

EXAMPLES

Example 1

Production of Ceramide Analogs

Ceramide analogs were produced as described in U.S. Pat. No. 6,410,597 to Bieberich, the entire contents of which are hereby incorporated by reference. Briefly, the compound S16 (N-(2-hydroxy-1-(hydroxymethyl)ethyl)-paimitoylamide) was synthesized from a solution of 50 mg (549 μmoles) of 2-amino-1,3-propanediol in 15 ml of pyridine supplemented with 1.65 mmol (457 μl) of palmitoylchloride at −30° C. The reaction mixture was stirred for 2 hours at room temperature followed by the addition of 30 ml of $CH_3OH$. After stirring for another 2 hours at room temperature the reaction mixture was concentrated by evaporation. For selective hydrolysis of any ester groups formed during the reaction, the concentrate was treated with a 30 ml solution of $CH_3OH$ and sodium methoxide (pH 11-12) and stirred for 2 hours at room temperature. The reaction mixture was neutralized with dilute HCl and then concentrated. The reaction product obtained was purified by chromatography on a silica gel column (5 g) with $CHCl_3/CH_3OH$ (5:1 by volume) as the eluent The yield of S16 was 135 mg (75%). The purity and structure were verified by nuclear magnetic resonance (NMR) and mass spectrometry.

The octanoyl-, oleoyl-, and stearoyl derivatives (S8, S18 and SS18) were synthesized following the procedure used above for the synthesis of S16, but using octanoyl chloride, oleoyl chloride and stearoyl chloride, respectively, instead of palmitoyl chloride in the procedure.

The T16 compound was prepared by following the procedure used above for the synthesis of S16, but using bishydroxyethyl)amine instead of 2-amino-1,3-propanediol. The T18 was prepared by following the procedure used above for the synthesis of T16, but using oleoyl chloride instead of palmitoyl chloride in the procedure.

The ceramide compounds were lyophilized and stored in the dark until use. The compound was dissolved in ethanol to make a stock solution, and the stock solution was added to an appropriate pre-warmed tissue culture mediumprior to culturing the cells with the ceramide compound.

Example 2

Production of Essentially Serum Free MEDII Conditioned Medium, and Isolation of Small Molecular Weight Component of MEDII Media Serum free MEDII (sfMEDII) was used as a source of the biologically active factor in all purification protocols. An essentially serum free MEDII conditioned medium was produced as follows. Hep G2 cells (Knowles et al., 1980 Nature, 288:615-618; ATCC HB-8065) were seeded at a density of $5 \times 10^4$ cells/cm² and cultured for three days in DMEM. Cells were washed twice with 1× PBS and once with serum free medium (DMEM containing high glucose but without phenol red, supplemented with 1 mM L-glutamine, 0.1 mM β-ME, 1× ITSS supplement (Boehringer Mannheim), 10 mM HEPES, pH 7.4 and 110 mg/L sodium pyruvate) for 2 hours. Fresh serum free medium was added at a ratio of 0.23 ml/cm² and the cells were cultured for a further 34 days. SfMEDII was collected, sterilized and stored.

Large Scale Preparation of R and E Fractions from sfMEDII

The starting material for purification and analysis of bioactive factors from MEDII was derived by ultrafiltration of sfMEDII over an Amicon Diaflo YM3 membrane using a 400 ml ultrafiltration cell (Amicon) at 4° C. under nitrogen pressure. The retained fraction (R), $>3 \times 10^3 M_r$, was used immediately or aliquoted and stored at −20° C. The eluted fraction (E), $<3 \times 10^3 M_r$, was used immediately or stored at 4° C.

Purification of the Low Molecular Weight Component of the EPL Cell-Inducing Activity 220 ml of E was applied to a Sephadex G10 column (1100 ml bed volume, 110×113 mm) equilibrated in water. Elution was with water at room temperature at a flow rate of 35 ml/minute. Fractions of 45 ml were collected and a 1 ml aliquot of each fraction was lyophilized. Lyophilized fractions were resuspended in 100 µl of water and 25 µl was assayed for neural and/or EPL cell-inducing activity. Activity was detected in fractions 6-10, 19-25.2 minutes after injection.

Fractions 7 to 9 were pooled, lyophilized and resuspended in 1 ml of 30:70 methanol:acetonitrile. Samples were centrifuged at 14,000 rpm for 10 minutes to remove precipitates and applied to a 10 mm Waters radial pak normal phase silica column (8 mm I.D.) attached to a Waters 510 HPLC machine. The column was washed with 30:70 methanol: acetonitrile at a flow rate of 0.2 ml/minute for 15 minutes before the material was eluted with a 20 minute linear gradient against water using a flow rate of 0.5 ml/minute. Eluted material was detected with a Waters 490E programmable multiwavelength detector set at 215 nm. One ml fractions were collected, lyophilized, resuspended in 50 µl DMEM and assayed for neural and/or EPL cell inducing activity which eluted from the column at 70% water/30% (30:70 methanol:acetonitrile).

The fractions of highest activity from normal phase chromatography, between 32 and 35 minutes, were lyophilized, resuspended in 50 µl water and 10 µl was applied to a Superdex peptide gel filtration column (Pharmacia) connected to a SMART micropurification system (Pharmacia) and equilibrated in water at room temperature. The column was eluted with water at a flow rate of 25 µl/minute and 25 µl samples were collected. This was repeated 5 times to obtain adequate sample for analysis. Individual samples were assayed directly for bioactivity which was detected in fractions eluting approximately 71.04 to 74.04 minutes after injection in a single peak or several closely eluting peaks (i.e. fractions 8, 9 and 10). The predicted molecular weight of the active fractions was <700D according to the elution volume.

Characterization of the Purified Low Molecular Weight Component

Fraction 9 from the Superdex peptide gel filtration column was lyophilized, derivatized with FMOC and OPA and amino acid analysis was conducted with and without hydrolysis using a Hewlett-Packard Amino-Quant II analyzer. Results were compared with a control sample of non-conditioned medium subjected to an identical purification. The amino acid alanine and the amino acid proline were present in abundance compared to the control in both hydrolyzed and unhydrolyzed samples. This indicates that these amino acids were present within the purified sample as free amino acids and not as peptides.

Further explanation of the small molecular weight component can be found in International Application No. WO 99/53021, herein incorporated by reference in its entirety.

Example 3

Induction of Apoptosis by Treatment of Murine ES Cells with Novel Ceramide Analogs of the β-Hydroxyalkylamine Type Methods In Vitro Neural Differentiation of Murine ES Cells In vitro neural differentiation of mouse ES cells (ES-J1, ES-D3) followed a serum deprivation protocol as described previously (Hancock, et al., 2000 Biochem. Biophys. Res. Commun., 271: 418-421). The differentiation stages are outlined in FIG. 2. Briefly, ES cells were grown on gamma-irradiated feeder fibroblasts for four days in Knockout DMEM/15% Knockout serum replacement, supplemented with ESGRO (LIF; Chemicon; Cat No. ESG1106) at a concentration of $10^3$ units/ml medium. ES cells were then grown for another four days on gelatin-coated bacterial culture dishes without a fibroblast feeder layer, and were then grown for three days in Knockout DMEM/15% heat-inactivated ES qualified Fetal Bovine Serum, supplemented with $10^3$ units LIF per ml of medium. Upon trypsinization, ES cells were transferred to bacterial culture dishes without gelatin, and embryoid body (EB) formation was induced for four days in Knockout DMEM/10% heat-inactivated ES qualified FBS without LIF (EB4 stage). On the fifth day, floating and loosely attached EBs were rinsed off and transferred to tissue culture dishes. The EBs were allowed to attach to the tissue culture dish surface by incubation for another 24 hours in Knockout DMEM with 10% heat-inactivated ES qualified fetal bovine serum. Neural differentiation due to serum deprivation was induced by cultivation of the EBs for three days in DME/12 (50/50), supplemented with 1×N2 (Invitrogen/Life Technologies; Cat No. 17502, dilution of 1:100) but without serum (EB8 stage). Serum-deprived EBs were then trypsinized, plated on poly-L-ornithine/laminin-coated tissue culture dishes and grown for four days in DMEM/F12 (50/50), supplemented with N2 and 10 ng/ml FGF-2, but without serum. This incubation period is referred to as neuroprogenitor (NP) stage due to commitment of neuroepithelial precursor cells to neuroprogenitor cells, and/or due to the selective expansion of neural progenitor cells in the FGF-2 containing serum-free medium. These cells have committed during the EB stages and were expanded during the NP stage. NPs grown for 48 hours upon replating of trypsinized EBs were referred to as the NP2 stage. On the fifth day of NP formation, the medium was changed to Neurobasal (Invitrogen/Life Technologies; Cat No. 21103-049), with 5% heat-inactivated FBS, and the cells were incubated for another seven days. During this time, NPs fully differentiate to glial cells and neurons. Cells cultured for 24 hours or 96 hours upon changing the medium were referred to as the D1 or D4 stage, respectively.

ES cells were cultured and differentiated to the EB4, EB8, NP2, or D4 stage following the protocol as described above. The ceramide analog S18 was dissolved in ethanol at a concentration of 100 mM and then added to the cells at a final concentration of 75 µM in medium. The cells at the EB8 stage were incubated for 48 hours in the presence of the ceramide analog and were then transplanted into mouse brains.

Ceramide Analysis

The extraction and quantitative determination of the ceramide levels by high performance thin layer chromatography (HPTLC) followed a standard protocol as described previously (Bieberich et al., 2001, J. Biol. Chem., 276:44396-44404; and Bieberich et al., 1999, J. Neurochem., 72:1040-1049). Briefly, ES cells and ES-derived neural cultures were homogenized in 500 µl of deionized water and lipids were extracted with 5 ml of $CHCl_3/CH_3OH$ (1:1 by volume). The lipid extract was adjusted to the composition of solvent A ($CHCl_3/CH_3OH/H_2O$, 30:60:8 by volume) and acidic and neutral lipids were separated by chromatography on 1 ml of DEAE-Sephadex A-25. The unbound neutral lipids were washed out with 6 ml of solvent A and were then concentrated by evaporation with a gentle stream of nitrogen. The dried residue was re-dissolved in methanol for separation by HPTLC using the running solvent $CHCl_3/HOAc$ (methanol:

acetic acid; 9:1 by volume). Lipids were stained with 3% cupric acetate in 8% phosphoric acid for quantification by comparison with various amounts of standard lipids.

Imunofluorescence Microscopy and TUNEL Assay

Differentiating ES cells were grown on cover slips and fixed with 4% paraformaldehyde in phosphate-buffered saline (PBS). Fixed cells were permeabilized with 0.5% Triton X-100 in PBS for 5 minutes at room temperature and unspecific binding sites were saturated by incubation with 3% ovalbumin in PBS for 1 hour at 37° C. The cover slips were then incubated with 5 µg/ml primary antibody (anti-ceramide clone 15B4 mouse IgM, Alexis; anti-PAR-4 rabbit IgG, Santa Cruz; anti-PCNA rabbit IgG, Santa Cruz; anti-nestin clone 401 rat IgG, BD Pharmingen) in 0.1% ovalbumin/PBS, followed by incubation with the appropriate fluorescence-labeled secondary antibody (5 µg/ml Alexa 546 conjugated anti-mouse IgG, Molecular Probes; Alexa 488 conjugated anti-rabbit IgG, Molecular Probes, Cy3 conjugated anti-mouse IgM, Jackson) for 2 hours at 37° C. The nuclei were stained by treatment with 2 µg/ml Hoechst 33258 in PBS for 30 minutes at room temperature. Apoptotic nuclei were stained using the fluorescein FragEL TUNEL assay (Oncogene) according to the manufacturer's instructions.

Statistical Analysis

Antigen specific immunostaining was quantified by counting cells that fluoresced at least twice as much as the background fluorescence. Cell counts were performed in five areas of approximately 200 cells each that were obtained from three independent immunostaining reactions. A Chi square test with one degree of freedom was applied for the statistical analysis of the distribution of two immunostained antigens. The first null hypothesis ($HO^1$) to be refuted was that the two antigens were independently distributed within the total cell population (mean of 200 cells in five counts). The expected frequency for double-staining was the frequency product for immunostaining of A or B in the total population, $f(A \text{ and } B)=f(A) \times f(B3)$. The second null hypothesis ($HO^2$) to be refuted was that the frequency of antigen B in the subpopulation A was identical to its frequency in the total population, $f(B \text{ in } A)=f(B3 \text{ in } A+B)$.

Results

The concentration of endogenous ceramide in apoptotic, undifferentiated stem cells and non-apoptotic, neural progenitor cells was determined. In contrast to cancer cells, the undifferentiated stem cells and neural progenitor cells had elevated levels of endogenous ceramide prior to treatment with the ceramide compounds, indicating that ceramide analogs of the serinol type enhance or sustain apoptosis in undifferentiated stem cells, rather than inducing or initiating apoptosis in the undifferentiated stem cells. However, neural progenitor cells, although they had elevated levels of endogenous ceramide, were protected against ceramide compound-induced and/or -enhanced apoptosis.

Figure 4:
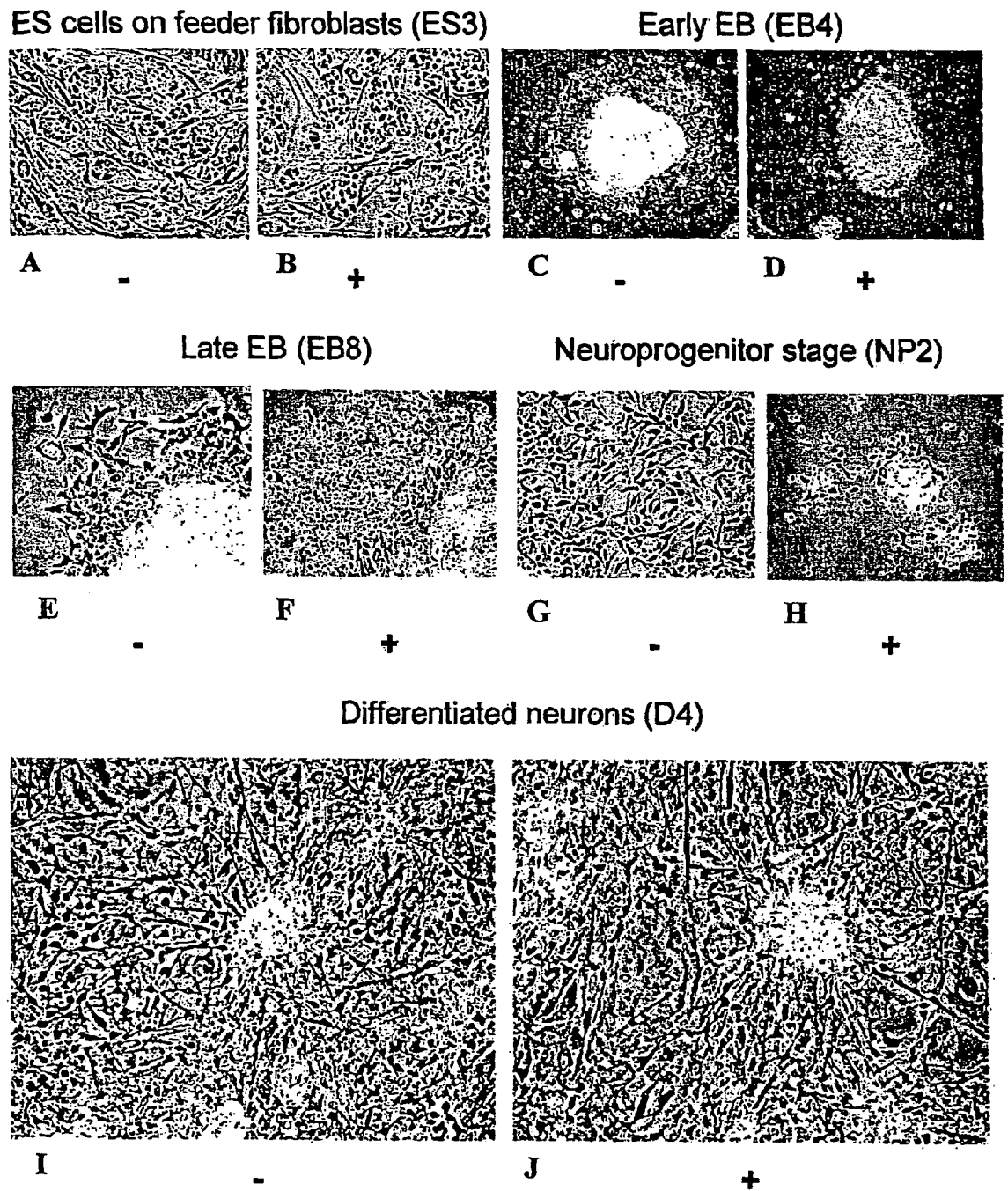

The degree of apoptosis that occurred naturally in differentiating mouse ES cells or that occurred upon incubation for 15 hours with 75 µM of the novel ceramide analogs S16 or S18, or 35 µM N-acetyl sphingosine (C2-ceramide) was determined. FIG. 2 shows the in vitro neural differentiation of mouse embryonic stem cells, indicating the various stages of differentiation. FIGS. 3 and 4 show that cell death was prominent at the EB8 or NP2 stages, whereas differentiated neurons did not reveal characteristics of apoptotic cells. The degree of apoptosis was quantified by counting TUNEL stained (apoptotic) cells. Apoptosis was elevated at the EB8 stage, when 20±5% of cells were apoptotic, and was most prominent at the NP2 stage when 35±5% of cells were apoptotic. Incubation with S16, S18, or C2-ceramide enhanced apoptosis, and increased the number of TUNEL stained cells to 45±10% at the EB8 stage and 70±10% at the NP2 stage. Enhancement of apoptosis by ceramide analogs was also observed in undifferentiated ES cells, where 40±10% of cells were apoptotic, and at the EB4 stage, where 25±5% of cells were apoptotic.

The sensitivity of differentiating NP cells rapidly decreased upon the post-treatment plating of trypsinized EBs at day 8 (EB8). Sensitivity to ceramide analogs was highest for NP2, while the sensitivity to the analogs was already less than 20% at the D1 stage. TUNEL staining revealed that differentiated neurons at the D4 stage did not show significant levels of apoptosis (<10±5%) upon incubation with ceramide analogs.

FIG. 4F shows that at the EB8 stage, a rim of cells surrounding the central embryoid body resisted apoptosis induced by novel ceramide analogs. Immunostaining of EBs with an antibody against nestin, a marker protein for neural progenitor cells, revealed that this rim of non-apoptotic cells strongly stains for nestin (FIG. 5B). Therefore, neural progenitor cells that express nestin were less sensitive toward ceramide induced or enhanced apoptosis, whereas nestin-negative, undifferentiated cells were sensitive to ceramide-enhanceable apoptosis. Cell counts revealed that of TUNEL positive cells, 8% were nestin positive (5/65) while 80% (108/135) of the TUNEL negative cells expressed nestin protein.

A quantitative determination of different marker proteins and TUNEL staining for apoptotic cells showed that predominantly nestin negative, proliferating cell nuclear antigen (PCNA) positive cells underwent apoptosis (FIG. 6). PCNA is a specific marker protein for cells that undergo rapid cell division. PCNA positive cells are not neural progenitor cells, but show rapid proliferation. These highly proliferative cells are likely to be residual pluripotent stem cells since these cells are known to have a cell cycle with greatly abbreviated G1 and G2 phases while differentiated cells derived from pluripotent stem cells have longer cell cycles with longer G1 and G2 phases (WO 01/23531, herein incorporated by reference). The elimination of these rapidly proliferating cells by selective apoptosis will thus reduce significantly the risk of teratoma formation after transplantation of pluripotent stem cell-derived cells into the host tissue.

Example 4

Injection of Ceramide Analog Treated EB-derived Stem Cells into Mouse Brains

Methods

In vitro differentiating ES cells at stage EB8 were incubated for 2448 hours with 75 µM S18, or 35 µM N-acyl sphingosine or other ceramide analogs. Protein was isolated from cells incubated with S18 for 24 hours and from untreated cells, separated by SDS-PAGE, and the expression of Oct-4 was analyzed by immunoblotting.

Prior to injection into the mouse brain, ES cells were labeled with Vybrant-DiI (rhodamine fluorescence) for permanent vital staining and were mixed with India ink in order to track the injection channel and cell migration/tissue integration. $1 \times 10^4$ of the untreated ES-J1 cells were injected, while $2 \times 10^4$ of the S18-treated cells were injected in order to control for the percentage of cells lost to apoptosis. The ES cells were injected into the right brain hemisphere (bregma—1.5 mm, 1 mm lateral of central suture, 2.0 mm deep) of 8-10 day old C57BL6 mice using a Hamilton syringe. After 7-21 days, the mice were sacrificed, the brain isolated and fixed with 10% PBS-buffered formalin. The brains were Vibratome sectioned at 100 µm. The distribution of the injected cells was determined by fluorescence microscopy.

In another preparation, apoptotic cells derived from S18-incubated EBs were fluorescence labeled using Annexin V or FLICA (fluorochrome inhibitors of caspases) staining. Apoptotic (fluorescence labeled) cells were removed by fluorescence activated cell sorting (FACS) and the non-apoptotic cells were used for injection into mouse brain or were used for in vitro neuronal differentiation.

Results

The protein preparation from S18 treated cells demonstrated only 25% of the Oct-4 immunostaining found in the untreated control cells. This indicated that Oct-4 protein levels were suppressed, or that Oct-4 expressing cells were eliminated such that a 75% decrease in Oct-4 protein levels was observed after treatment with S18.

FIG. 7A shows that ten days after injection of the cells, massive teratoma formation was found on the right side of the brain that was injected with untreated, control cells. However, EB8-derived cells that were treated with S18 did not show teratoma formation (FIG. 7B). In another experiment, EB8-derived cells were stained with a fluorescent marker dye, Vybrant diI in order to track the migration and integration of the injected cells into the recipient's brain tissue. FIGS. 8A-D show that untreated cells formed numerous teratomas that resulted in death of the recipient at 8 days post-injection. S18-treated EB8-derived cells, however, did not form teratomas, migrated to the hippocampus, and integrated into the host's brain tissue (FIGS. 8E-H). The host injected with the ceramide analog treated cells was killed after 21 days in order to analyze the brain tissue. From two separate transplantation experiments a total of 5 animals were implanted with S18 treated cells. No teratomas were detected in the animals implanted with S18 treated cells. A total of 4 control animals were implanted with untreated cells. One of these controls died and its brain could not be analyzed, the remaining three control animals all contained teratomas formed from the injected untreated cells.

Cultivation of non-apoptotic cells isolated by FACS showed the typical morphology of neuroprogenitors. Hence, FACS sorting and removal of apoptotic cells from the S18-treated EBs prior to injection may further minimize the risk of teratoma formation and enrich the portion of neuroprogenitors.

Example 5

Induction of Apoptosis in Mouse Neuroblastoma Cells

Mouse neuroblastoma (F-11) cells were incubated for 24 hours in 0.1, 0.2, 0.5, or 1.0 µM of laurylgallate (Aldrich). Apoptosis was determined by punctate staining of condensed nuclei with Hoechst 33258 (Sigma, 2 µ/ml medium for 30 minutes at room temperature).

Results

At a concentration of 0.5 µM laurylgallate, 50% of the neuroblastoma cells were observed to undergo apoptosis. At 1.0 µM of laurylgallate, 100% of the cells had undergone apoptosis. These results indicates that laurylgallate is a very potent inducer of apoptosis inducer in neuroblastoma cells, and likely will enhance apoptosis is undifferentiated ES cells as well.

Example 6

Cell Culture Conditions for Human Embryonic Stem Cells

Manual Passaging of Human ES Cells

Human embryonic stem cells (HESCs) identified as BGN01 (BresaGen, Inc. Athens, Ga.) were used in this work. The HBESCs were grown in DMEM/F12 (50/50) supplemented with 15% FBS, 5% knockout serum replacer (Invitrogen), 1× non-essential amino acids (NEAA; Invitrogen), L-Glutamine (20 mM), penicillin (0.5 U/ml), streptomycin (0.5 U/ml), human LIF (10 ng/ml, Chemicon) and FGF-2 (4 ng/ml, Sigma). The human ES cells were grown on feeder layers of mouse primary embryonic fibroblasts that were mitotically inactivated by treatment with mitomycin-C. Feeder cells were re-plated at $1.2 \times 10^6$ cells per 35 mm dish. The mitotically inactivated fibroblasts were cultured for at least 2 days prior to the plating of HESCs. The HESCS were manually passaged onto fresh fibroblast feeder layers every 3-4 days using a fire-pulled Pasteur pipette. Briefly, the barrel of the Pasteur pipette was melted solid and drawn out to a solid needle approximately 1 cm long and approximately 25 µm in diameter, which was sequentially pressed through HESC colonies to form a uniform grid of cuts. The same needle was passed under the colonies to lift them from the feeder layer. Entire plates of HESCs were harvested, then the colonies were broken into individual pieces defined by the grid by gentle pipetting using a 5 ml serological pipette. The pieces from a single plate were split between 2 or 3 new plates that were coated with feeder layers of mitotically inactivated mouse primary embryonic fibroblasts.

Generation of Embryoid Bodies from Cells in the Crater of an ES Colony

The colony morphology of HESCs was observed to differ from the typically observed multilayered, domed colonies when HESCs were plated onto feeder cells that had been freshly plated. When HESC's were plated on feeder cells that were 0-6 hours old, but not on feeders that were 2 days old or older, typical BESC colonies formed except that in the central region of the colony a "crater" was observed. These central or crater cells formed a monolayer of uniform cells within a ring of multilayered HESCs. This monolayer was in direct contact with the tissue culture plastic, or the extracellular matrix that was left behind as the HESC colony had pushed out the underlying feeder layer. HESC colonies typically displace the underlying feeder layer as they seed and proliferate. Cells within the crater expressed the pluripotent marker Oct-4, although apparently at a reduced level compared to the surrounding ring of HESCs, indicating that they are a novel, partially differentiated cell type derived from the HESCs. This approach allowing the controlled development of crater HESC colonies occurred within 3 to 5 days and generated a uniform monolayer of central cells, as opposed to stochastic differentiation proceeding over several weeks and leading to a complex heterogeneous culture (Reubinoff et al., 2001 Nature Biotech, 19:1134-1140).

Formation of Essentially Serum Free Embryoid Bodies

Manually passaged HESC cultures were washed once with DMEM/F12 and once with DMEM/F12 supplemented with 1×N2 supplement (Invitrogen). Undifferentiated HESC colonies were harvested into uniform colony pieces of approximately 10-100 cells using the manual passaging methods described above. Pieces were transferred to 15 ml tubes and washed in 10 ml DMEM/F12 plus 1×N2 supplement. The pieces were left to settle, and the medium was aspirated. The pieces were resuspended in 2.5 ml of medium, and transferred to suspension dishes.

Suspension dishes were prepared by coating the surface of non-tissue culture plastic Petri dishes with a layer of agarose. The agarose coating was generated by pouring a molten solution of 0.5% agarose in DMEM/F12 medium into the Petri plates. The agarose coating was equilibrated in DMEM/F12 medium. Suspension cultures contained 2.5 ml of medium for 35 mm dishes, or 10 ml of medium for 100 mm dishes.

Essentially serum free embryoid bodies were cultured in suspension for up to four weeks, with replenishment of the medium every 3-4 days. The essentially serum free embryoid bodies were passaged every 5-7 days by cutting them into pieces with drawn out solid glass needles. At passaging, the embryoid bodies contained approximately 5000-10,000 cells and were divided into 410 pieces. Essentially serum free embryoid bodies formed in the presence of DMEM/F12 with 1×N2 and 4 ng/ml FGF-2 were termed sfEBs, while essentially serum free embryoid bodies formed in the presence of DMEM/F12 with 1×N2, 4 ng/ml FGF-2 and 50% MEDII were termed sfEBMs.

Essentially serum free embryoid bodies were generated from HESC crater cells by removing the feeder layer and HESCs growing on their surface. Watchmaker's forceps were used to hold the feeder layer at the side of the culture dish, and lifted this layer and the attached multilayered HESC from the dish. This manipulation peeled the feeder layer and the multilayered parts of the HESC colonies off of the dish and the monolayer crater cells were left attached to the dish. Glass needles were used to cut the crater monolayer to 50-200 cell size pieces, and lift them from the dish. These pieces were grown in suspension culture in the same serum free conditions as above (DMEM/12, 1×N2, L-Glutamine (20 mM), penicillin (0.5 U/ml), streptomycin (0.5 U/ml), 4 ng/ml FGF-2, with or without 50% MEDII).

Essentially serum free embryoid bodies were generated from protease passaged monolayer HESC colonies by Collagenase treatment HESC cultures were treated with protease, and then washed with DMEM/F12 1×N2 and 4 ng/ml FGF2. The monolayer colonies remained attached to the tissue culture plastic but became less tightly associated with the feeder layer. The feeder layer was removed using watchmaker's forceps as above. The monolayer HESC colonies were scraped off the dish using a glass needle, were transferred to a 15 ml tube and washed twice with the same medium and centrifuged (1000 rpm, 4 minutes). The HESC colonies were transferred to suspension dishes for development as essentially serum free embryoid bodies grown in the conditions described above (DMEM/F12, 1×N2, L-Glutamine (20 mM), penicillin (0.5 U/ml), streptomycin (0.5 U/ml), 4 ng/ml FGF-2, with or without 50% MEDII).

Immunostaining

For immunostaining, seeded embryoid bodies were rinsed with 1× PBS and fixed in 4% paraformaldehyde, 4% sucrose in 1× PBS for 30 minutes at 4° C. The cells were then washed in 1× PBS and stored at 4° C. Essentially serum free embryoid bodies in suspension were disaggregated and attached to a glass slide using a standard cytospin approach for immunostaining (Watson, 1966 J. Lab. Clin. Med., 68:494-501). sfEBMs were washed with 1× PBS and disaggregated with 0.05% typsin and gentle trituration. The cell suspension was washed with culture medium, pelleted and resuspended in HESC medium and $1 \times 10^4$ cells were attached to a glass microscope slide by centrifugation at 300 g for 4 minutes using a cytospin apparatus (Heraeus Instruments GmbH).

The attached cells were fixed immediately with 4% paraformaldehyde, and 4% sucrose in 1× PBS for 15 minutes, followed by three separate 5-minute washes in 1× PBS.

To perform immunostaining on fixed cells or cytospins, the samples were washed in block buffer (3% goat serum, 1% polyvinyl Pyrolidone, 0.3% Triton X-100 in wash buffer) for 30 minutes, and then incubated with the appropriate dilution of the primary antibody, or combination of antibodies for 4-6 hours at room temperature. The primary antibodies were anti-Map2, a mouse monoclonal antibody recognizing the Map-2 a, b and c isoforms (Sigma, Catalog # M4403) at a 1/500 dilution; anti-Nestin, a rabbit polyclonal antibody (Chemicon, Catalog # AB5922) at a 1/200 dilution; anti-Oct-4, a rabbit polyclonal antibody (Santa Cruz, Catalog # sc-9081) at a 1/200 dilution; sheep anti-Tyrosine Hydroxlyase (TH) antibody (Pel-Freez, Catalog # P60101-0) at a 1/500 dilution; anti-phosphoHistoneH3, a rabbit polyclonal antibody (Upstate, Catalog, # 06-570) at a 1/400 dilution; anti-SSEA4, a mouse monoclonal antibody (Developmental Studies Hybridoma Bank, Catalog # MC-813-70) at a 1/5 dilution. The cells were then washed in wash buffer (50 mM Tris-HCL pH 7.5, and 2.5 mM NaCl) 3 times for 5 minutes each wash. The cells were then incubated for a minimum of 2 hours in secondary antibodies diluted 1:1000, followed by washing in wash buffer. The secondary antibodies were appropriate combinations of Alexa-350 (blue), -488 (green) or -568 (red) conjugated goat anti-chicken, anti-rabbit, anti-sheep or anti-mouse antibodies, all available from Molecular Probes. Some samples were stained with 5 ng/ml DAPI to detect cell nuclei, and were then washed from overnight to 2 days in a large volume of wash buffer. The slides were mounted with mounting medium and a cover slip. Slides were visualized using either a NIKON TS100 inverted microscope or a NIKON TE 2000-S inverted microscope with a Q Imaging digital camera Example 7

Neural Differentiation of Essentially Serum Free Embryoid Bodies

HESCs were grown in suspension as embryoid bodies in essentially serum free conditions in the presence of 50% conditioned medium from the HepG2 hepatocarcinoma cell line (MEDII conditioned medium). The sfEBMs were cultured in suspension for up to 6 weeks, with passaging every 10 to 15 days. Passaging was performed by using glass needles to dissect the EBs into pieces, paying particular attention to the isolation of structured rosette regions. Non-rosette regions were generally removed from the culture during the passaging process, although the solid material could regenerate prior to the next passage.

Structured regions from essentially serum free embryoid bodies were seeded onto polyornithine and laminin coated permanox slides for adherent culture and further analysis. Essentially serum free embryoid bodies (sfEBs and sfEBMs) were cut into pieces using glass needles and 1-15 pieces were plated onto polyornithine/laminin coated permanox chamber slides in the same medium used for suspension culture. Polyornithine/laminin coated slides were prepared by diluting polyornithine to 20 µg/ml in tissue culture grade water, coating chamber wells at 37° C. overnight, washing the wells twice with water and coating the chamber wells with 1 µg/ml laminin at 37° C. for 2 hours to overnight. The slides were washed with water and 1× PBS prior to plating the cells. The embryoid bodies were cultured on these slides for 2-7 days.

Results

The structured rosette regions that were first observed morphologically between 7-10 days after derivation are neurectoderm/neural precursor/neural tube cell types. The rosette regions could comprise more than 50% of the mass of an essentially sfEBM. These structures take the form of spherical rosettes with a distinct radial appearance and central cavity surrounded by a ring of cells that is 4-8 cells in width. Other morphologically distinct regions that were observed in essentially serum free embryoid bodies included fluid filled cysts and homogeneous solid regions. Immunostaining of sections and cytospins demonstrated the presence of neurons (Map2+ cells) in sfEBMs in suspension. The neuronal networks were intermingled with, and surrounded the rosette structures. When seeded in adherent culture, rosettes grew as circular or ovoid radial structures and were surrounded by large interconnected mats of neurons that included many presumptive dopaminergic neurons that were TH+.

Example 8

Reduction in the Level of Oct-4 Protein in Differentiated HESCs

The Oct-4 transcription factor is a tightly regulated marker of pluripotency in the mouse, and expression of Oct-4 mRNA in human inner cell mass and ES cultures has been confirmed (Hansis et al., 2000 Mol. Hum. Reprod., 6(11):999-1004, and Reubinoff et al., 2000 Nature Biotech, 18:399-404). However, the restriction of Oct-4 protein to pluripotent cells in humans has not been examined thoroughly. Manually passaged HESC cultures containing domed or cratered colonies were stained with anti Oct-4 antibodies.

Figure 9:
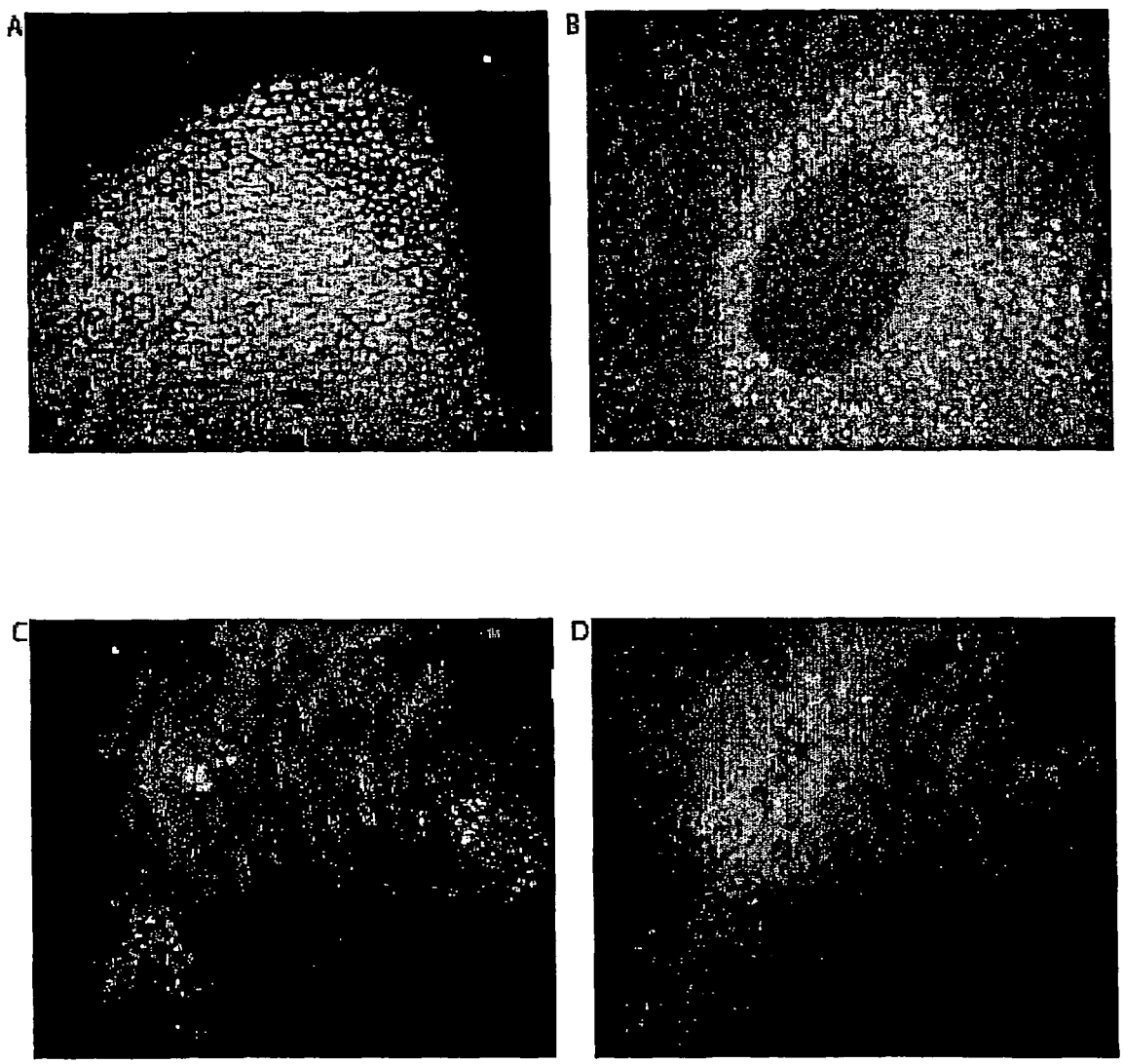

It was observed that the Oct-4 protein is expressed at high levels in undifferentiated HBESCs (FIG. 9A) and that levels of the Oct-4 protein are down-regulated following differentiation (FIG. 9B). An unexpected characteristic of immunostaining in the culture systems analyzed was that differentiated human cells retained a reduced but detectable level of Oct-4. However, when seeded sfEBM cultures were fixed and immunostained, a process that maintains the morphology of a culture, the difference between the two types of Octal expression was clearly distinguishable. High level Oct-4 expression was only observed as bright nuclear staining in tightly packed but evenly spaced cells. Therefore immunostaining for Oct-4 expression during neural differentiation in embryoid bodies was a suitable assay for the presence of residual compartments of pluripotent cells.

To monitor the persistence of pluripotent cells during sfEBM differentiation, essentially serum free embryoid bodies were generated from domed HESC colonies or monolayer crater ES cells. The sfEBMs were grown in suspension for 3-7 days, seeded onto polyornithine/laminin coated chamber slides, cultured for 3-5 days in the same medium and fixed for immunostaining. The presence of residual nests of pluripotent cells was demonstrated by clusters of high level Oct-4 immunostaining amongst the generalized low level of Oct-4 staining seen in the neuralized culture (FIG. 9C). The Oct-4 immunoreactivity was nuclear-specific. High level Oct-4 expression was not associated with the neural rosettes, which were visualized by the characteristic radial pattern of nuclei stained with DAPI (FIG. 9D). The presence of nests of residual pluripotent cells was still observed in sfEBMs that were cultured for over one month, with several passages specifically attempting to purify the neural rosette material, highlighting the persistent nature of these pluripotent cells and their implied teratoma forming potential when transplanted.

Example 9

Induction of Apoptosis by S18 Treatment of Seeded Embryoid Bodies

Treatment of EBs with S18 sfEBMs were derived from domed HESC colonies, grown in suspension for 24 days with one passage, and seeded to polyornithine/laminin coated chamber slides in DMEM/F12, supplemented with 1×N2 (Gibco), and 1% FCS. The seeded sfEBMs were treated with 6, 8 or 10 µM S18 dissolved in the media for 36 hours. The cultures were then washed with DMEM/F12, supplemented with 1×N2, and 4 ng/ml FGF-2 and incubated for 24 hours in 50% DMEM/F12, 50% MEDII, supplemented with 1×N2, and 4 ng/ml FGF-2 before fixing and staining with DAPI.

Apoptosis in seeded serum free embryoid bodies was monitored by morphological observation of cell death and DAPI staining to reveal apoptotic nuclei. Apoptotic nuclei were observed as obviously fragmented and degenerating nuclei, with small punctuate patterns of DAPI staining. Rosette regions from essentially serum free embryoid bodies in suspension were passaged further in the same medium, either withdrawing S18 or culturing the embryoid bodies for an additional 4 to 8 days in the presence of S18. Rosette regions were then seeded onto polyornithine/laminin coated slides for analysis of proliferation and differentiation to neural lineages.

Results

Figure 10:
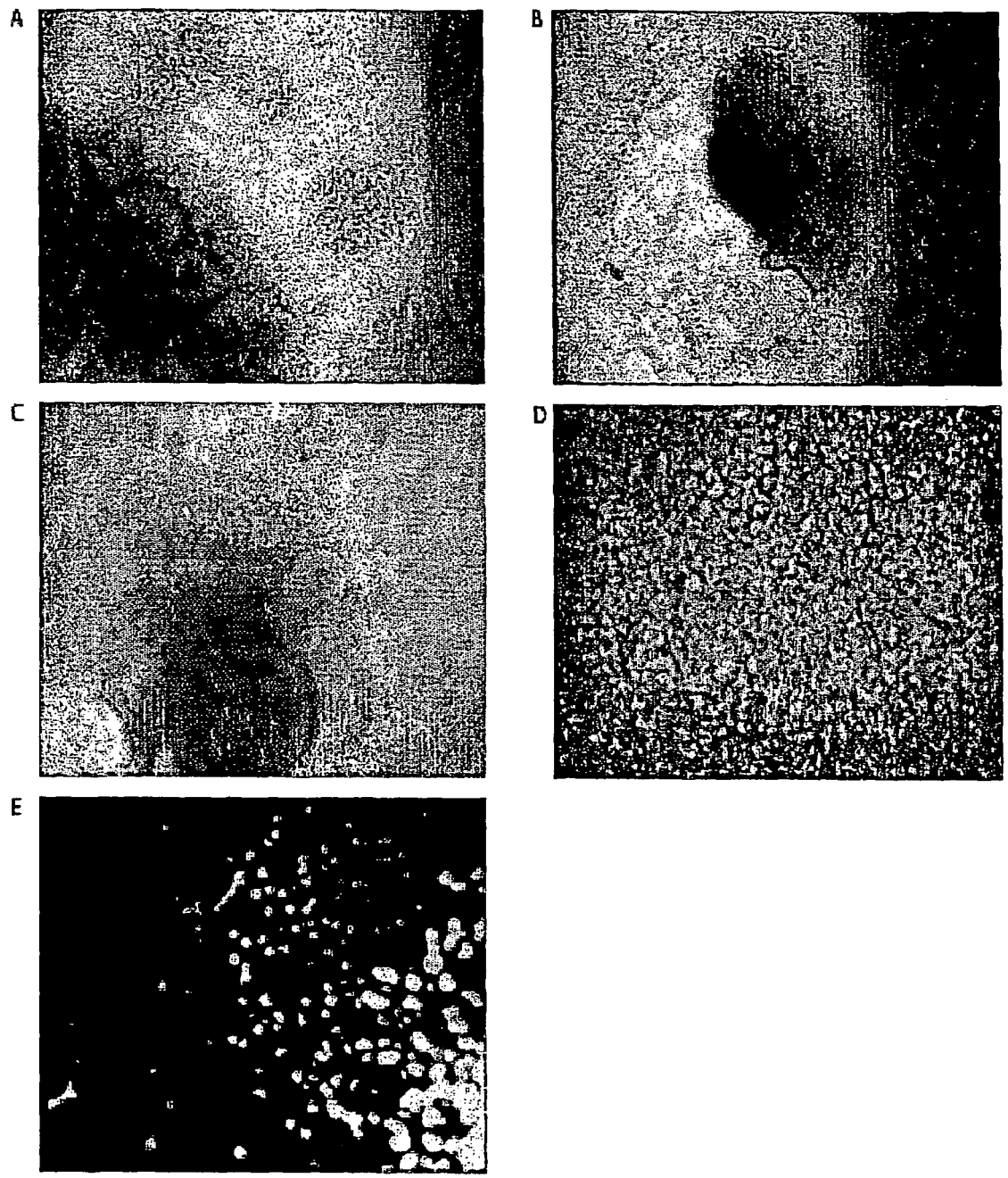

Prior to S18 treatment, the seeded cultures were heterogeneous and contained extensive neural rosette structures (FIG. 10A) as well as other cell types, such as presumptive glial cells, or other unidentified cell types. S18 treatment induced apoptosis of a large proportion of the culture at each dosage, and this effect was observed within 24 hours of treatment (FIGS. 10B, and 10C). No differences were observed between the different doses of S18. Overall, the general morphology of the culture was significantly affected, with a high level of cell death. The level of cell death is dependent upon the proportion of cell rosettes at the time of treatment. This proportion will vary, as will the level of cell death. Cellular debris was observed surrounding the seeded sfEBM, indicating that the cell types that had proliferated away from the sfEBM were killed. Neural rosette structures did not appear to be adversely affected by the S18 treatment, indicating that they were resistant to the induction of apoptosis mediated by this ceramide analog. Morphologically normal rosettes could be observed within an otherwise generally apoptotic culture (FIGS. 10C, and 10D). DAPI staining of cultures 24 hours after S18 withdrawal demonstrated that rosette cells had maintained morphologically normal nuclei, whereas cells on the periphery of the culture exhibited condensed nuclei, a characteristic of apoptotic cells (Kerr et al., 1972 Cancer, 26:239-257; FIG. 10E). The possibility that non-rosette cells in the multilayered region of the seeded sfEBM survived S18 treatment could not be addressed by this analysis. The observation that morphologically normal nuclei were an indicator of viable cells was strengthened by the observation of mitotic figures with DAPI staining, 24 hours after S18 withdrawal. This result indicated that the cells that survived treatment with S18 were capable of proliferation.

It was observed that non-rosette cells in an embryoid body would not survive when they were located more than around 5 cell distances from the edge of an essentially serum free embryoid body. It is hypothesized that this is presumably due to problems with poor exchange of oxygen or toxic waste metabolites. This degeneration of non-rosette cells appeared as regions containing degenerate nuclei as shown by DAPI staining. Rosette cells were not affected by distance from the edge of an essentially serum free embryoid body in the same manner, and healthy nuclei could be observed more than 20 cell diameters from the edge. Degenerate regions were not observed in sfEBMs derived from protease passaged cells, or after exposure to S18, further indicating the high purity of these neural rosette cell populations.

In summary, the S18 ceramide analog appeared to induce apoptosis efficiently in a range of different cell types in seeded serum bee embryoid bodies, and this induction appeared to be selective, with neural rosette cells appearing not to be affected. The application of S18 to embryoid bodies thus provided a population of neural rosette cells with high purity.

Example 10

Ceramide Analog S18 Treatment of Essentially Serum Free Embryoid Bodies in Suspension Essentially serum free embryoid bodies (sfEBMs) were generated as described in Example 6, and were exposed to S18 at different stages of their development in order to assess the timing of depletion of high Oct-4 expressing cells, and in order to determine when neural rosettes could be selected. The sfEBMs in suspension were treated with 10 μM S18 in 50% DMEM/F12, 50% MEDII, supplemented with 1×N2, Glutamine (20 mM), penicillin (0.5 U/ml), and streptomycin (0.5 U/ml) for varying amounts of time, and the sfEBMs were then evaluated histologically and by immunocytochemistry.

Essentially serum free embryoid bodies were derived from protease passaged cells and grown in the presence of 50% MEDII conditioned medium. The embryoid bodies were exposed to 10 μM S18 in the same medium from day 6 to 9 after derivation. At day 9 the S18 treated sfFBMs and matched control sfEBMs not exposed to S18 were fixed, embedded in plastic, cut to 3 micron sections and stained with DAPI to enable the precise determination of the proportion of the total healthy nuclei of an sfEBM that were rosette cell nuclei.

Results

It was not possible to derive sfEBMs from monolayer crater cells in the presence of 10 μM S18. No viable embryoid bodies were observed in the suspension culture after four days of S18 treatment, indicating that cells resistant to the induction of apoptosis were not present at this stage of the culture.

Conversely, sfEBMs at day 14 exhibited extensive neural rosette structures. This material was exposed to 10 μM S18 in 50% MEDII medium for 2 days, followed by manual passaging, and an additional 4 days in 10 μM S18 in the same medium. While 48 hours exposure to S18 did not have overt morphological effects on the sfEBM, when the embryoid bodies were manually passaged it was apparent that there was extensive apoptosis in the bodies. The non-rosette regions of the sfEBM fragmented when manipulated and released extensive stringy material that was indicative of genomic DNA from lysed cells. However, the rosette regions were morphologically normal and could be separated from all other degenerate regions of the sfEBM. The rosette pieces were incubated in 10 μM S18 for a further 4 days, and the medium was then switched to 50% DMEM/F12, 50% MEDII, supplemented with 1×N2, and 4 ng/ml FGF-2 at day 20 after the initial derivation of the embryoid bodies.

At day 21 some ceramide selected sfEBMs were seeded onto polyornithine/laminin coated slides, cultured in the same medium for an additional 8 days, and fixed for immunostaining. These seeded pieces developed as rosette cultures and mats of neurons were observed differentiating from these precursors.

Other ceramide selected sfEBMs were maintained in suspension, and were cultured for an additional 25 days, until 45 days after their initial derivation. These suspension cultures were passaged once during this time and initially proliferated at a rate similar to seeded neural rosettes, although their growth rate slowed after around day 40 after initial derivation. At day 35, the selected sfEBMs in suspension consisted of what appeared to be essentially pure neural rosette material, without any obvious regions comprised of different cell types (FIGS. 11A and 11B).

The S18 selected sfEBM that were seeded at day 21 were analyzed by immunocytochemistry with antibodies directed against Oct-4, Map2, TH and phospho-Histone H3. Staining with anti-Oct-4 indicated that no regions of high Oct-4 expression could be detected in any of the S18 treated samples (FIGS. 12A and 12B), indicating that no residual nests of pluripotent cells survived exposure to S18. The same result was seen in additional experiments when sfEBMs were generated and treated with 10 μM S18 in suspension prior to plating. Low level Oct-4 expression was detected in rosettes (FIGS. 12A, 12B; FIG. 13A) and other cell types that were present in the cultures. While these cultures had a high proportion of rosette cells, it was clear that other cell types were present, such as neurons, as well as other presumed neuralized cell types derived from the rosette precursor cells. Immunostaining with anti-Map2 (FIGS. 13B, and 13D), which recognizes a microtubule associated protein in the dendrites of mature neurons, demonstrated the presence of networks of differentiated neurons associated with neural rosettes. Staining with anti-TH, which recognizes tyrosine hydroxylase, the rate limiting enzyme in dopamine biosynthesis, demonstrated that presumptive dopaminergic neurons or their precursors were not ablated by exposure to 10 μM S18 (FIGS. 13C, and 13E). The histone H3 protein is phosphorylated during mitosis and is an effective marker of mitotic cells.

Figure 14:
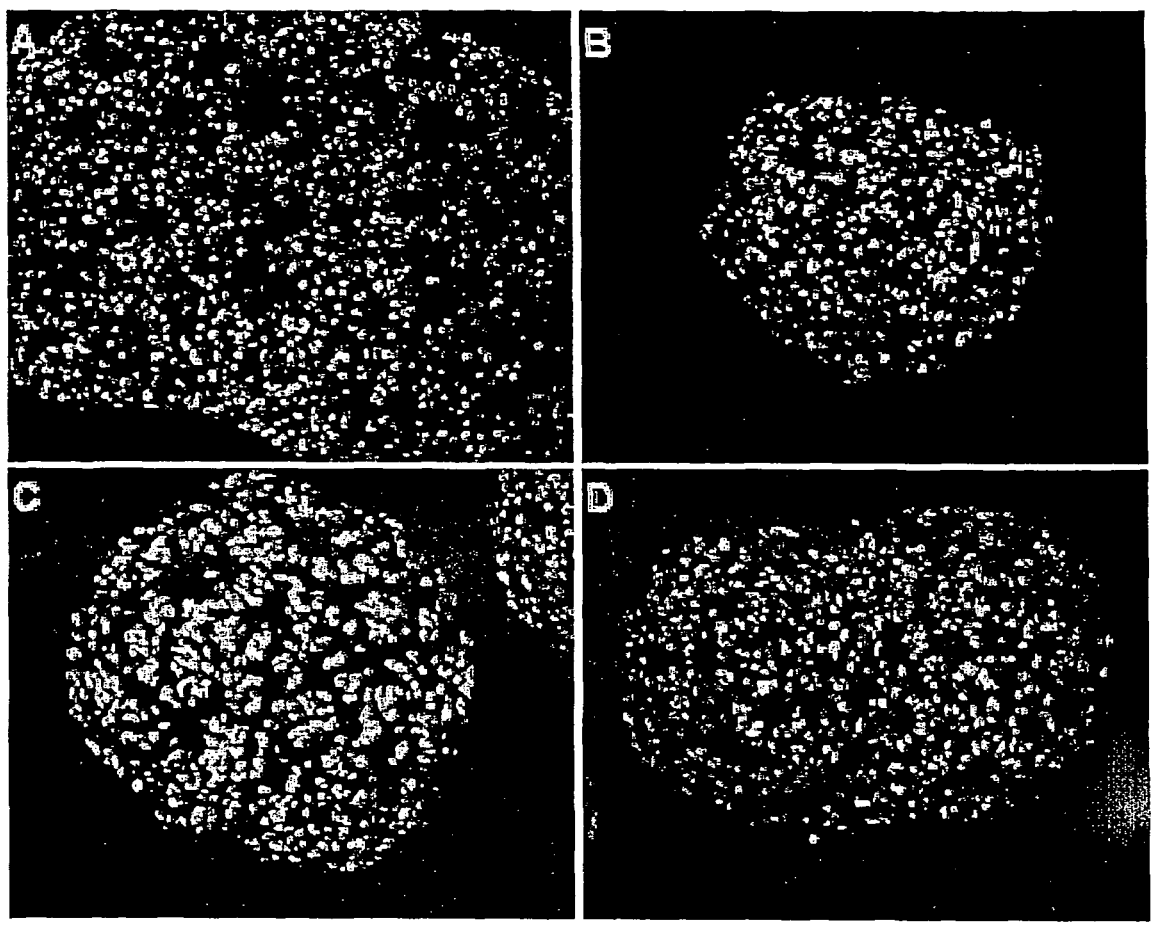

Seeded S18 selected sfEBMs were stained with anti-phosphoHistone H3 and DAPI (FIG. 13F). The presence of neural rosettes was indicated by their characteristic radial pattern. PhosphoHistone H3 expression demonstrated that these cultures were actively proliferating at the time they were fixed (day 28 after derivation, 8 days after withdrawal of S18). PhosphoHistone H3 staining within the neural rosettes indicated that these precursor cells were still mitotically active after exposure to S18 and could therefore be expanded further.

sfEBMs derived from protease passaged cells exposed to 10 μM S18 from day 6 to 9 after derivation were analyzed. In sections of control (untreated) sfEBMs, greater than 80% of the nuclei in the embryoid bodies were associated with rosettes (FIG. 14A). The rosette nuclei were generally elongated, in contrast to regions of smaller round nuclei that were not organized into rosettes. DAPI stained sections of S18 treated sfEBMs showed marked differences from the control sections (FIGS. 14B-D). The overall proportion of nuclei per measured area of sfEBM may have been reduced, but was generally still high However, nearly all nuclei in the treated sfEBM were elongated in appearance, and rosette structures were still clearly present. The small round nuclei of the presumptively non-rosette cells were very rarely noted. This indicated that a very pure population of neural precursor rosette cells had survived the incubation with S18.

It was observed that non-rosette cells located more than around 5 cell distances from the edge of an essentially serum free embryoid body would not survive. This effect was presumably due to problems with poor exchange of oxygen or toxic waste metabolites. The effect was characterized by regions containing degenerate nuclei as shown by DAPI staining. However, location did not affect rosette cells in the same manner, and healthy rosette nuclei could be observed more than 20 cell diameters from the edge of a sfEBM. Degenerate regions were not observed in sfEBMs derived from protease passaged cells, or after exposure to S18, further indicating the high purity of these neural rosette cell populations.

Example 11

Up-Regulation of Ceramide Expression During Neural Differentiation of Embryonic Stem Cells Methods Ceramide Analysis and Preparation of Ceramide-Containing Medium The extraction and quantitative determination of ceramide by high performance thin layer chromatography (HPTLC) was performed as described in Example 3. Quantitative determination of ceramide using the diacylglycerol (DAG) kinase assay was performed according to Signorelli and Hannun (2002 Methods Enzymol., 345:275-294).

Fumonisin B1 (FB1) or myriocin-treated (ceramide-depleted) differentiating ES cells were incubated with natural ceramide. To prepare the natural ceramide, 50 mg of EBs or NPs were resuspended in 500 µl of water, and after phase separation with 500 µl of $CHCl_3/CH_3OH$ (1:1 by vol.) the neutral lipids were recovered from the lower phase. The neutral lipids were evaporated to dryness with a gentle stream of nitrogen and redissolved in 1 ml of $CHCl_3$. The solution was applied to a silicic acid gel column (0.5 g) and fatty acids and cholesterol washed out with another 15 ml of $CHCl_3$ (Dasgupta and Hogan, 2001 J. Lipid Res., 42:301-308). The ceramide fraction was then eluted with 20 ml of $CHCl_3$/acetone (9:1, by vol.), evaporated to dryness, and the residue (approximately 6 nmoles of ceramide) dissolved in 20 µl of ethanol containing 2% dodecane (vol./vol.). Aliquots of 5 µl were mixed with 1 ml of medium, yielding a final concentration of 1.5 µM natural ceramide for induction of apoptosis (Ji et al., 1995 FEBS Lett., 358:211-214).

BrdU Labeling, Immunofluorescence Microscopy and TUNEL Assay

Differentiating ES cells at the EB8 cells were dissociated and grown for 24 hours on laminin/ornithin-coated cover slips (NP1 stage) in DMEM/F12 (50/50), supplemented with 1×N2 and 20 ng/ml FGF-2. Cells were incubated for 3 hours with 10 µM bromodeoxyuridine (BrdU) and the TUNEL assay or immunostainings performed after 5 hours of incubation. For immunostaining, cells were fixed with 4% paraformaldehyde in phosphate-buffered saline (PBS). Fixed cells were permeabilized with 0.2% Triton X-100 in PBS for 5 minutes at room temperature and immunostaining performed as described previously (Bieberich et al., 2001 J. Biol. Chem., 276:44396-44404). The nuclei were stained by treatment with 2 µg/ml Hoechst 33258 in PBS for 30 minutes at room temperature. Apoptotic nuclei were stained using the fluorescein FragEL TUNEL assay according to instructions of the manufacturer (Oncogene).

Statistical Analysis

Statistical analysis was performed as described in Example 3.

Results

Mouse ES cells were differentiated following a serum deprivation protocol as described above. This method yielded ES-derived cell cultures highly enriched in neural cells after 25 days in culture (Okabe et al., 1996 Mech. Dev., 59:89-102, Hancock et al., 2000 Biochem. Biophys. Res. Commun,. 271:18421). Neuronal differentiation was verified by staining of marker proteins using immunoblotting (FIG. 15) and immunofluorescence microscopy. ES cell differentiation was initiated by aggregating the ES cells to form embryoid bodies (EBs). The EBs were incubated in suspension culture in serum-containing medium for four days (stages EB1-EB4, FIG. 2). The differentiating EBs were then plated on tissue culture plates and allowed to attach in serum-containing medium for one day and then shifted to serum free medium for three additional days of culture (EB5-EB8, FIG. 2). The Oct-4 protein, a marker of pluripotent stem cells Resce and Scholer, 2001 *Stem Cells*, 19:271-278), was detected in the EB8 stage reflecting the presence of residual undifferentiated pluripotent stem cells within the EBs (FIG. 15, lane 1). No Oct-4 expression was detectable after the dissociation and replating of the EBs in serum-free, FGF-2-containing medium (FIG. 15, lanes 24). The serum-free conditions-did not support the proliferation of non-neural cell types, while the FGF-2 supported the robust proliferation of neural progenitor cells at stages NP1-NP4. The early neural precursor cell marker vimentin was only detected in EB8 and NP2 (FIG. 15, lanes 1 and 2) while the NP marker nestin was detected at low levels at EB8 and at high levels at NP2 and D1 (FIG. 15, lanes 1-3). The expansion of EB8 was followed by a large increase of the number of nestin-positive progenitor cells from about 60% at the NP2 stage, to more than 80% at NP4. Differentiation of NPs to glial cells and neurons was initiated by withdrawal of FGF-2 from the culture medium (stages D1-D4 in FIG. 2) and verified by staining for the glial marker protein GFAP and the neuronal marker proteins MAP-2 and synaptophysin (FIG. 15, lanes 3 and 4). No expression of NP markers was detected after D1 (FIG. 15, lane 4). Expression of GFAP was detected at D1 and D4 while MAP-2 and synaptophysin were only detected at D4, the most mature differentiation stage tested. It should be noted that less than 20% of Hoechst-stained cells showed neither GFAP nor MAP-2 staining, which verifies that the portion of non-neuronal cells within the fully differentiated culture was negligible.

To measure ceramide levels during ES cell differentiation, 50-100 mg of cells were harvested at different time points during differentiation. Sphingolipids were isolated using organic solvent extraction. As shown in FIGS. 16A and 16B, quantitative HPTLC and DAG kinase assay revealed that fibroblast-free, undifferentiated ES-cells (FIG. 16A, lane 2) contained less than 0.2+/−0.1 µg ceramide/mg cell protein. After four days of EB formation (EB4 stage) ceramide had increased to 0.4+/−0.1 µg ceramide/mg cell protein (FIG. 16A, lane 3). Endogenous ceramide was further elevated to 1.0+/−0.2 µg/mg cell protein by the EB8 stage of differentiation (FIG. 16A, lane 4). The increased ceramide concentration was maintained through the NP2 stage of differentiation (FIG. 16A, lane 5). In the D1 stage of differentiation, the ceramide concentration was found to be reduced by 70% (0.3+/−0.1 µg ceramide/mg cell protein) and did not change significantly after four days of differentiation (FIG. 16A, D1, D2, D4, lanes 6, 7 and 8). Taken together, these results indicate that the peak elevation of ceramide occurs during the initial formation of NPs upon serum deprivation of EBs and during NP expansion in the presence of FGF-2.

Apoptosis During Neuroprogenitor Expansion is Dependent on Ceramide Elevation

The degree of apoptosis in differentiating ES cultures was determined since it was previously proposed that ceramide elevation induces apoptosis in NPs (Bieberch et al., 2001 J. Biol. Chem., 276:44396-44404). As shown in FIG. 16B, the degree of apoptosis was quantified by counting TUNEL-stained cells. Apoptosis was elevated at the EB8 stage (~20+/−5%), and was highest at the NP2 stage (35+/−5%). The fraction of apoptotic cells rapidly decreased upon induction of neural differentiation and was already less than 20% at D1. Differentiated neurons at D4 did not show a significant degree of apoptosis (<10+/−5%). These results indicate that the peak time of apoptosis coincided with the peak elevation of endogenous ceramide. Consistent with this, inhibition of ceramide biosynthesis by incubation with 25 µM of the ceramide synthase inhibitor FB1 or 50 nM of the serine palmitoyltransferase inhibitor myriocin for 48 hours reduced the degree of apoptosis at the EB8 and NP2 stage by about 50%. At the NP2 stage, apoptosis proceeded in differentiating ES-cells that did not stain for nestin. In these cells, FB1 significantly reduced the degree of apoptosis. Apoptosis was restored by the addition of 30 µM N-acetyl sphingosine (C2-ceramide), 80 µM of the novel ceramide analog N-oleoyl serinol (S18), or 1 µM of natural ceramide that was extracted from differentiating ES cells. Taken together, these results showed that elevation of endogenous ceramide was a prerequisite for the induction of apoptosis in differentiating ES-cells at the NP2 stage.

Example 12

Ceramide-Induced Apoptosis is Dependent on PAR-4 Expression in Nestin-Negative Cells Methods RNA Preparation and RT-PCR Total RNA was prepared from differentiating stem cells using the Trizol method according to the manufacturer's (Life Systems) protocol. An aliquot (0.6-1.0 µg of RNA) was used for RT-PCR with the ThermoScript™ RT-PCR system following the supplier's (Invitrogen) instructions. PCR was carried out by applying 35 cycles with various amounts of first strand cDNA template (equivalent to 0.05-0.2 µg of RNA) and 20 pmoles of sense and antisense oligonucleotide primer. The following oligonucleotide primer sequences and annealing temperatures were used: PAR-4 (sense, 5'ccagcgccag-gaaaggcaaag3' (SEQ ID NO:6); antisense, 5'ctaccttgtcagct-gcccaacaac3' (SEQ ID NO:7); 61° C.), PKCζ (sense, 5'agecacgccgtttggaaagg3' (SEQ ID NO:8); antisense, 5'acactttattcctcagggcattacacg3' (SEQ ID NO:9); 58° C.), SPT1 (sense, 5'gctaacatggagaatgcactc3' (SEQ ID NO:10); antisense, 5'cttcctccgtctgctccac3' (SEQ ID NO:11); 53° C.), GAPDH (sense, 5'gaaggtgaaggtcggagtcaacg3' (SEQ ID NO:12); antisense, 5'ggtgatgggatttccattgatgacaagc3' (SEQ ID NO:13); 58° C.). The amount of template from each sample was adjusted until PCR yielded equal intensities of amplification.

Construction of PAR-4-RFP cDNA and Transfection of EB-Derived Cells

For construction of PAR-4-REP cDNA, RT-PCR was performed with the oligonucleotide primer pair sense 5'atggc-gaccggcggctatcg3' (SEQ ID NO:14) and antisense 5'ctacct-tgtcagctgcccaacaac3'(SEQ ID NO:15), using the first strand cDNA generated from embryoid bodies (EB8 stage) as template for the amplification reaction. The primers were endowed with the restriction enzyme cleaving sites Eco47III (sense) and SaII (antisense) for ligation of the PAR-4 specific amplification product into the multiple cloning site of HcRFP, a vector that encodes a far-red shifted variant of red fluorescent protein (Clontech). Differentiating ES cells at the NP1 stage were transfected with the PAR-4-RFP construct using the lipofectamine 2000 procedure according to the manufacturer's instructions (Invitrogen). The transfected cells were incubated in DMEM F12 (50/50), supplemented with 1×N2 and 20 ng/ml FGF-2, and the TUNEL assay or immunostainings were performed after 48 hours of incubation and NP formation. For depletion of ceramide, differentiating ES cell were incubated with 25 µM fumonisin B1 or 50 nM myriocin 48 hours prior to transfection with the PAR-4-RFP vector, and the inhibitor maintained in the medium throughout the post-transfection period. For induction of apoptosis, the novel ceramide analog S18 (40-100 µM), N-acetyl sphingosine (C2-ceramide, 10-30 µM), or natural ceramide isolated from EBs (0.5-1.5 µM) was added 48 hours after transfection with the PAR-4-RFP cDNA, and the degree of apoptosis quantified after 15-20 hours using TUNEL assays with paraformaldehyde-fixed cells as described above.

Morpholino Antisense Knockdown of Endogenous PAR-4

Endogenous expression of PAR-4 was suppressed by transfection of differentiating ES cells at the NP1 stage with 2 nmoles (per well in 24 wells plate) of the morpholino-based antisense oligonucleotide 5'cgatagccgccggtcgccatgttcc3' (SEQ ID NO:16) (see Guo et al., 1998, Nature Med., 4:957-962; Guo et al., 2001 Brain Res, 903:13-25) following the instructions of the manufacturer (GeneTools) in 0.5 ml of serum-free DMEM/F-12, 1XN2 supplemented with 20 ng/ml FGF-2. For induction of apoptosis, the novel ceramide analog S18 (40-100), N-acetyl sphingosine (C2 ceramide, 130' K, or natural ceramide isolated from EBs (0.5-1.5 µM) was added 48 hours after transfection with the anti-PAR-4 morpholino, and the degree of apoptosis quantified after 15-20 hours using TUNEL assays with paraformaldehyde-fixed cells as described above.

Protein Isolation and Immunoblotting

The amount of protein was determined following a modified Folin phenol reagent (Lowry) assay essentially as described in Wang and Smith (1975 Anal. Biochem., 63:414-417). Protein extracted with detergent was precipitated according to the Wessel and Flueggb method (Wessel and Flugge, 1984 Anal. Biochem, 138:141-143). SDS-PAGE was performed using the Laemmli method followed by immunoblotting (Laemmri, 1970 Nature, 227:680-685).

Results

Expression of PAR-4, an inhibitor protein of PKCζ, has been reported to be a prerequisite for induction of apoptosis by incubation of differentiating ES cells with S18 or C2-ceramide (Bieberich et al., 2001 J. Biol. Chem., 276:44396-44404). These results were confirmed by incubation of FB1-treated cells at the NP2 stage with S18, C2-ceramide, or natural ceramide that was extracted from differentiating ES cells. Apoptosis was only seen in cells that expressed PAR-4. S18 or ceramide incubation did not alter the number of PAR-4 positive cells but it restored the degree of apoptosis to that found with cells that were not pre-treated with FB1. S18 incubation did not alter the concentration of endogenous ceramide, indicating that ceramide elevation was not a byproduct of apoptotic cells but the cause of apoptosis. Notably, the majority of apoptotic cells (>90%) that stained for PAR-4 were nestin-negative.

To suppress PAR-4 expression, ES cells at the NP1 stage were transfected with a PAR-4 specific morpholino phophorodiamidate antisense oligonucleotide (morpholino) that was designed on the basis of a previously published antisense oligonucleotide sequence (Guo et al., 1998, Nature Med., 4:957-962; Guo et al., 2001 Brain Res., 903:13-25). Morpholinos have been shown to avoid many of the pitfalls associated with conventional antisense oligonucleotides and have been successfully used for transfection of embryos and cultured cells (Morcos, 2001 Genesis, 30:94-102). The number of TUNEL-stained cells in the negative control (NPs 48 hours after transfection with a standard morpholino) was equivalent to that found with untransfected cells (35%, see FIG. 16B), indicating that the degree of apoptosis was not affected due to any unspecific effect of the morpholino. This result was consistent with the observation that the expression level of PAR-4 in untransfected and control morpholino-transfected NPs was the same (FIG. 17, lanes 1 and 2). Incubation of control morpholino-transfected NPs with 80 (LM 818 increased the number of apoptotic cells to that found with S18-treated, untransfected cells (more than 80%). However, transfection of NPs with a PAR-4 specific antisense morpholino reduced S18-induced apoptosis to a level less than 30%. Consistently, transfection with the PAR-4 antisense morpholino suppressed the expression level of PAR-4 to about 25% of that detected in untransfected cells (FIG. 17, lane 3).

To determine the effect of elevated PAR-4 expression, myriocin-treated ES cells were transfected at the NP1 stage with PAR-4 linked to far-red-shifted red fluorescent protein (PAR-4-RFP; FIG. 17, lane 4). PAR-4-RFP expression by itself did not induce apoptosis in the transfected cells. However, apoptosis was observed when transfected cells were incubated with 40 µM S18, a concentration at which no or only a low degree of ceramide analog-induced apoptosis occurred in untransfected or mock (RFP)-transfected cells. Apoptosis was induced almost exclusively in PAR-4-RFP expressing cells, whereas the population of cells without PAR-4-RFP remained unaffected. In summary, these results show that the expression and/or elevation of PAR-4 were a prerequisite for ceramide-induced apoptosis in differentiating ES cells.

Apoptosis is Induced by Simultaneous Up-Regulation of PAR-4 and Ceramide Biosynthesis To identify the genes involved in the regulation of apoptosis in differentiating embryonic stem cells, the temporal expression pattern of pro- or anti-apoptotic proteins and ceramide biosynthesis/metabolism during EB and NP formation were determined. FIG. 18A shows that PAR-4 expression was significantly elevated at the EB8 and NP2 stages (lanes 1 and 2). By the first day of neural differentiation (D1) the PAR-4 level dropped to less than 20% of that at NP2 (FIG. 18A, lanes 2 and 3). The peak time of PAR-4 expression at the NP2 stage was concurrent with caspase 3 activation and increased PCNA (proliferating cell nuclear antigen) levels (FIG. 18A, lane 2). PCNA is a marker for mitotic cells (Chan et al.,2002 Anat. Rec., 267, 261-276), indicating that PAR-4 elevation and caspase 3 activation is predominant at stages with a large number of proliferating stem cells. The expression of PKCζ did not change during neuronal differentiation PKCζ activity is inhibited by ceramide-enhanced binding of PAR-4 leading to an up-regulation of the caspase 9 and 3-dependent apoptotic pathway (Diaz-Meco et al., 1998 Cell, 86:777-786; Mattson, 2000 Brain Pathol., 10:300-312). The participation of caspase 9 in ceramide-induced apoptosis of differentiating ES cells was confirmed by the observation that pre-incubation with the cell permeable caspase 9 inhibitor peptide LEHD-CHO suppressed apoptosis that was inducible with S18 or natural ceramide isolated from ES cells. Up-stream regulators of caspase 3, in particular anti-apoptotic Bcl-2 and pro-apoptotic Bad, were inversely regulated suggesting activation of caspase 3 via the mitochondrial death pathway (FIG. 18A). However, a high degree of Bad phosphorylation (pBAD) was detectable at NP2 (FIG. 18A, lane 2), indicating the presence of both, apoptotic and anti-apoptotic signaling at this stage. The expression of Bad dropped and that of Bcl-2 increased during D1 and D4, consistent with lower levels of caspase 3 activation and apoptosis at these differentiation stages (FIG. 18A, lanes 3 and 4).

The gene expression of PAR-4, PKCζ and serine palmitoyl transferase (SPT) that catalyzes the initial reaction of ceramide biosynthesis were analyzed using RT-PCR. The highest level of PAR-4 mRNA was found at the EB8 stage (FIG. 18B, lane 2). Interestingly, the level of PAR-4 mRNA dropped within 48 hours from EB8 to NP2 (FIG. 18B, lanes 2 and 3), although the NP2 stage showed the highest concentration of PAR-4 protein (FIG. 18A, lane 2). The transcription of PKCζ appeared not to be modulated during neuronal differentiation, which is consistent with the unchanged level of protein expression. There is a more than tenfold increase in gene expression of SPT subunit 1-(SPT1) at the EB8 stage, whereas the transcription of the subunit 2 (SPT2) mRNA remained unchanged at all differentiation stages from EB8 to D4 (FIG. 18B, lanes 2-4). Up-regulation of SPT1 gene expression is consistent with elevated ceramide biosynthesis at EB8 and NP2 since SPT1 activates SPT2 (Hanada et al., 1998 J. Biol. Chem., 273:33787-33794). Taken together, the results showed that apoptosis of differentiating ES cells at the NP2 stage is most likely induced by up-regulation of ceramide biosynthesis and elevation of PAR-4 expression.

Discussion

The results showed that NPs containing high levels of both ceramide and prostate apoptosis response (PAR-4) undergo apoptosis at high frequency. Several lines of evidence show that this elevation is the cause rather than the effect of apoptosis. Inhibition of ceramide biosynthesis with FB1 or myriocin reduces the degree of apoptosis, which can be restored by the addition of natural ceramide or ceramide analogs. Restoration of apoptosis is not accompanied by elevation of endogenous ceramide, ruling out a significant degree of ceramide formation by hydrolysis of ceramide derivatives in dying cells. Elevation of endogenous as well as the addition of natural ceramide or ceramide analogs, however, restores apoptosis only in cells with high expression of PAR-4. This is clearly shown with NPs that were transfected with an anti-PAR-4-morpholino oligonucleotide or PAR-4-RFP cDNA before incubation with ceramide analogs. Antisense knock-down of PAR-4 eliminates S18-inducible apoptosis even at high concentration of the ceramide analog, whereas overexpression results in apoptosis at low concentration of S18, but only in PAR-4-RFP expressing cells. These experiments thus support the main hypothesis that both elevation of PARK and ceramide are necessary to induce apoptosis.

Example 13

Asymmetric Distribution of PAR-4 and Nestin During Mitosis of Neuronal Stem Cells The apparent paradoxical elevation of both the proliferation marker PCNA and the pro-apoptotic, active caspase 3 at the EB8 and NP2 stages of ES cell differentiation prompted the examination of the patterns of mitosis and apoptosis in individual cells by immunofluorescence microscopy for mitosis/apoptosis markers and BrdU labeling. The predominance of mitosis or apoptosis in NPs was analyzed by immunofluorescence staining for nestin. As shown in FIG. 19, simultaneous staining by TUNEL assay and antibodies against nestin and PCNA revealed that the major portion (92%) of TUNEL positive cells were nestin-negative. Most of the TUNEL positive cells (75%) expressed PCNA as well, indicating that apoptosis followed immediately after mitosis or during the attempt to enter the next mitotic cycle. However, no TUNEL signal was detected if cells co-expressed PCNA and nestin. These observations prompted the examination of the distribution of pro-apoptotic signals in proliferating cells, in particular the expression of PAR-4 and ceramide. In double staining experiments for TUNEL and one additional marker, ceramide or PAR-4 was expressed in TUNEL-positive as well as TUNEL-negative cells (FIG. 19). The majority of the TUNEL-positive cells expressed PAR-4 (94%), ceramide (98%), or PCNA (75%) whereas TUNEL-negative cells showed a lower frequency for PAR-4 (27%), ceramide (34%), or PCNA (45%) expression (FIG. 19). In double staining experiments for two markers, PAR-4 and ceramide were independently distributed (31% observed vs. 24% expected frequency for the expression of both ceramide and PAR-4, FIG. 20) within the total cell population. In triple staining experiments, however, 97% of the TUNEL-positive cells showed PAR-4 and ceramide expression, whereas less than 2% of the TUNEL-negative cells were stained for PAR-4 as well as ceramide. Taken together, these results indicated that the expression of both PAR-4 and ceramide was required to induce apoptosis in proliferating (PCNA-positive) stem cells or NPs. This assumption was also supported by immunostaining for BrdU incorporation in apoptotic cells. In differentiating ES cells at the NP2 stage, apoptosis was observed in 70% of cells within 5 hours after BrdU labeling. Hence, in differentiating ES cells at the NP stage, apoptosis (activation of caspase 3) rapidly followed mitosis BrdU incorporation).

The results from ceramide and PAR-4 double immunostaining experiments suggested that either ceramide or PAR-4 were sequestered to only one daughter cell during cell division. Mitotic cells in anaphase (mitosis stage VII) and telophase (mitosis stage VIII) were identified by the polarized orientation of nuclei upon fixation and staining with Hoechst dye, a useful marker for the identification of different mitotic stages (Leblond & El-Alfy, 1998 Anal. Rec., 252:426-443). Ten out of 5000 cells were found to be in mitosis stage VII or VIII. Ceramide was homogenously distributed to the two daughter cells, whereas PAR-4 was sequestered to only one daughter cell. The daughter cells with elevated PAR-4 appeared apoptotic, as PAR-4 co-localized with ceramide in membrane blebs that are typical for apoptosis. Ceramide-induced apoptosis in PAR-4 positive cells was executed by the caspase 9-to-caspase 3 cascade as shown by co-immunostaining of elevated PAR-4 and cleaved caspase 3 in TUNEL positive cells.

The lack of nestin expression in PAR-4 positive cells suggested that nestin and PAR-4 were sequestered asymmetrically to the daughters of dividing NPs. Immunostaining showed that nestin and PAR-4 were indeed asymmetrically distributed in mitosis stage VIII cells. The PAR-4-positive, but nestin-negative cells underwent apoptosis, whereas the nestin-positive cells were non-apoptotic and expressed either none or significantly less PAR-4 than nestin-negative cells. The absence of nestin-staining in apoptotic cells is consistent with the results shown in FIGS. 17, 19, and 20. These data are also consistent with the low number of cells (6%) that co-stained for PAR-4 and nestin (FIG. 20). In cases where residual PAR-4 was present in nestin-positive daughter cells the PAR-4 and nestin were clearly separated. Taken together, these observations suggested that PAR-4 is partitioned specifically into nestin-negative daughter cells.

Discussion

In cultures of NPs derived from ES cells it was determined that the expression of PAR-4 and nestin is largely segregated to two separate populations of progenitors. Nestin(+)/PAR-4(−) cells are far less prone to apoptosis induced by high levels of intracellular ceramide, while cells undergoing apoptosis are almost always nestin(−)/PAR-4(+). The expression of high levels of PARK in an apoptotic subpopulation is consistent with previous studies demonstrating that overexpression of PAR-4 reduces WT1- or NF-κB-mediated Bcl-2 expression, thus suppressing the cells' self defense mechanism against ceramide-induced apoptosis (Camandola and Mattson, 2000 J. Neurosci. Res., 61:134-139; Cheema et al., 2003 J. Biol. Chem., in press). The critical role of NF-κB for cell survival has been shown by the observation that central neuron survival relies on the constitutive activity of NF-κB (Bhakar et al., 2002 J. Neurosci., 22:8466-8475). It has also been shown that elevation of PAR-4 underlies neuronal cell death in several neurodegenerative diseases (Guo et al., 1998 Nature Med., 4:957-962; Xie et al., 2001 Brain Res., 915:1-10). Surprisingly, in cells that express both PAR-4 and nestin, the two proteins are strictly sequestered to different parts of the cell. This sequestration occurs already during mitotic cell division of the parental cells, resulting in one daughter cell that is predominantly nestin-positive, while the other one contains mainly PAR-4, but no or only low amounts of nestin. This reveals a novel localization of a pro-apoptotic signal to one of the daughter cells resulting from stem or NP cell division. The asymmetric distribution of PAR-4 in the nestin-negative daughter cells may be a mechanism to regulate the number of differentiating cells produced from mitotically active progenitor/stem cells. At present, it has not been determined whether the asymmetric distribution results from asymmetric inheritance of nestin and PAR-4 that have already expressed before cell division, or whether it arises from a distinct gene expression in each daughter cell during cell division, therefore both remain possibilities.

Example 14

A Model for Asymmetric Cell Division, Apoptosis and Differentiation

Based on these observations, a model for asymmetric cell division, apoptosis, and differentiation of neuronal stem cells is suggested, which is shown in FIG. 21. Differentiating stem cells up-regulate the expression of nestin, ceramide and PAR-4 prior to or during cell division. Ceramide and PAR-4 elevation at these stages is most likely caused by up-regulation of gene expression for PAR-4 and serine palmitoyltransferase activating subunit 1 (SPT1) in EB8. This indicates regulation of de novo ceramide biosynthesis and PKCζ activity by the respective regulatory proteins, but not by basal enzyme activities. During mitosis, ceramide is evenly sequestered to the two daughter cells, whereas PAR-4 and nestin are asymmetrically distributed. The nestin(−)/PAR-4(+) daughter cell undergoes ceramide-induced apoptosis, whereas the nestin(+)/PAR-4(−) daughter cell may again divide or further differentiate into a neuronal or glial precursor cell. At this point, rapid passage of the mitotic cycle is desirable in order to sequester PAR-4 to one daughter cell and to avoid abortive mitosis before accomplishment of cell division (Liu and Greene, 2001 Cell Tissue Res., 305:217-228).

There is growing evidence that elevation of ceramide is a major regulatory factor for induction of apoptosis during in vitro differentiation of neuronal cells (Herget et al., 2000 J. Biol. Chem., 275:30344-30354; Bieberich et al., 2001 J. Biol. Chem., 276:44396-44404; Toman et al., 2002 J. Neurosci. Res., 68:323-330). During ongoing differentiation, ceramide may be converted into glycosphingolipids and/or sphingomyelin, thereby protecting the neuroprogenitor cells from further ceramide accumulation. Most recently, it has been found that the biosynthesis of complex gangliosides from simple glycosphingolipids activates the IGF-1-to-MAPK cell survival pathway (Bieberich et al., 2001 J. Biol. Chem., 276: 44396-44404). Further, it was suggested that this biosynthesis is concurrent with migration of NPs from the ventricular to the intermediate zone of embryonic mouse brain. It is thus very likely that sphingolipid-dependent apoptosis of neuronal stem cells in the ventricular zone and cell survival in the intermediate zone is regulated by a two-step mechanism. Ceramide induced apoptosis of subventricular stem cells relies on the simultaneous expression of ceramide and PAR-4 and its asymmetric distribution during mitotic cell division. Only the PAR-4(+) daughter cells will undergo ceramide-induced apoptosis and make room for nestin(+)/PAR-4(−) NPs. In the second step, ceramide is converted to ceramide-1-phosphate, glycosphingolipids and/or sphingomyelin, thus protecting progenitor cells from further ceramide accumulation. The simultaneous elevation of ceramide and PAR-4, and subsequent apoptosis in nestin(−) cells may thus be a mechanism to select for nestin(+) neuronal progenitors or a mechanism to eliminate young post-mitotic neurons via expression of high levels of PAR-4 and ceramide. In future studies, endogenous and exogenous signals that orchestrate sphingolipid biosynthesis and the expression/asymmetric distribution of PAR-4 and nestin during neural differentiation of stem cells in vitro and embryonic mouse brain in vivo will be determined.

We claim:

1. A method of producing a human neural cell comprising,
a) providing a pluripotent human cell; and
b) culturing the pluripotent human cell with a composition comprising a ceramide compound selected from the group consisting of N-(2-hydroxy-1-(hydroxymethyl)

ethyl)-palmitoylamide ("S16"), N-(2-hydroxy-1-(hydroxymethyl)ethyl)-oleoylamide ("S18"), N,N-bis(2-hydroxyethyl)palmitoylamide ("B16"), N,N-bis(2-hydroxyethyl)oleoylamide ("B18") N-tris(hydroxymethyl)methyl-palmitoylamide ("T16"), N-tris(hydroxymethyl)methyl-oleoylamide ("T18"), N-acetyl sphingosine ("C2-ceramide"), and N-hexanoylsphingosine ("C6-ceramide") to produce the human neural cell.

2. The method of claim 1, wherein the pluripotent human cell is a differentiating pluripotent human cell.

3. The method of claim 1, comprising the intermediate step of forming an embryoid body comprising the pluripotent human cell prior to culturing a cell from the embryoid body with the ceramide compound.

4. The method of claim 3, wherein the embryoid body is formed by culturing the pluripotent human cell with an essentially serum free medium.

5. The method of claim 4, wherein the essentially serum free medium is a MEDII conditioned medium.

6. The method of claim 5, comprising the additional steps of,
   a) dispersing the embryoid body to an essentially single cell suspension;
   b) culturing the essentially single cell suspension comprising the pluripotent human cell in an adherent culture with a composition comprising the ceramide compound.

7. The method of claim 6, wherein the composition comprising the ceramide compound further comprises a MEDII conditioned medium.

8. The method of claim 5 wherein the MEDII conditioned medium is a Hep G2 conditioned medium.

9. The method of claim 7, wherein the composition comprising the ceramide compound is essentially serum free.

10. A method of producing a human neural cell comprising,
   a) providing a pluripotent human cell; and
   b) culturing the pluripotent human cell with a composition comprising a ceramide compound of the structure

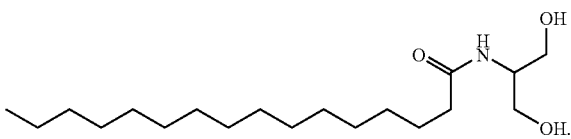

11. A method of producing a human neural cell comprising,
   a) providing a pluripotent human cell; and
   b) culturing the pluripotent human cell with a composition comprising a ceramide compound of the structure

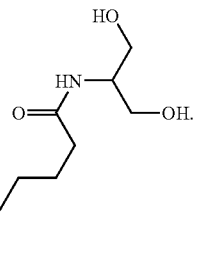

12. The method of claim 1, wherein the concentration of the ceramide compound is from approximately 0.1 μM to approximately 1000 μM.

13. The method of claim 1, wherein the concentration of the ceramide compound is from approximately 1 μM to approximately 100 μM.

14. The method of claim 1, wherein the concentration of the ceramide compound is from approximately 5 μM to approximately 50 μM.

15. The method of claim 1, wherein the concentration of the ceramide compound is approximately 10 μM.

16. The method of claim 1, wherein the duration of culturing the human pluripotent cell with the ceramide compound is from approximately 6 hours to 10 days.

17. The method of claim 1, wherein the pluripotent human cell is selected from the group consisting of a human embryonic stem cell, a human inner cell mass (ICM)/epiblast cell, a human primitive ectoderm cell, and a human primordial germ cell.

18. The method of claim 1, wherein the pluripotent human cell is a human embryonic stem cell.

19. The method of claim 1, wherein the human pluripotent cell is a multipotent cell.

20. The method of claim 19, wherein the multipotent cell is a neural precursor cell.

* * * * *